United States Patent
Man et al.

(10) Patent No.: US 10,434,095 B2
(45) Date of Patent: Oct. 8, 2019

(54) 3-(1-OXO-4-((4-((3-OXOMORPHOLINO) METHYL)BENZYL)OXY)ISOINDOLIN-2-YL) PIPERIDINE-2,6-DIONE AND ISOTOPOLOGUES THEREOF

(71) Applicant: Celgene Corporation, Summit, NJ (US)

(72) Inventors: Hon-wah Man, Princeton, NJ (US); Alexander L. Ruchelman, Cream Ridge, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 15/881,501

(22) Filed: Jan. 26, 2018

(65) Prior Publication Data

US 2018/0243285 A1    Aug. 30, 2018

Related U.S. Application Data

(60) Provisional application No. 62/451,589, filed on Jan. 27, 2017.

(51) Int. Cl.
| | | |
|---|---|---|
| *A61K 31/4545* | (2006.01) | |
| *C07D 413/14* | (2006.01) | |
| *A61P 35/00* | (2006.01) | |
| *A61K 31/4035* | (2006.01) | |
| *A61K 31/5377* | (2006.01) | |

(52) U.S. Cl.
CPC ...... *A61K 31/4545* (2013.01); *A61K 31/4035* (2013.01); *A61K 31/5377* (2013.01); *A61P 35/00* (2018.01); *C07D 413/14* (2013.01)

(58) Field of Classification Search
CPC ............ A61K 31/4035; A61K 31/4545; A61K 31/5377; C07D 413/14
See application file for complete search history.

(56) References Cited

U.S. PATENT DOCUMENTS 8,518,972 B2    8/2013 Man et al.
2014/0046057 A1    2/2014 Cohen et al.

FOREIGN PATENT DOCUMENTS

WO    WO 2014/116573 A1    7/2014

OTHER PUBLICATIONS

Wolff, Manfred E. "Burger's Medicinal Chemistry, 5ed, Part I", John Wiley & Sons, 1995, pp. 975-977.*
Banker et al, "Modern Pharmaceutics, 3ed.", Marcel Dekker, New York, 1996, pp. 451 and 596.*

* cited by examiner

*Primary Examiner* — Valerie Rodriguez-Garcia
(74) *Attorney, Agent, or Firm* — Jones Day

(57) ABSTRACT

Provided are 4'-arylmethoxy isoindoline compounds, e.g., 3-(1-oxo-4-((4-((3-oxomorpholino)methyl)benzyl)oxy) isoindolin-2-yl)piperidine-2,6-dione, or an isotopologue thereof, or an enantiomer or a mixture of enantiomers thereof. Pharmaceutical compositions comprising and methods for using the compounds are also disclosed.

19 Claims, 5 Drawing Sheets

3-(1-OXO-4-((4-((3-OXOMORPHOLINO)METHYL)BENZYL)OXY)ISOINDOLIN-2-YL)PIPERIDINE-2,6-DIONE AND ISOTOPOLOGUES THEREOF

This application claims priority to U.S. Provisional Application No. 62/451,589, filed Jan. 27, 2017, the entirety of which is incorporated herein by reference.

FIELD

Provided herein are 4'-arylmethoxy isoindoline derivatives. Pharmaceutical compositions comprising the compounds and methods for treating, preventing and managing various disorders using the compounds and compositions are also disclosed.

BACKGROUND

Many types of hematological and solid cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties, including tumor necrosis factor α (TNF-α).

A variety of other diseases and disorders are also associated with, or characterized by, undesired angiogenesis. For example, enhanced or unregulated angiogenesis has been implicated in a number of diseases and medical conditions including, but not limited to, inflammatory diseases, allergic diseases, and autoimmune diseases. Examples of such diseases and conditions include, but are not limited to: scleroderma, Sjögren syndrome, systemic lupus erythematosus, and solid and hematological cancers.

Certain 4'-arylmethoxy isoindoline compounds, such as 3-(4-((4-(morpholinomethyl)benzyl)oxy)-1-oxoisoindolin-2-yl)piperidine-2,6-dione, and methods of use and pharmaceutical compositions thereof have been described in U.S. Pat. No. 8,518,972, the entirety of which is incorporated herein by reference. The afore-mentioned compound has been shown to be potent in treating cancer, disorders associated with angiogenesis, an immunodeficiency disorder, scleroderma, lupus, or Sjögren syndrome, or a TNFα related disorder.

After administration of pharmacologically active compounds, some of the them are absorbed and directly produce physiological effects, whereas others must undergo a series of metabolic reactions and are converted to active metabolite that can retain the affinity of the pre-metabolic drug for the pharmacological target. Thus, the chemical structure of pharmacologically active metabolites may differ from the compounds originally administered.

In practice, it is believed that the drug effect and the efficacy of a metabolite may differ from its pre-metabolic form, e.g., in the affinity to the pharmacological target, the functional activity, the plasma protein binding, the membrane permeability, or pharmacokinetics. This can have consequences regarding reduced side effects, improved drug safety, drug potency, and drug effectiveness and proves that active metabolites are not merely another form of pre-metabolic compounds, but constitute at least in some instances new and unique substances. It is believed that the differences between a metabolite and its pre-metabolic compound in side effects, drug safety, drug potency and drug effectiveness may directly influence the pharmacologic dosing regimen of the metabolite as a drug itself.

Due to the fact that the chemical structure of active metabolites differs from the compounds originally administered, the metabolite may possess different physicochemical properties which can open the door to new routes of administration. For example, it may be possible to provide a transdermal therapy in order to circumvent liver-passage.

There may be circumstances where it is desired to reduce the administration of the pre-metabolic drug or where its administration is even contraindicated. For example, in patients where metabolism of the pre-metabolic drug is inhibited, either because of the patient's hepatic enzymatic activity levels or because of ingestion of substances that have inhibitory effects on hepatic metabolism, particularly on members of the cytochrome P450 family of oxidizing enzymes (CYPS) such as, e.g., CYP3A4, patients may be advised to reduce the amount of the pre-metabolic drug being taken.

Thus, there remains a need for identification and development of additional 4'-arylmethoxy isoindoline compounds and for identification and development of active metabolites of such 4'-arylmethpxy isoindoline compounds, which may have the same or even improved activity compared to the pre-metabolic compound. Compounds and pharmaceutical compositions are desired that can be used for the treatment and prevention of disorders and conditions while even improving the effects associated with the administration of, for example, a pre-metabolic form of a compound or improving bioavailability characteristics and improving potential for immediate action and long-term treatment regimens.

SUMMARY

Provided herein are 4'-arylmethoxy isoindoline compounds, and pharmaceutically acceptable isotopologues, stereoisomers, salts, solvates (e.g., hydrates), prodrugs, clathrates, polymorphs, or co-crystals thereof.

In one embodiment, provided herein is a compound of Formula (I):

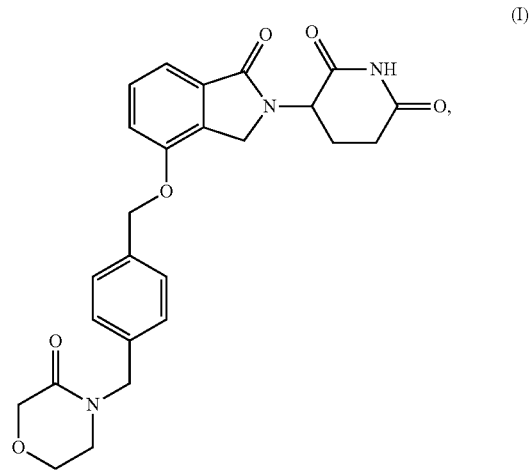 [SMILES: O=C1CCC(N2Cc3c(OCc4ccc(CN5CCOCC5=O)cc4)cccc3C2=O)C(=O)N1]

or an isotopologue thereof, or an enantiomer or a mixture of enantiomers thereof, or a pharmaceutically acceptable salt, solvate (e.g., hydrate), prodrug, clathrate, polymorph, or co-crystal thereof. The compound of Formula (I) is an active metabolite of 3-(4-((4-(morpholinomethyl)benzyl)oxy)-1-oxoisoindolin-2-yl)piperidine-2,6-dione mentioned above.

In one embodiment, provided herein is an isotopologue of a compound of Formula (I), or an enantiomer or a mixture of enantiomers thereof, or a pharmaceutically acceptable salt, solvate (e.g., hydrate), prodrug, clathrate, polymorph, or co-crystal thereof.

Also provided are methods of treating various diseases or disorders. The methods comprise administering to a patient in need of such treatment or management a therapeutically effective amount of a compound provided herein, or a pharmaceutically acceptable isotopologue, stereoisomer, salt, solvate (e.g., hydrate), prodrug, clathrate, polymorph, or co-crystal thereof.

Also provided are methods of managing various diseases and disorders, which comprise administering to a patient in need of such management a therapeutically effective amount of a compound provided herein, or a pharmaceutically acceptable isotopologue, stereoisomer, salt, solvate (e.g., hydrate), prodrug, clathrate, polymorph, or co-crystal thereof.

Also provided are methods of preventing various diseases and disorders, which comprise administering to a patient in need of such prevention a prophylactically effective amount of a compound provided herein, or a pharmaceutically acceptable isotopologue, stereoisomer, salt, solvate (e.g., hydrate), prodrug, clathrate, polymorph, or co-crystal thereof.

Also provided herein are combinations of the above methods.

Also provided herein are pharmaceutical compositions, single unit dosage forms, dosing regimens and kits which comprise a compound provided herein, or a pharmaceutically acceptable isotopologue, stereoisomer, salt, solvate (e.g., hydrate), prodrug, clathrate, polymorph, or co-crystal thereof.

Also provided herein are processes for the preparation of a compound provided herein, or a pharmaceutically acceptable isotopologue, stereoisomer, salt, solvate (e.g., hydrate), prodrug, clathrate, polymorph, or co-crystal thereof.

DETAILED DESCRIPTION

Figure 1:
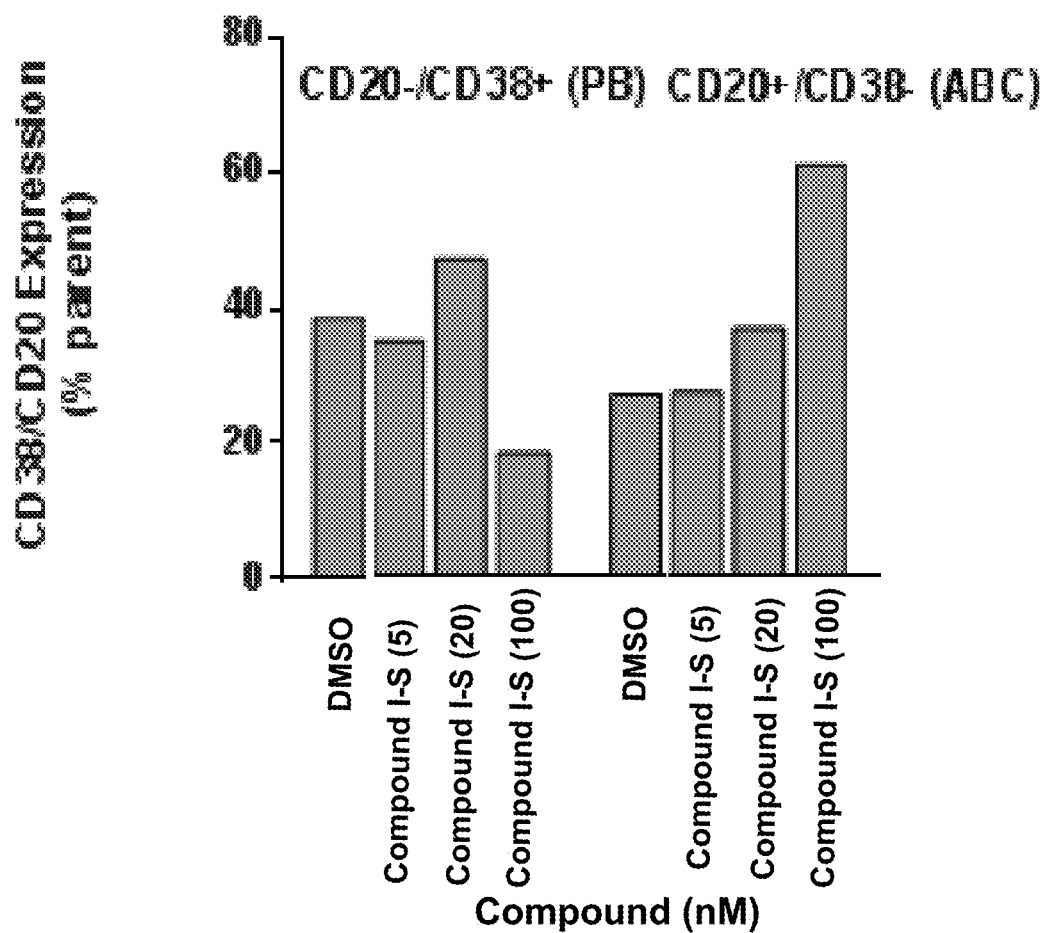
FIG. 1 shows effect of Compound I-S on plasmablast and activated B cell differentiation.

Unless defined otherwise, all technical and scientific terms used herein have the same meaning as those commonly understood by one of ordinary skill in the art. All publications and patents referred to herein are incorporated by reference herein in their entireties.

The descriptions of the terminology provided below apply to the terms as used herein and unless otherwise specified.

The term "compound" includes salts and solvates (e.g., hydrates) thereof.

The term "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. As used herein, an "isotopologue" is an isotopically enriched compound.

The term "isotopic enrichment" refers to the percentage of incorporation of an amount of a specific isotope at a given atom in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is higher than about 0.0156%.

The term "isotopic enrichment factor" refers to the ratio between the isotopic composition and the natural isotopic composition of a specified isotope.

With regard to the compounds provided herein, when a particular atomic position is designated as having deuterium or "D," it is understood that the abundance of deuterium at that position is substantially greater than the natural abundance of deuterium, which is about 0.0156%. A position designated as having deuterium typically has a minimum isotopic enrichment factor of, in certain embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium atom.

The isotopic enrichment and isotopic enrichment factor of the compounds provided herein can be determined using conventional analytical methods known to one of ordinary skill in the art, including mass spectrometry and nuclear magnetic resonance spectroscopy.

The term "pharmaceutically acceptable salt(s)" as used herein includes, but is not limited to, salts prepared from various inorganic and organic acids. The acids that can be used to prepare pharmaceutically acceptable acid addition salts of a basic compound are those that form non-toxic acid addition salts, i.e., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (i.e., 1,1'-methylene-bis-(2-hydroxy-3-naphthoate) acids, or isotopically enriched analogues thereof. Suitable inorganic acids include, but are not limited to, hydrochloric, hydrobromic, hydroiodic, sulfuric, phosphoric, or nitric acids, or isotopically enriched analogues thereof.

All of the compounds, functional groups and pharmaceutically acceptable salts provided herein may have one or more isotopically enriched hydrogen atom at one or more positions. Examples include, but are not limited to, isotopically enriched alcohols, carboxylic acids, and carboxylic acid esters.

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In certain embodiments, the complex or aggregate is in a crystalline form. In certain embodiments, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate. The term "co-crystal" as used herein refers to a crystalline structure composed of at least two components, where the components may be atoms, ions or molecules.

The term "polymorph" refers to solid crystalline forms of a compound or complex thereof. Different polymorphs of the same compound can exhibit different physical, chemical and spectroscopic properties.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "substantially free" when referring to a composition that is "substantially free" of a compound refers means that the composition contains no greater than about 20% by weight, no greater than about 10% by weight, no greater than about 5% by weight, no greater than about 3% by weight, no greater than about 1% by weight, no greater than about 0.5% by weight, no greater than about 0.2% by weight, no greater than about 0.1% by weight, no greater than about 0.01% by weight, no greater than about 0.001% by weight, or no greater than about 0.0001% by weight of the compound.

The term "substantially pure" when referring to a compound or composition means that the compound or composition has a purity of no less than about 80% by weight, no less than about 90% by weight, no less than about 95% by weight, no less than about 96% by weight, no less than about 97% by weight, no less than about 98% by weight, no less than about 99% by weight, no less than about 99.5% by weight, no less than about 99.9% by weight, no less than about 99.95% by weight, no less than about 99.99% by weight, no less than about 99.995% by weight, no less than about 99.999% by weight, no less than about 99.9995% by weight, or no less than about 99.9999% by weight.

The terms "process" as used herein refers to a method disclosed herein for a compound preparation. Modifications to the processes and methods disclosed herein (e.g., starting materials, reagents, protecting groups, solvents, temperatures, reaction times, and/or purification) that are well known to those of ordinary skill in the art are also encompassed by the disclosure.

The terms "adding," "reacting," "contacting" and "mixing" are used interchangeably to refer to contacting one reactant, reagent, solvent, catalyst, or a reactive group with another reactant, reagent, solvent, catalyst, or reactive group. Unless otherwise specified, reactants, reagents, solvents, catalysts, and reactive groups can be added individually, simultaneously, or separately, and/or can be added in any order. They can be added in the presence or absence of heat, and can optionally be added under an inert atmosphere (e.g., $N_2$ or Ar). In certain embodiments, the term "reacting" can also refer to in situ formation or intra-molecular reaction where the reactive groups are in the same molecule.

The term "substantially complete" when referring to a reaction means that the reaction contains no greater than about 50%, no greater than about 40%, no greater than about 30%, no greater than about 20%, no greater than about 10%, no greater than about 5%, no greater than about 4%, no greater than about 3%, no greater than about 2%, no greater than about 1%, no greater than about 0.5%, no greater than about 0.1%, or no greater than about 0.05% of a starting material left.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of a particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of a disease or disorder provided herein. The terms encompass the inhibition or reduction of a symptom of a particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread, or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease or one or more symptoms thereof.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, that provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or one or more symptoms thereof, or prevent the recurrence of the disease or disorder, or one or more symptoms thereof. A prophylactically effective amount of a compound means an amount of therapeutic agent, alone or in combination with other agents, that provides a prophylactic benefit in the prevention of the disease or disorder. The term "prophylactically effective amount" can encompass an amount that improves overall prophylaxis or enhances the prophylactic efficacy of another prophylactic agent.

Unless otherwise specified, the term "subject" is defined herein to include animals, such as mammals, including, but not limited to, primates (e.g., humans), cows, sheep, goats, horses, dogs, cats, rabbits, rats, mice, and the like. In specific embodiments, the subject is a human.

If the stereochemistry of a structure or a portion thereof is not indicated, e.g., with bold or dashed lines, the structure or portion thereof is to be interpreted as encompassing all stereoisomers of the structure.

Unless otherwise specified, to the extent that there is a discrepancy between a depicted chemical structure of a compound provided herein and a chemical name of a compound provided herein, the chemical structure shall control.

Compounds

Provided herein are 4'-arylmethoxy isoindoline compounds, and pharmaceutically acceptable isotopologues, stereoisomers, salts, solvates (e.g., hydrates), prodrugs, clathrates, polymorphs, or co-crystals thereof.

In one embodiment, provided herein is a compound of Formula (I) ("Compound I"):

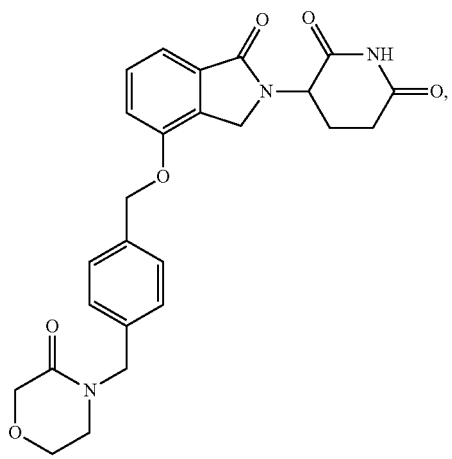

(I)

or an isotopologue thereof, or an enantiomer or a mixture of enantiomers thereof, or a pharmaceutically acceptable salt, solvate (e.g., hydrate), prodrug, clathrate, polymorph, or co-crystal thereof.

The compound of Formula (I) has a chemical name of 3-(1-oxo-4-((4-((3-oxomorpholino)methyl)benzyl)oxy) isoindolin-2-yl)piperidine-2,6-dione.

In one embodiment, the compound is (S)-3-(1-oxo-4-((4-((3-oxomorpholino)methyl)benzyl)oxy)isoindolin-2-yl)piperidine-2,6-dione ("Compound I-S"), or an isotopologue thereof, or a pharmaceutically acceptable salt, solvate (e.g., hydrate), prodrug, clathrate, polymorph, or co-crystal thereof. Compound I-S has a structure of Formula (I-S):

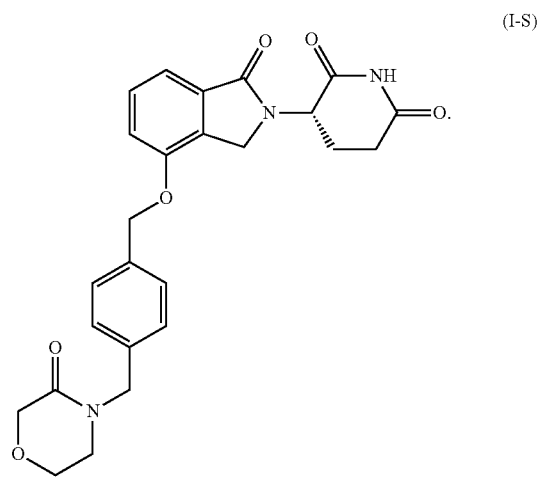 [SMILES: O=C1CC[C@H](N2Cc3c(OCc4ccc(CN5CCOCC5=O)cc4)cccc3C2=O)C(=O)N1]

(I-S)

In one embodiment, the compound is (R)-3-(1-oxo-4-((4-((3-oxomorpholino)methyl)benzyl)oxy)isoindolin-2-yl)piperidine-2,6-dione ("Compound I-R"), or an isotopologue thereof, or a pharmaceutically acceptable salt, solvate (e.g., hydrate), prodrug, clathrate, polymorph, or co-crystal thereof. Compound I-R has a structure of Formula (I-R):

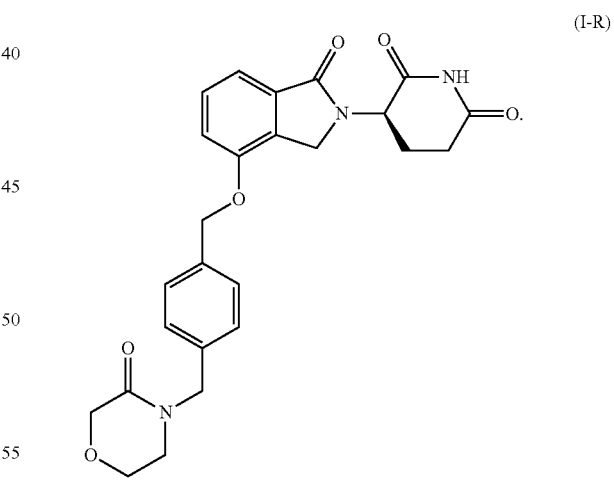

(I-R)

In one embodiment, provided herein is a substantially pure Compound I. In one embodiment, provided herein is a pharmaceutical composition comprising Compound I and one or more pharmaceutically acceptable excipients. In one embodiment, provided herein is a pharmaceutical composition comprising substantially pure Compound I and one or more pharmaceutically acceptable excipients. In one embodiment, provided herein is a solvate of Compound I. In one embodiment, provided herein is a hydrate of Compound I. In one embodiment, the hydrate is a mono-hydrate.

In one embodiment, provided herein is a substantially pure Compound I-S. In one embodiment, provided herein is a pharmaceutical composition comprising Compound I-S and one or more pharmaceutically acceptable excipients. In one embodiment, provided herein is a pharmaceutical composition comprising substantially pure Compound I-S and one or more pharmaceutically acceptable excipients. In one embodiment, provided herein is a solvate of Compound I-S. In one embodiment, provided herein is a hydrate of Compound I-S. In one embodiment, the hydrate is a monohydrate.

In one embodiment, provided herein is a substantially pure Compound I-R. In one embodiment, provided herein is a pharmaceutical composition comprising Compound I-R and one or more pharmaceutically acceptable excipients. In one embodiment, provided herein is a pharmaceutical composition comprising substantially pure Compound I-R and one or more pharmaceutically acceptable excipients. In one embodiment, provided herein is a solvate of Compound I-R. In one embodiment, provided herein is a hydrate of Compound I-R. In one embodiment, the hydrate is a monohydrate.

In one embodiment, provided herein is an isotopologue of a compound of Formula (I), or an enantiomer or a mixture of enantiomers thereof, or a pharmaceutically acceptable salt, solvate (e.g., hydrate), prodrug, clathrate, polymorph, or co-crystal thereof.

Isotopic enrichment (e.g., deuteration) of pharmaceuticals to improve pharmacokinetics ("PK"), pharmacodynamics ("PD"), and toxicity profiles, has been demonstrated previously with some classes of drugs. (See, e.g., Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999)).

Without being limited by a particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes may often result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In certain embodiments, the deuterium enrichment is performed on the site of C—H bond cleavage during metabolism.

Furthermore, racemization of many compounds involves the breaking of a C—H bond at the chiral center and may be retarded by selective incorporation of deuterium. Therefore, in certain embodiments, provided herein are isotopologues of a compound of Formula (I), or an enantiomer or a mixture of enantiomers thereof, or a pharmaceutically acceptable salt, solvate (e.g., hydrate), prodrug, clathrate, polymorph, or co-crystal thereof, in which racemization of the chiral center is retarded by selective incorporation of deuterium. In one embodiment, provided herein is selective incorporation of deuterium at the chrial center position of Formula (I).

In certain embodiments, provided herein are isotopologues of a compound of Formula (I), or an enantiomer or a mixture of enantiomers thereof, or a pharmaceutically acceptable salt, solvate (e.g., hydrate), prodrug, clathrate, polymorph, or co-crystal thereof, in which one or more atomic positions of the compound of Formula (I) is/are isotopically enriched with deuterium. In one embodiment, provided herein is a compound of Formula (II):

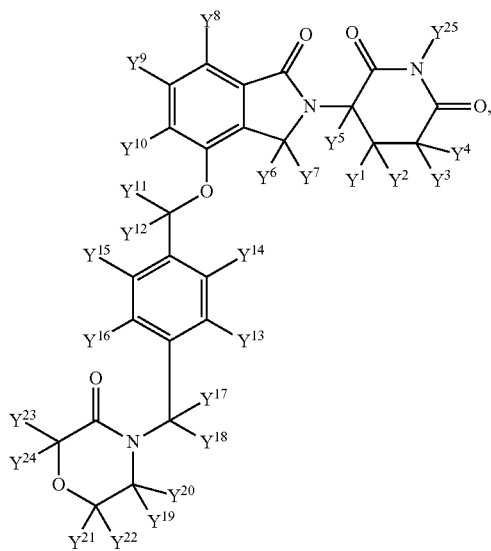

(II)

or an enantiomer or a mixture of enantiomers thereof, or a pharmaceutically acceptable salt, solvate (e.g., hydrate), prodrug, clathrate, polymorph, or co-crystal thereof, wherein one or more Y atoms (i.e., $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$) is/are hydrogen(s) isotopically enriched with deuterium, and any remaining Y atom(s) is/are non-enriched hydrogen atom(s). In certain embodiments, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or all of the indicated Y atoms is/are isotopically enriched with deuterium, and any remaining Y atom(s) is/are non-enriched hydrogen(s).

In one embodiment, $Y^{25}$ is a non-enriched hydrogen.

In one embodiment, the compound of Formula (II) is a compound of Formula (II-S):

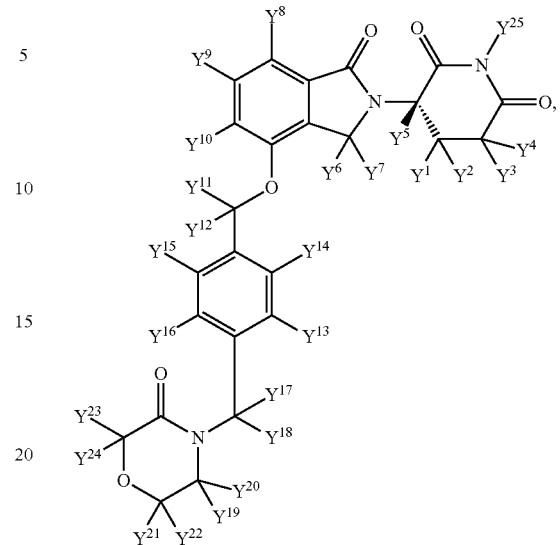

(II-S)

or a pharmaceutically acceptable salt, solvate (e.g., hydrate), prodrug, clathrate, polymorph, or co-crystal thereof.

In one embodiment, the compound of Formula (II) is a compound of Formula (II-R):

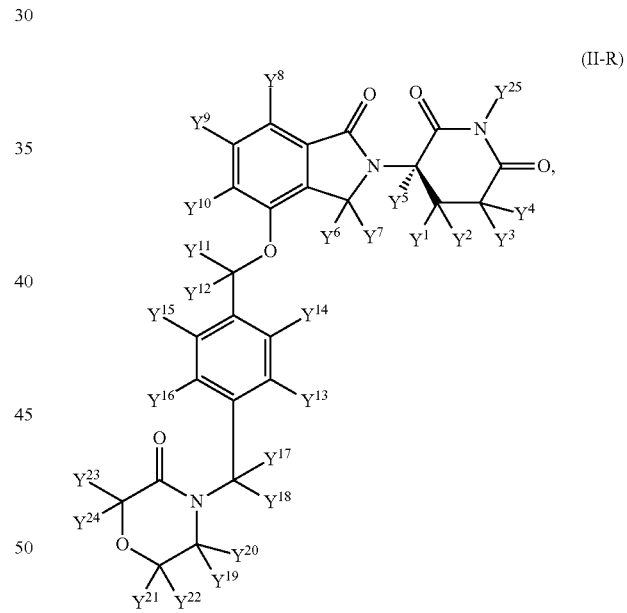

(II-R)

or a pharmaceutically acceptable salt, solvate (e.g., hydrate), prodrug, clathrate, polymorph, or co-crystal thereof.

In one embodiment, one of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ is a hydrogen that is isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, the deuterium-enriched atom is $Y^5$.

In one embodiment, two of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, three of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, four of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, five of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, six of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, seven of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, eight of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, nine of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, ten of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, eleven of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, twelve of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, thirteen of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, fourteen of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, fifteen of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, sixteen of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, seventeen of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, eighteen of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, nineteen of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, twenty of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, twenty one of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, twenty two of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, twenty three of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, twenty four of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are non-enriched hydrogen atoms. In one embodiment, one of the deuterium-enriched atoms is $Y^5$. In one embodiment, $Y^{25}$ is a non-enriched hydrogen.

In one embodiment, all of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$ are hydrogen atoms that are isotopically enriched with deuterium.

In one embodiment, provided herein is a compound of Formula (III):

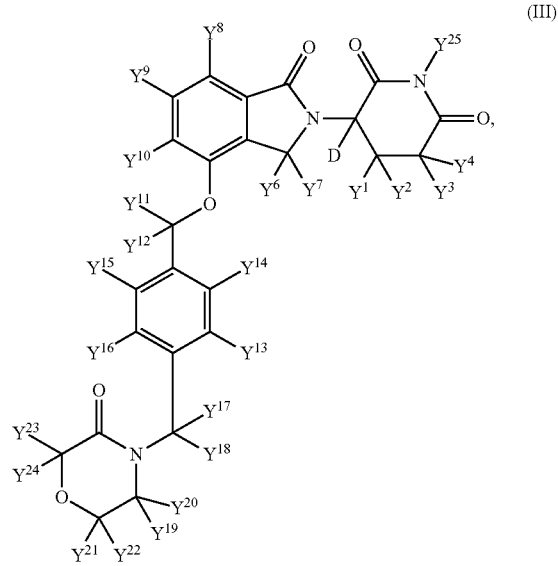

(III)

or an enantiomer or a mixture of enantiomers thereof, or a pharmaceutically acceptable salt, solvate (e.g., hydrate), prodrug, clathrate, polymorph, or co-crystal thereof, wherein one or more Y atoms (i.e., $Y^1$, $Y^2$, $Y^3$, $Y^4$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, and $Y^{25}$) is/are hydrogen(s) isotopically enriched with deuterium, and any remaining Y atom(s) is/are non-enriched hydrogen atom(s). In certain embodiments, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or all of the indicated Y atoms is/are isotopically enriched with deuterium, and any remaining Y atom(s) is/are non-enriched hydrogen(s).

In one embodiment, the compound of Formula (III) is a compound of Formula (III-S):

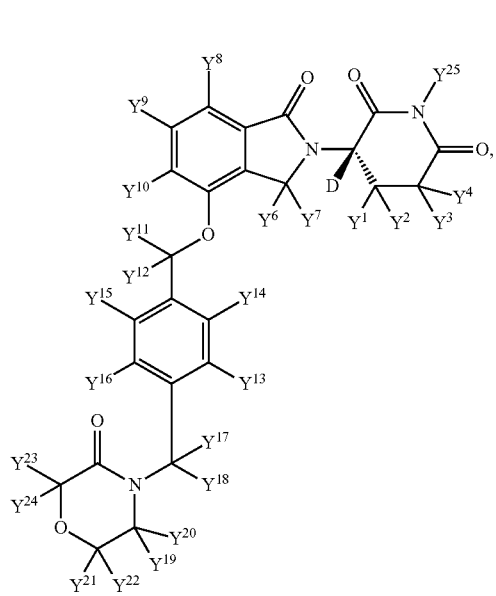

(III-S)

or a pharmaceutically acceptable salt, solvate (e.g., hydrate), prodrug, clathrate, polymorph, or co-crystal thereof.

In one embodiment, the compound of Formula (III) is a compound of Formula (III-R):

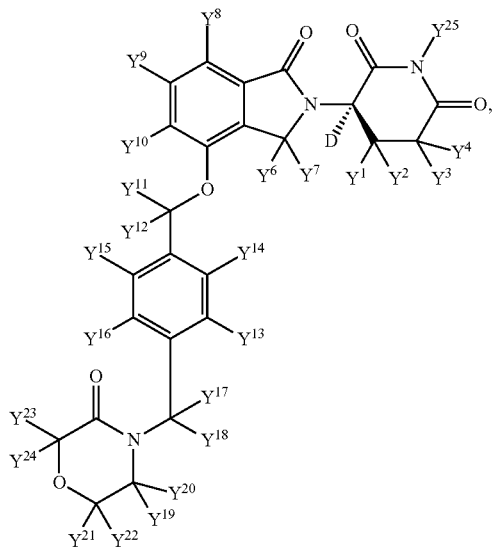

(III-R)

or a pharmaceutically acceptable salt, solvate (e.g., hydrate), prodrug, clathrate, polymorph, or co-crystal thereof.

In one embodiment, provided herein is a compound of Formula (IV):

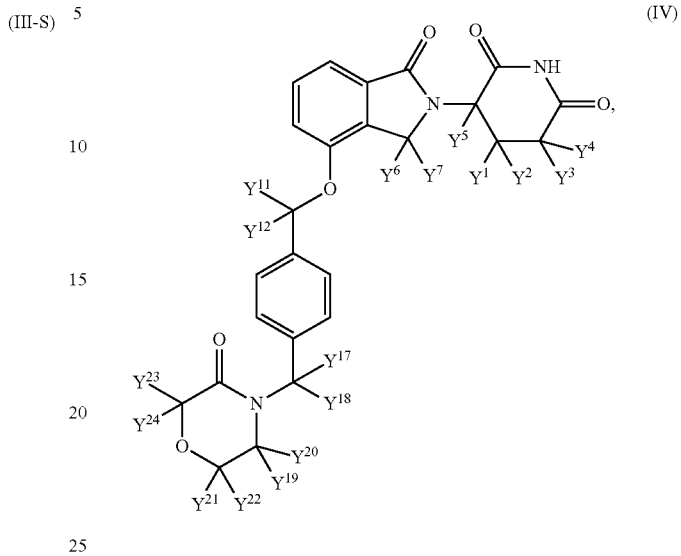

(IV)

or an enantiomer or a mixture of enantiomers thereof, or a pharmaceutically acceptable salt, solvate (e.g., hydrate), prodrug, clathrate, polymorph, or co-crystal thereof, wherein one or more Y atoms (i.e., $Y^1$, $Y^2$, $Y^3$, $Y^4$, $Y^5$, $Y^6$, $Y^7$, $Y^{11}$, $Y^{12}$, $Y^{17}$, $Y^{18}$, $Y^{19}$, $Y^{20}$, $Y^{21}$, $Y^{22}$, $Y^{23}$, and $Y^{24}$) is/are hydrogen(s) isotopically enriched with deuterium, and any remaining Y atom(s) is/are non-enriched hydrogen atom(s). In certain embodiments, one, two, three, four, five, six, seven, eight, nine, ten, eleven, twelve, thirteen, fourteen, fifteen, sixteen, or all of the indicated Y atoms is/are isotopically enriched with deuterium, and any remaining Y atom(s) is/are non-enriched hydrogen(s).

In one embodiment, the compound of Formula (IV) is a compound of Formula (IV-S):

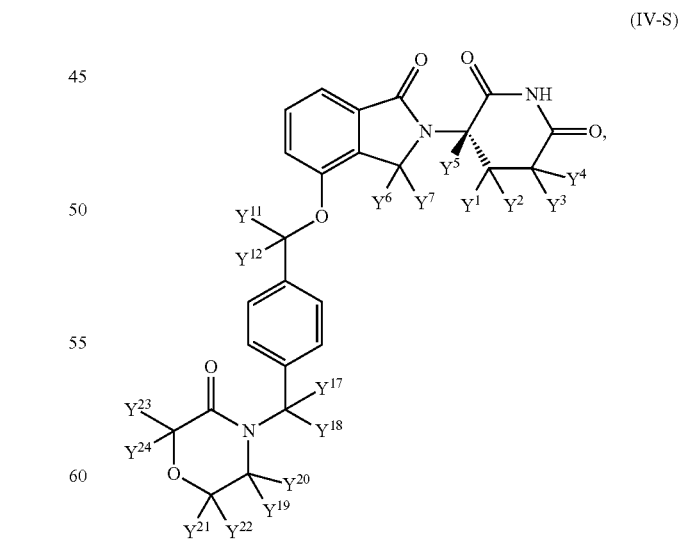

(IV-S)

or a pharmaceutically acceptable salt, solvate (e.g., hydrate), prodrug, clathrate, polymorph, or co-crystal thereof.

In one embodiment, the compound of Formula (IV) is a compound of Formula (IV-R):

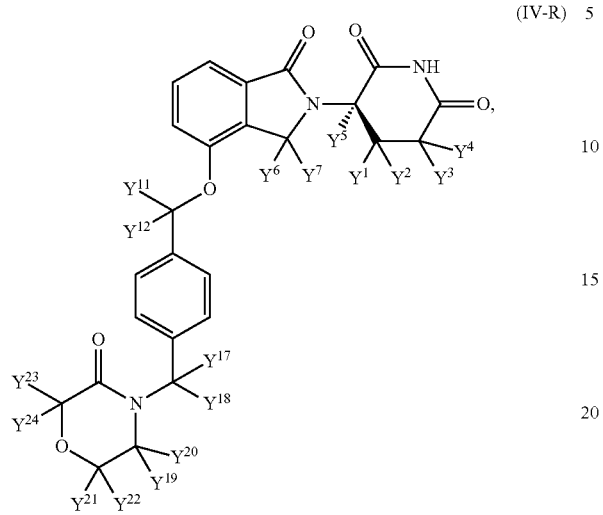

(IV-R)

or a pharmaceutically acceptable salt, solvate (e.g., hydrate), prodrug, clathrate, polymorph, or co-crystal thereof.

In certain embodiments, one or more Y atoms on the glutarimide portion of Compound II are deuterium-enriched. In certain embodiments, one or more Y atoms on the isoindolinone portion of Compound II are deuterium-enriched. In certain embodiments, one or more Y atoms on both the glutarimide portion and the isoindolinone portion of Compound II are deuterium-enriched, i.e., any combination of deuteration shown above for the glutarimide portion and the isoindolinone portion is encompassed. For example, particular compounds provided herein include the following listed compounds in Tables 1-4, or an enantiomer or a mixture of enantiomers thereof; in which the label "D" indicates a deuterium-enriched atomic position, i.e., a sample comprising the given compound has a deuterium enrichment at the indicated position(s) above the natural abundance of deuterium.

TABLE 1

Deuterium enriched compounds of formula (II):

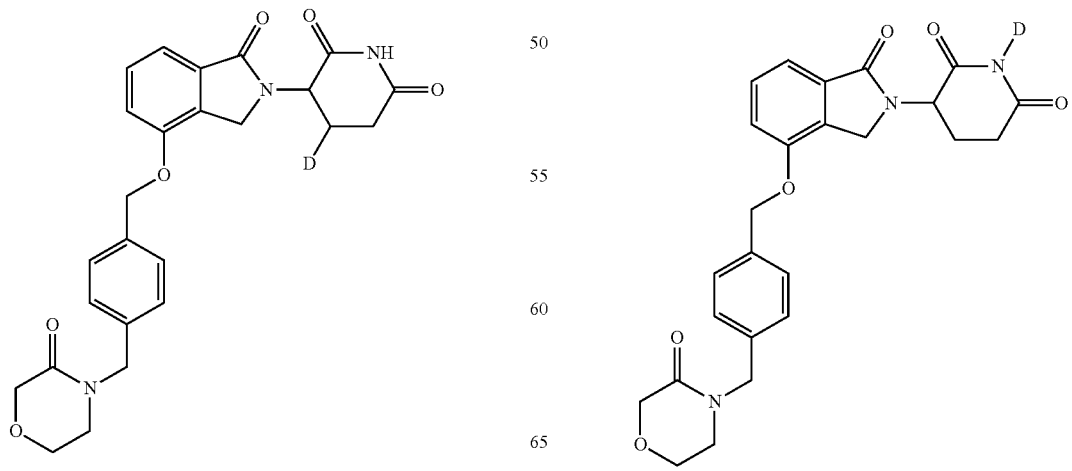

TABLE 1-continued

Deuterium enriched compounds of formula (II):

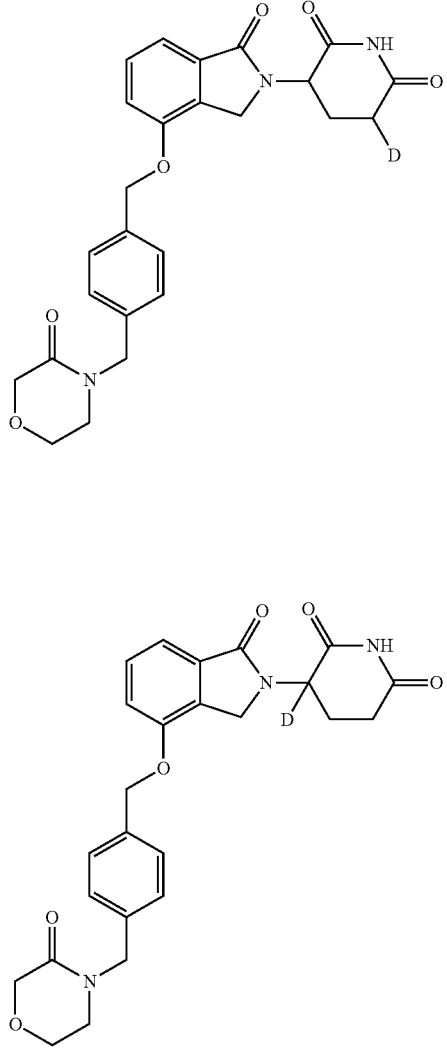

TABLE 1-continued
Deuterium enriched compounds of formula (II):
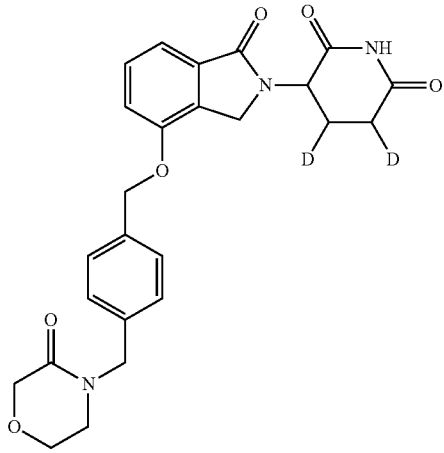 [SMILES: [2H]C1C(=O)NC(=O)C(N2Cc3c(OCc4ccc(CN5CCOCC5=O)cc4)cccc3C2=O)C1[2H]]
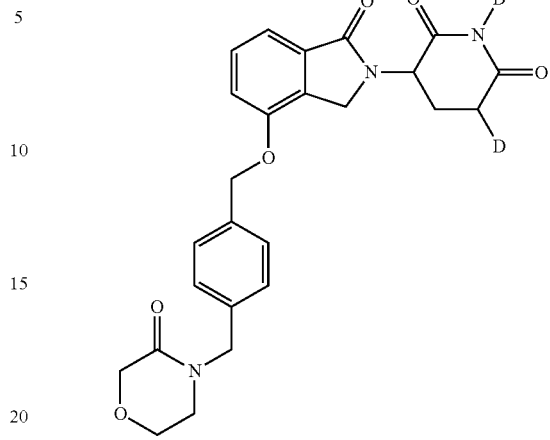
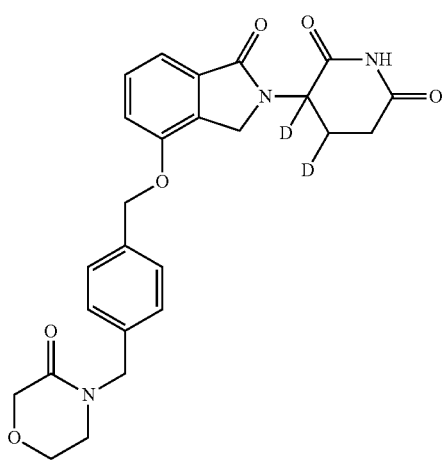 [SMILES: [2H]C1CC(=O)NC(=O)C1([2H])N1Cc2c(OCc3ccc(CN4CCOCC4=O)cc3)cccc2C1=O]
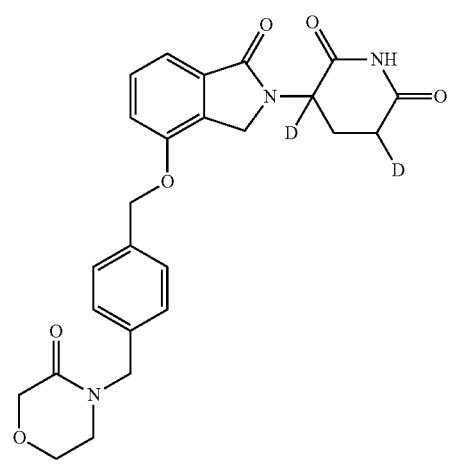
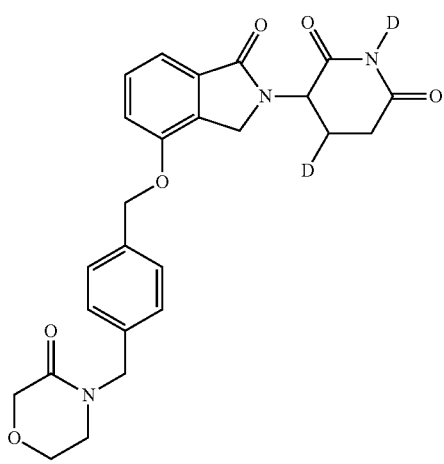
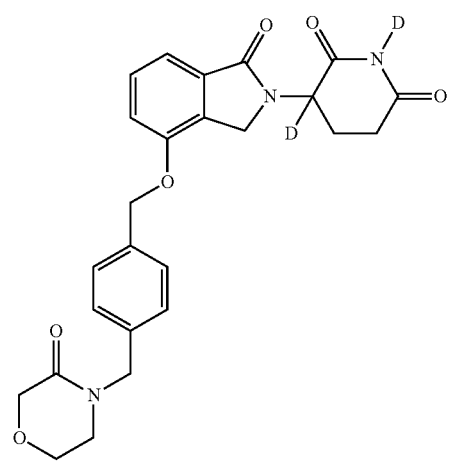

TABLE 1-continued
Deuterium enriched compounds of formula (II):
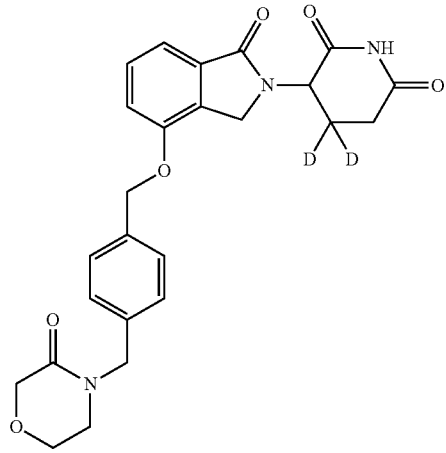 [SMILES: [2H]C1([2H])CC(=O)NC(=O)C1N1Cc2c(OCc3ccc(CN4CCOCC4=O)cc3)cccc2C1=O]
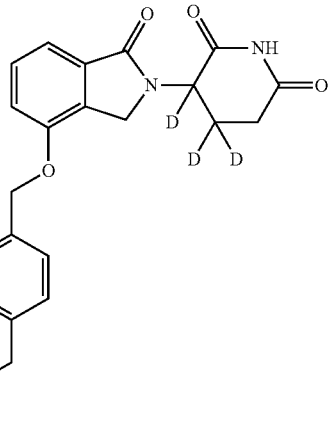
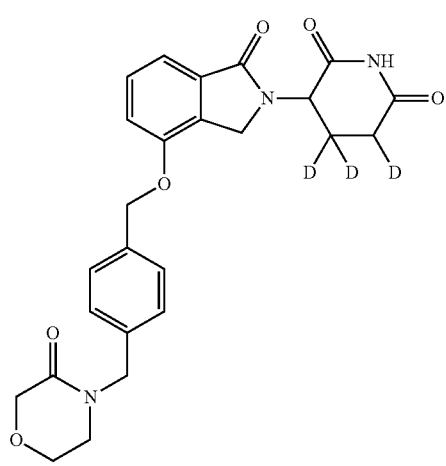 [SMILES: [2H]C1C(=O)NC(=O)C(N2Cc3c(OCc4ccc(CN5CCOCC5=O)cc4)cccc3C2=O)C1([2H])[2H]]
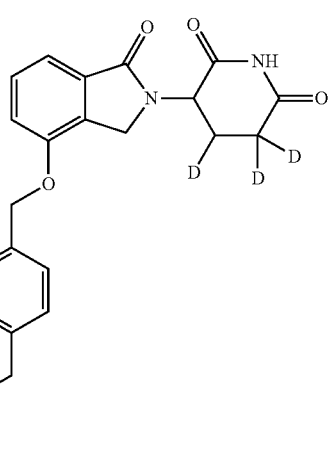

TABLE 1-continued
Deuterium enriched compounds of formula (II):
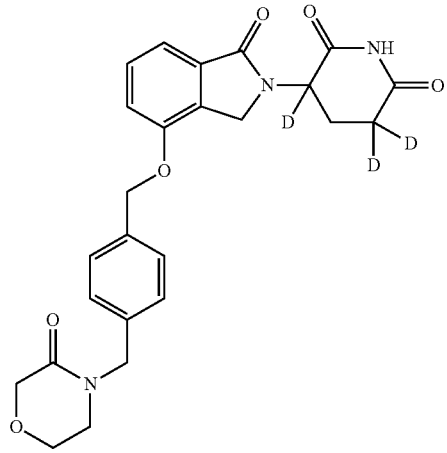 [SMILES: [2H]C1([2H])CC([2H])(N2Cc3c(OCc4ccc(CN5CCOCC5=O)cc4)cccc3C2=O)C(=O)NC1=O]
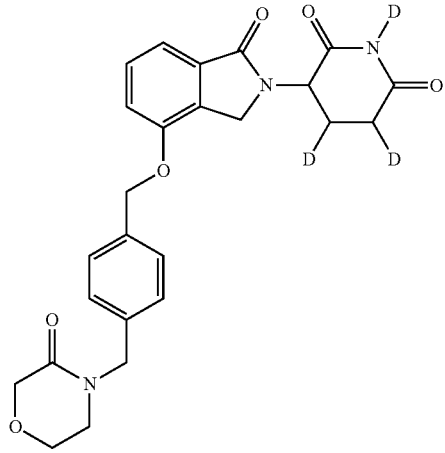
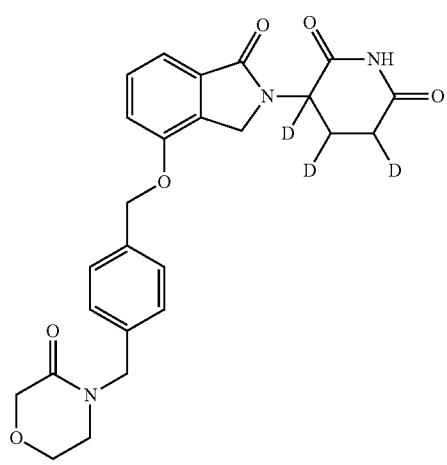 [SMILES: [2H]C1C(=O)NC(=O)C([2H])(N2Cc3c(OCc4ccc(CN5CCOCC5=O)cc4)cccc3C2=O)C1[2H]]

TABLE 1-continued
Deuterium enriched compounds of formula (II):
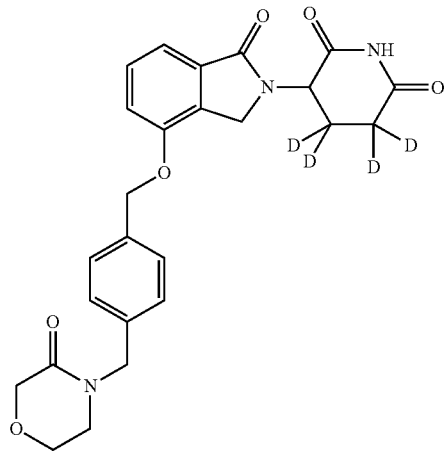 [SMILES: [2H]C1([2H])C(=O)NC(=O)C(N2Cc3c(OCc4ccc(CN5CCOCC5=O)cc4)cccc3C2=O)C1([2H])[2H]]
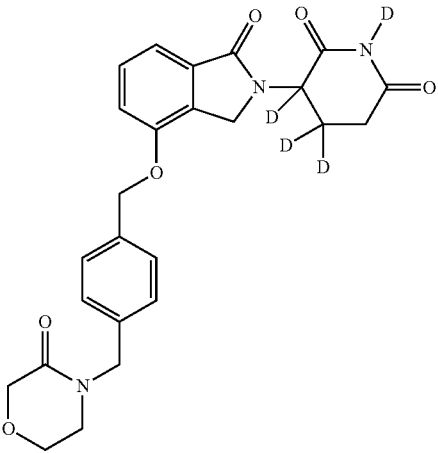
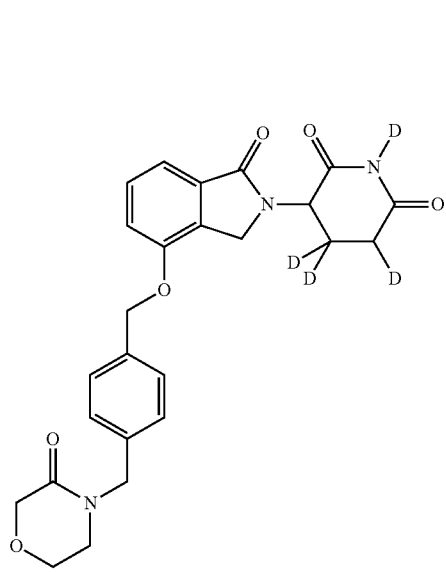
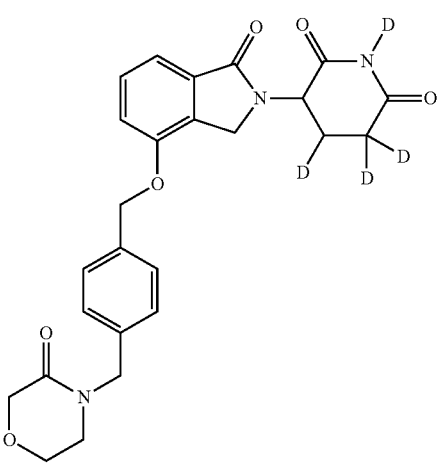

TABLE 1-continued
Deuterium enriched compounds of formula (II):
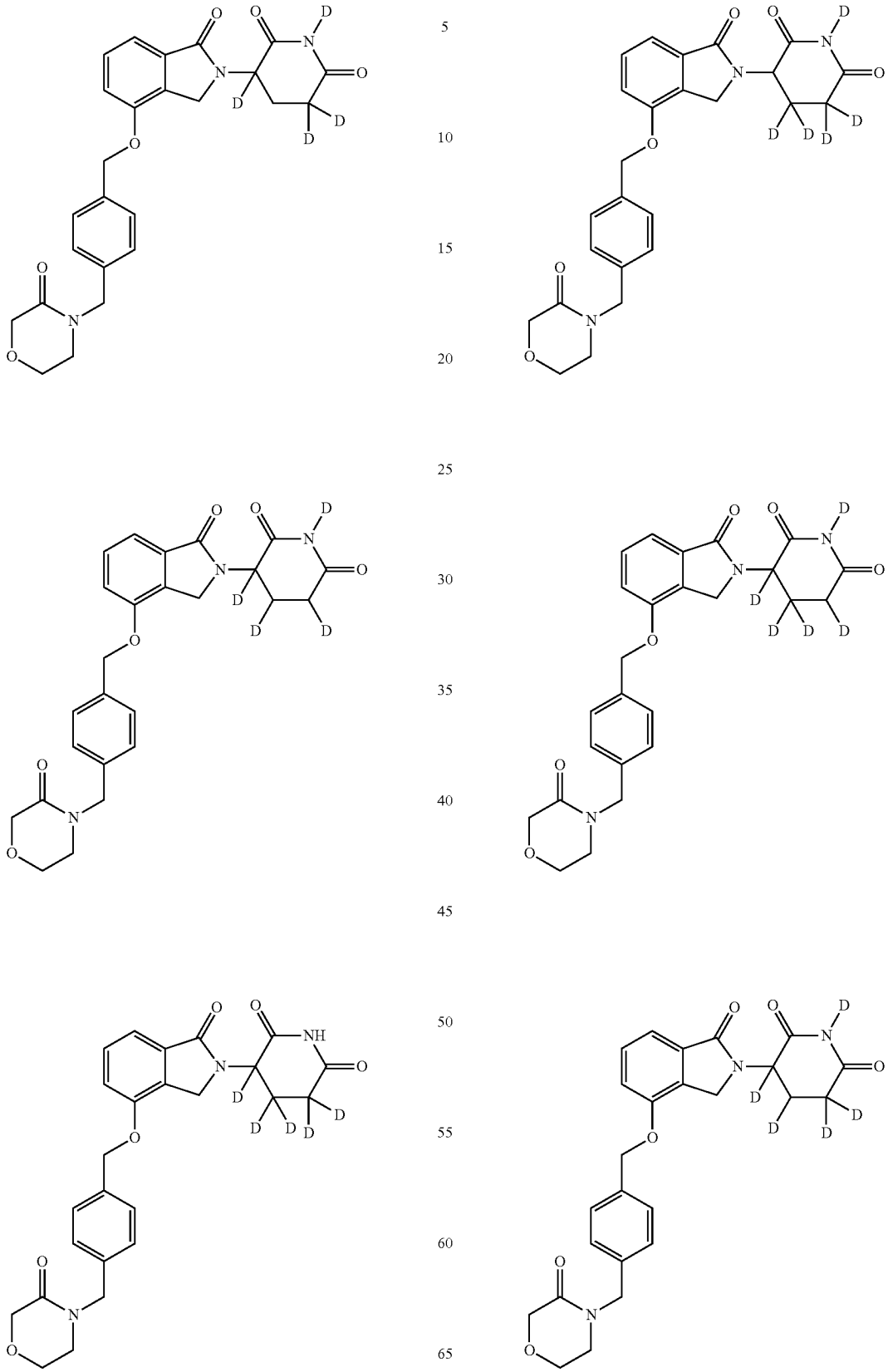

TABLE 1-continued
Deuterium enriched compounds of formula (II):
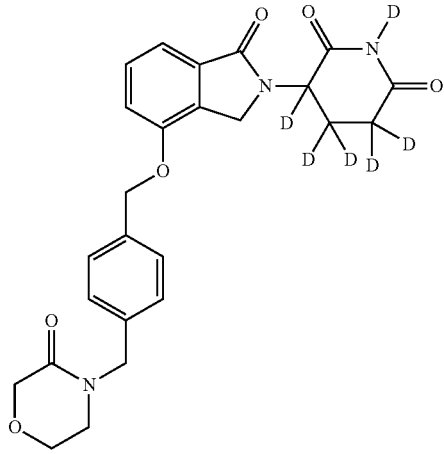
TABLE 2
Deuterium enriched compounds of formula (II):
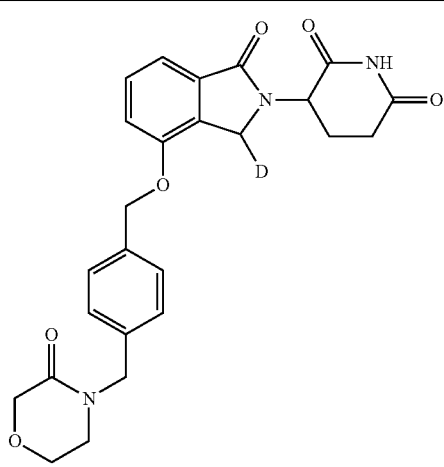
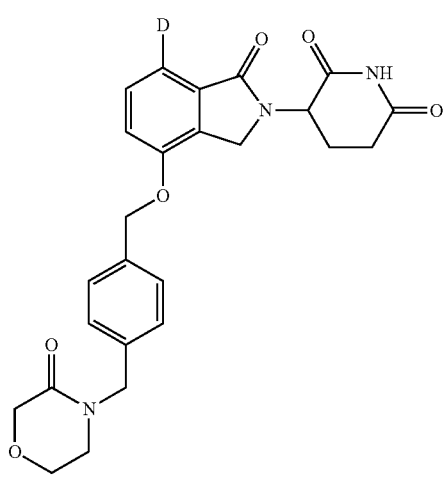 [SMILES: [2H]c1ccc(OCc2ccc(CN3CCOCC3=O)cc2)c2c1C(=O)N(C1CCC(=O)NC1=O)C2]
TABLE 2-continued
Deuterium enriched compounds of formula (II):
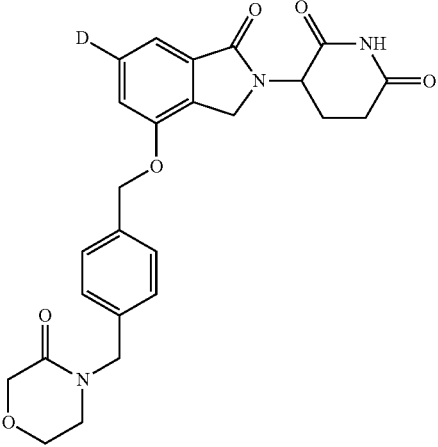 [SMILES: [2H]c1cc(OCc2ccc(CN3CCOCC3=O)cc2)c2c(c1)C(=O)N(C1CCC(=O)NC1=O)C2]
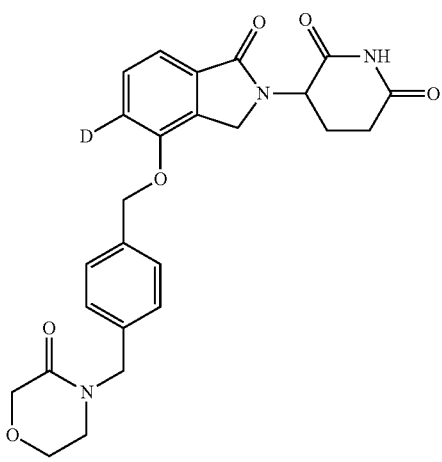 [SMILES: [2H]c1ccc2c(c1OCc1ccc(CN3CCOCC3=O)cc1)CN(C1CCC(=O)NC1=O)C2=O]
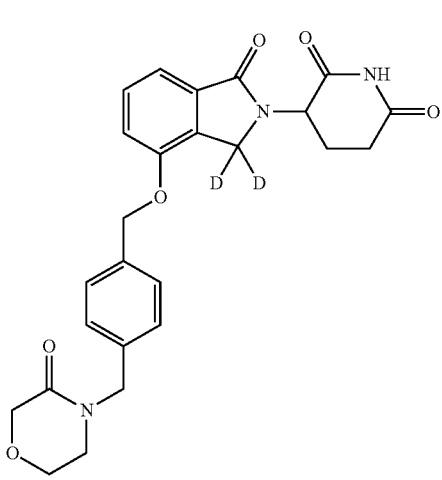 [SMILES: [2H]C1([2H])c2c(OCc3ccc(CN4CCOCC4=O)cc3)cccc2C(=O)N1C1CCC(=O)NC1=O]

TABLE 2-continued
Deuterium enriched compounds of formula (II):
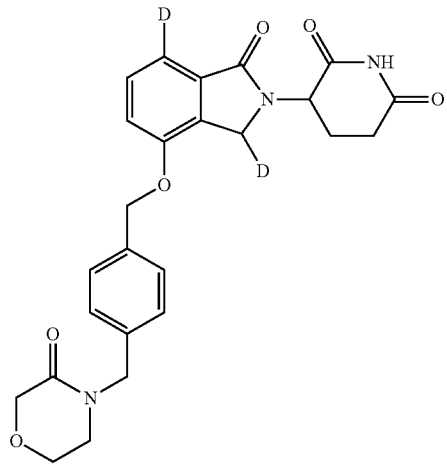 [SMILES: [2H]c1ccc(OCc2ccc(CN3CCOCC3=O)cc2)c2c1C(=O)N(C1CCC(=O)NC1=O)C2[2H]]
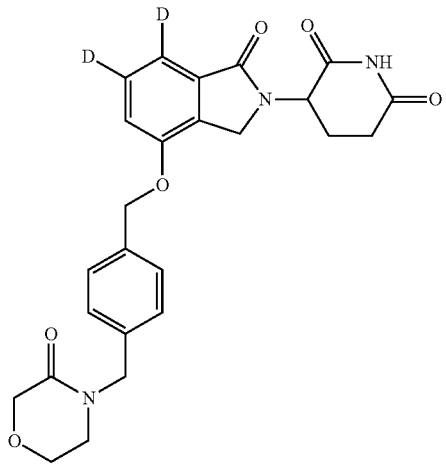
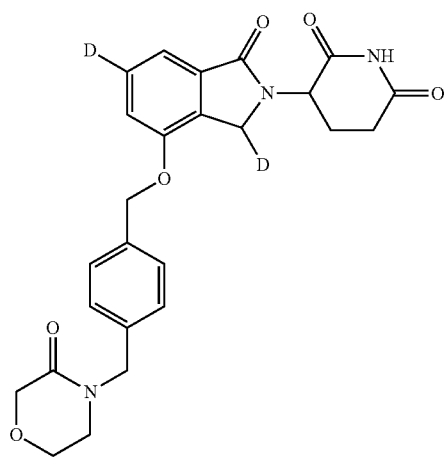 [SMILES: [2H]c1cc(OCc2ccc(CN3CCOCC3=O)cc2)c2c(c1)C(=O)N(C1CCC(=O)NC1=O)C2[2H]]
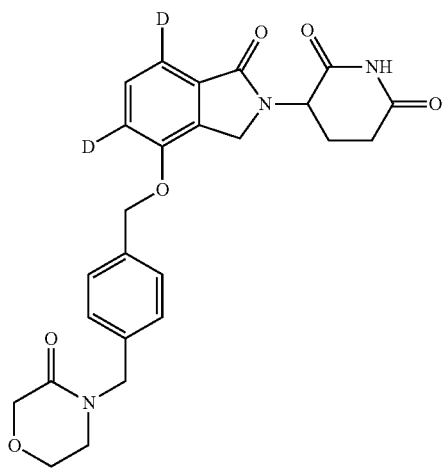
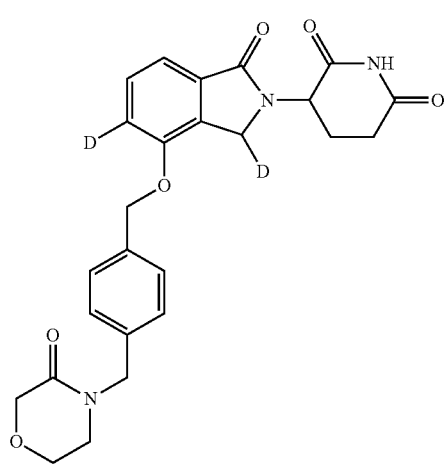 [SMILES: [2H]c1ccc2c(c1OCc1ccc(CN3CCOCC3=O)cc1)C([2H])N(C1CCC(=O)NC1=O)C2=O]
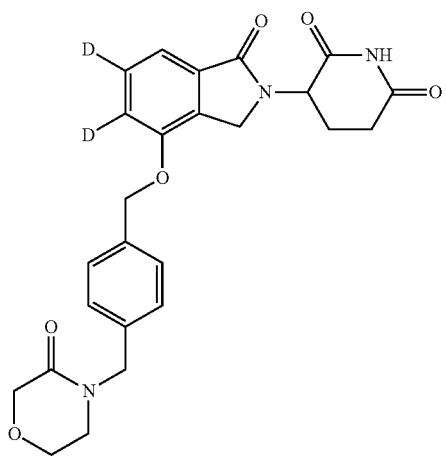 [SMILES: [2H]c1cc2c(c(OCc3ccc(CN4CCOCC4=O)cc3)c1[2H])CN(C1CCC(=O)NC1=O)C2=O]

TABLE 2-continued
Deuterium enriched compounds of formula (II):
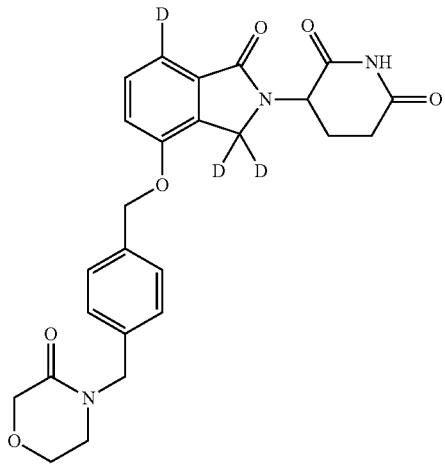 [SMILES: [2H]c1ccc(OCc2ccc(CN3CCOCC3=O)cc2)c2c1C(=O)N(C1CCC(=O)NC1=O)C2([2H])[2H]]
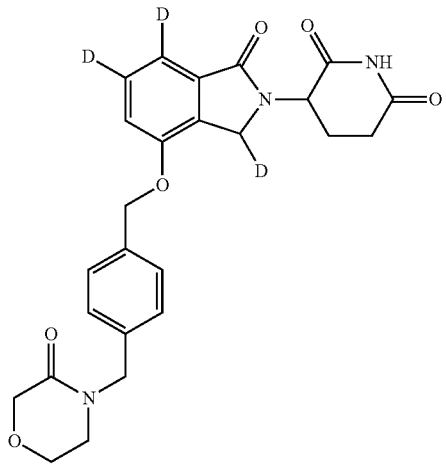
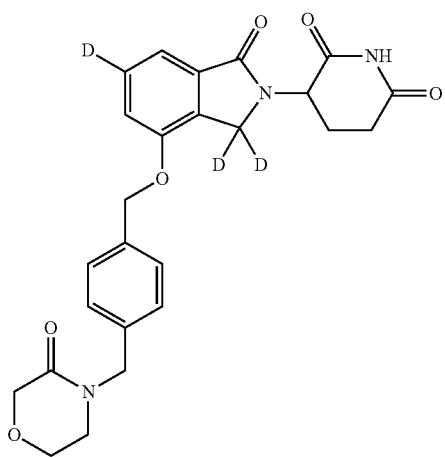 [SMILES: [2H]c1cc(OCc2ccc(CN3CCOCC3=O)cc2)c2c(c1)C(=O)N(C1CCC(=O)NC1=O)C2([2H])[2H]]
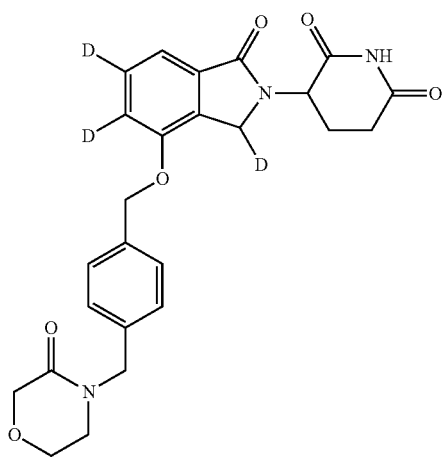
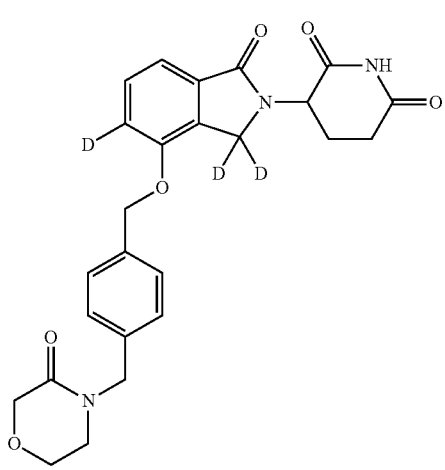 [SMILES: [2H]c1ccc2c(c1OCc1ccc(CN3CCOCC3=O)cc1)C([2H])([2H])N(C1CCC(=O)NC1=O)C2=O]
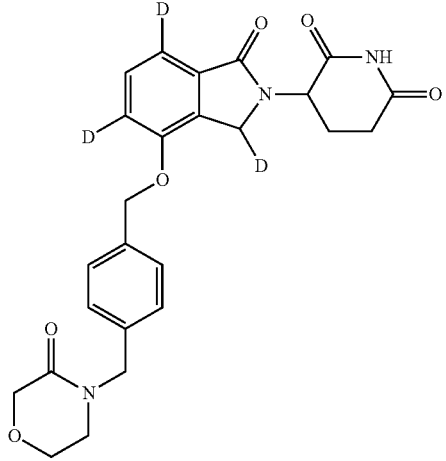 [SMILES: [2H]c1cc([2H])c2c(c1OCc1ccc(CN3CCOCC3=O)cc1)C([2H])N(C1CCC(=O)NC1=O)C2=O]

TABLE 2-continued
Deuterium enriched compounds of formula (II):
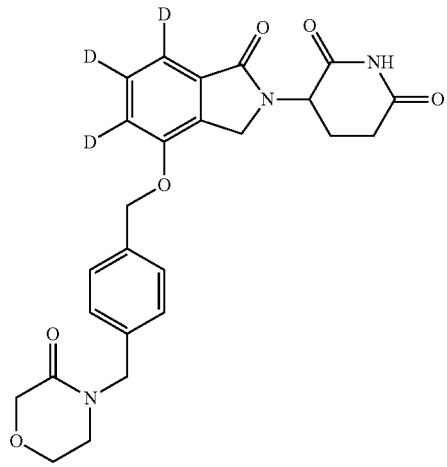 [SMILES: [2H]c1c([2H])c(OCc2ccc(CN3CCOCC3=O)cc2)c2c(c1[2H])C(=O)N(C1CCC(=O)NC1=O)C2]
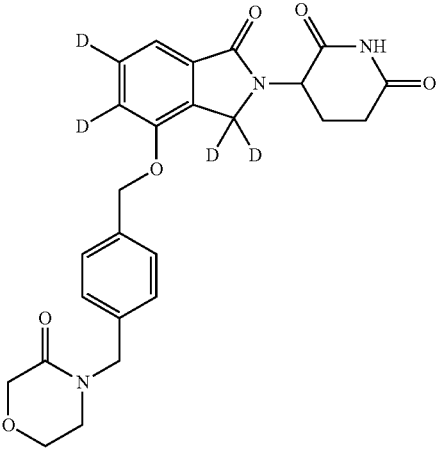
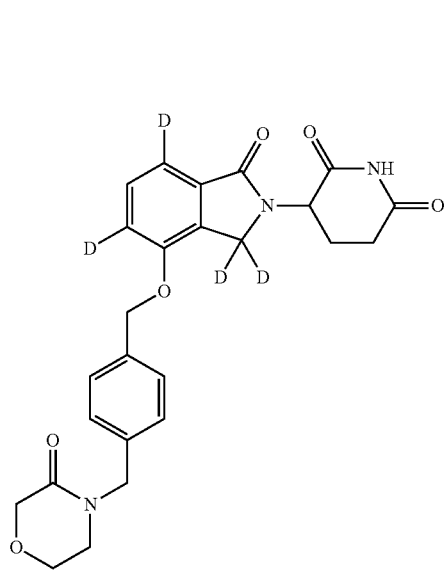 [SMILES: [2H]c1cc([2H])c2c(c1OCc1ccc(CN3CCOCC3=O)cc1)C([2H])([2H])N(C1CCC(=O)NC1=O)C2=O]
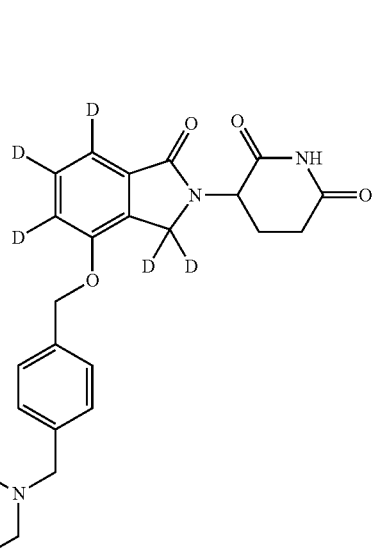

TABLE 3
Deuterium enriched compounds of formula (II):
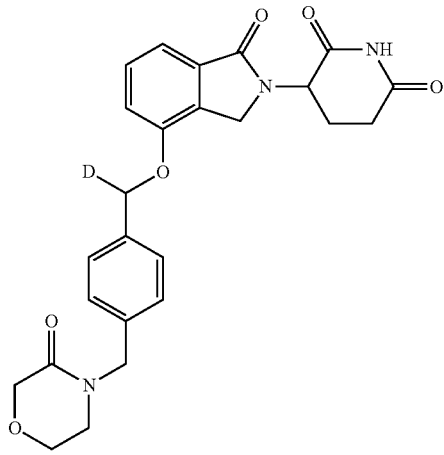 [SMILES: [2H]C(Oc1cccc2c1CN(C1CCC(=O)NC1=O)C2=O)c1ccc(CN2CCOCC2=O)cc1]
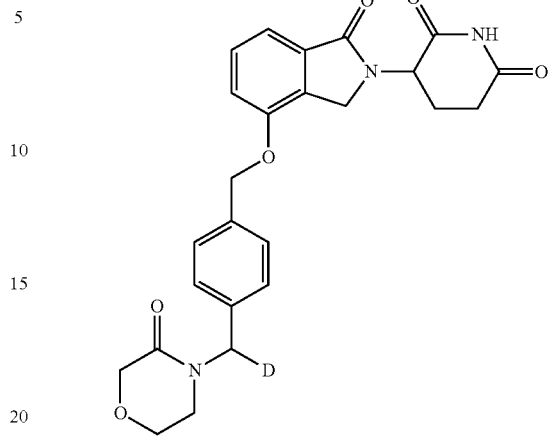
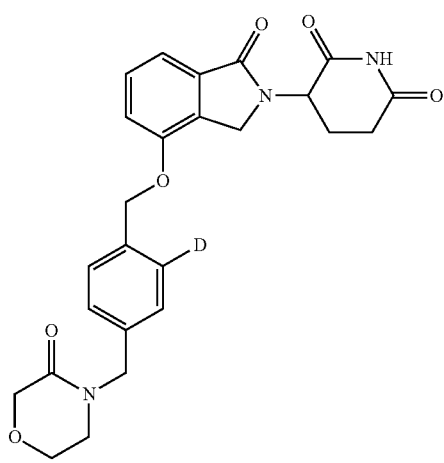 [SMILES: [2H]c1cc(CN2CCOCC2=O)ccc1COc1cccc2c1CN(C1CCC(=O)NC1=O)C2=O]
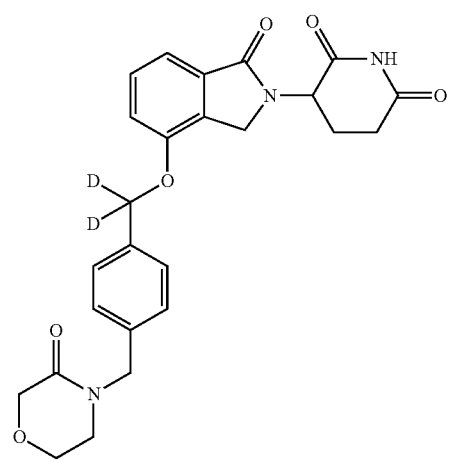
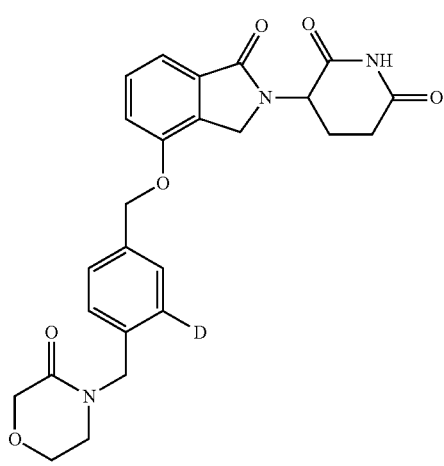 [SMILES: [2H]c1cc(COc2cccc3c2CN(C2CCC(=O)NC2=O)C3=O)ccc1CN1CCOCC1=O]
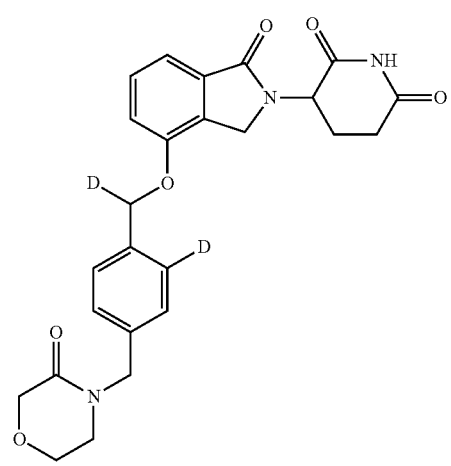 [SMILES: [2H]c1cc(CN2CCOCC2=O)ccc1C([2H])Oc1cccc2c1CN(C1CCC(=O)NC1=O)C2=O]

TABLE 3-continued
Deuterium enriched compounds of formula (II):
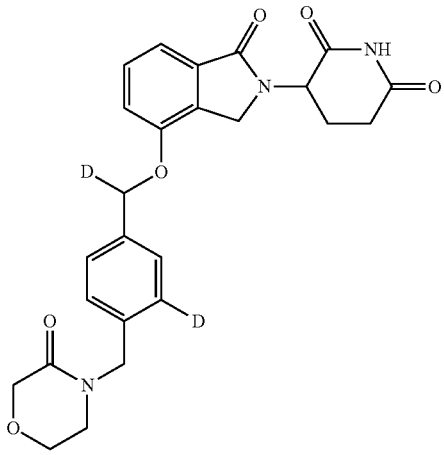 [SMILES: [2H]c1cc(C([2H])Oc2cccc3c2CN(C2CCC(=O)NC2=O)C3=O)ccc1CN1CCOCC1=O]
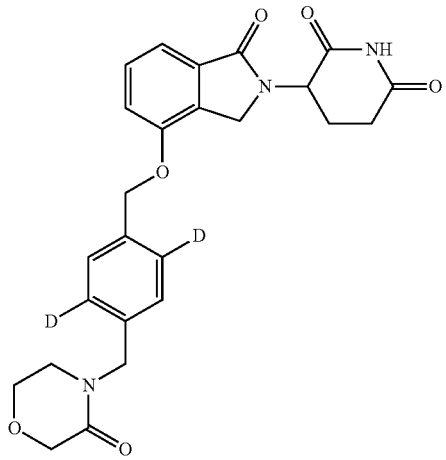
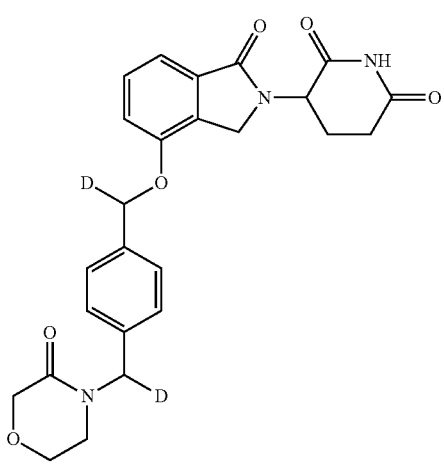 [SMILES: [2H]C(Oc1cccc2c1CN(C1CCC(=O)NC1=O)C2=O)c1ccc(C([2H])N2CCOCC2=O)cc1]
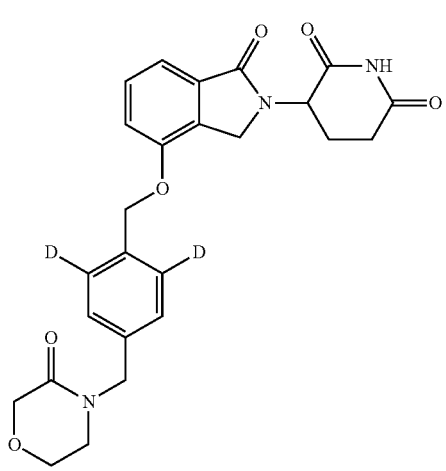
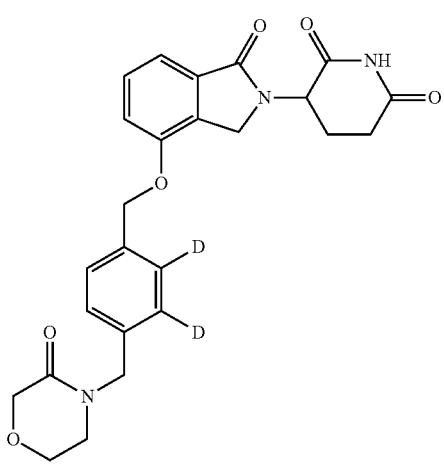 [SMILES: [2H]c1c(COc2cccc3c2CN(C2CCC(=O)NC2=O)C3=O)ccc(CN2CCOCC2=O)c1[2H]]
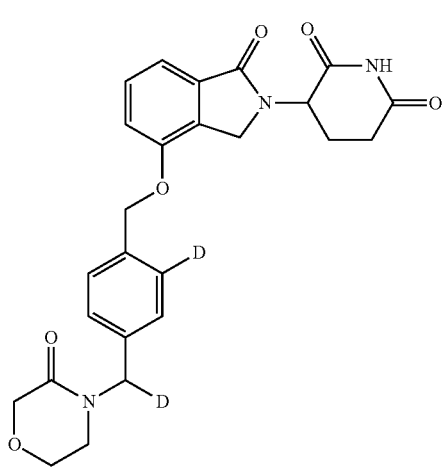 [SMILES: [2H]c1cc(C([2H])N2CCOCC2=O)ccc1COc1cccc2c1CN(C1CCC(=O)NC1=O)C2=O]

TABLE 3-continued
Deuterium enriched compounds of formula (II):
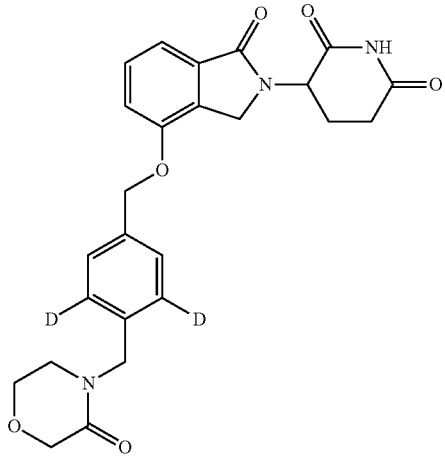 [SMILES: [2H]c1cc(COc2cccc3c2CN(C2CCC(=O)NC2=O)C3=O)cc([2H])c1CN1CCOCC1=O]
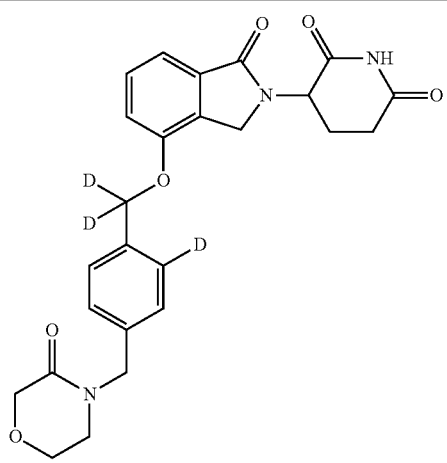
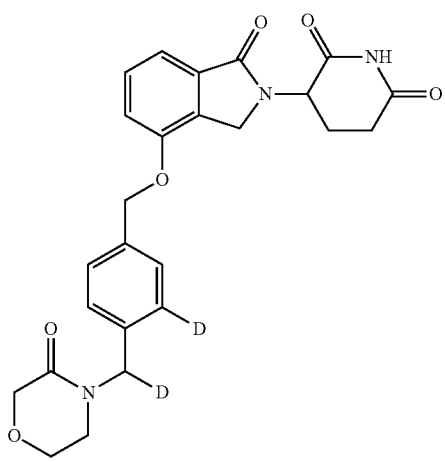 [SMILES: [2H]c1cc(COc2cccc3c2CN(C2CCC(=O)NC2=O)C3=O)ccc1C([2H])N1CCOCC1=O]
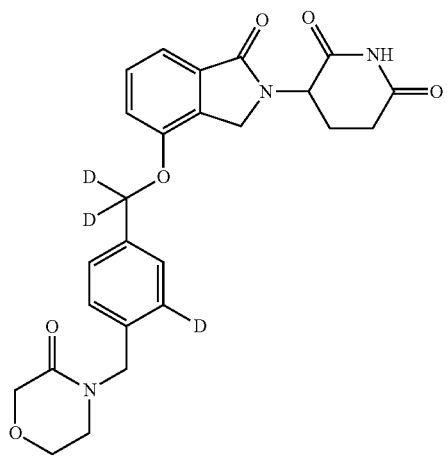
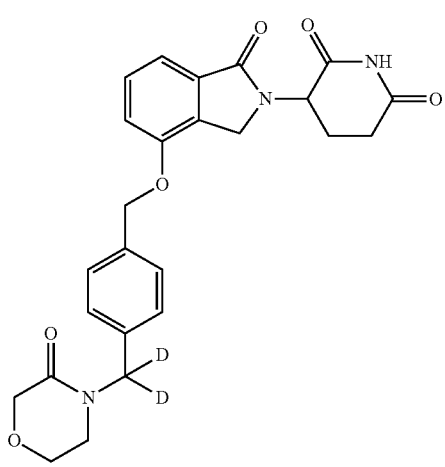 [SMILES: [2H]C([2H])(c1ccc(COc2cccc3c2CN(C2CCC(=O)NC2=O)C3=O)cc1)N1CCOCC1=O]
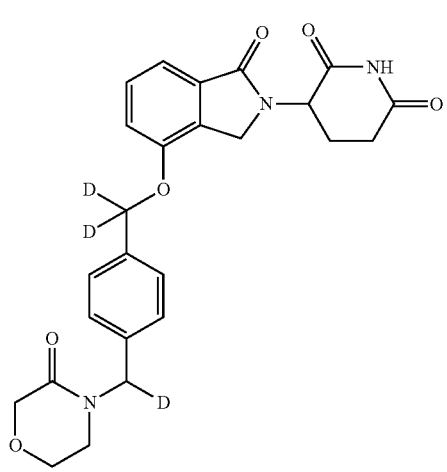 [SMILES: [2H]C(c1ccc(C([2H])([2H])Oc2cccc3c2CN(C2CCC(=O)NC2=O)C3=O)cc1)N1CCOCC1=O]

TABLE 3-continued
Deuterium enriched compounds of formula (II):
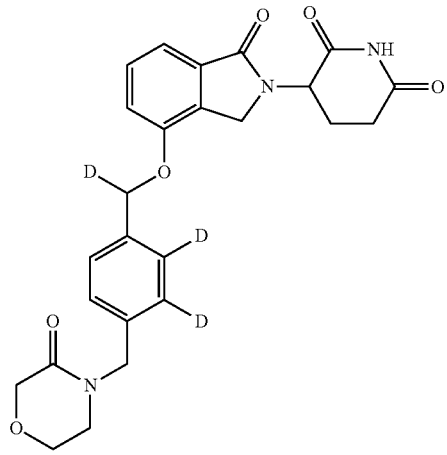 [SMILES: [2H]c1c(CN2CCOCC2=O)ccc(C([2H])Oc2cccc3c2CN(C2CCC(=O)NC2=O)C3=O)c1[2H]]
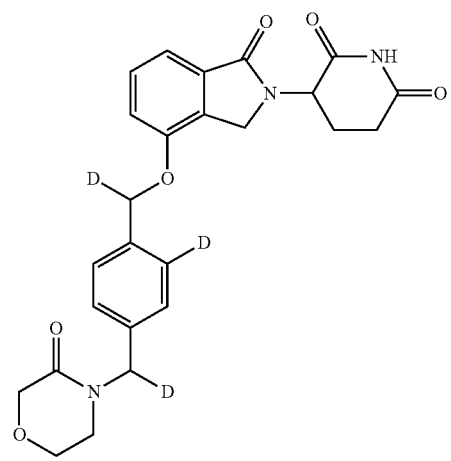
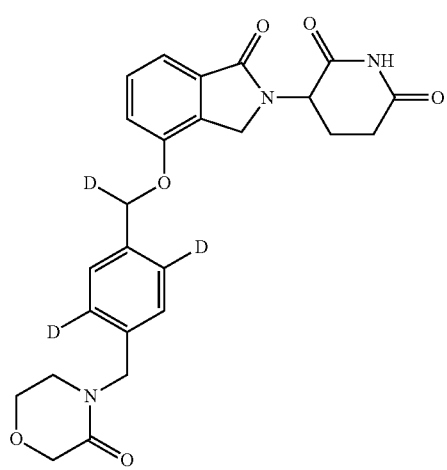 [SMILES: [2H]c1cc(C([2H])Oc2cccc3c2CN(C2CCC(=O)NC2=O)C3=O)c([2H])cc1CN1CCOCC1=O]
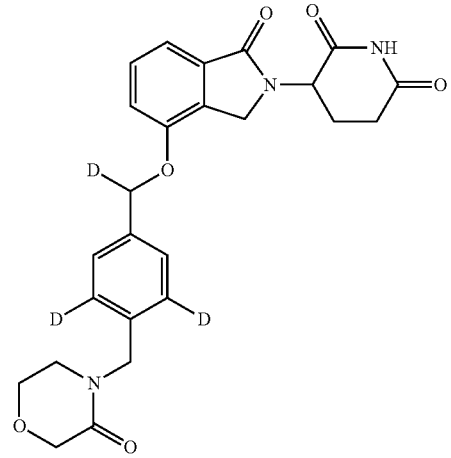
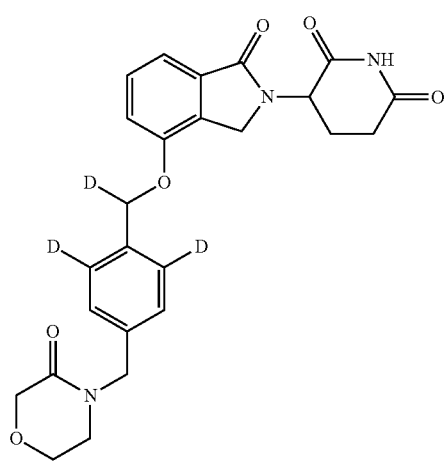 [SMILES: [2H]c1cc(CN2CCOCC2=O)cc([2H])c1C([2H])Oc1cccc2c1CN(C1CCC(=O)NC1=O)C2=O]
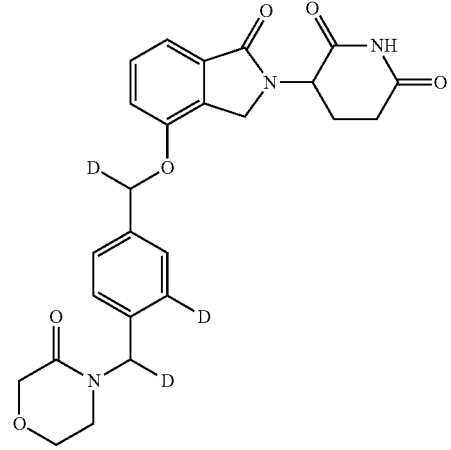 [SMILES: [2H]c1cc(C([2H])Oc2cccc3c2CN(C2CCC(=O)NC2=O)C3=O)ccc1C([2H])N1CCOCC1=O]

TABLE 3-continued
Deuterium enriched compounds of formula (II):
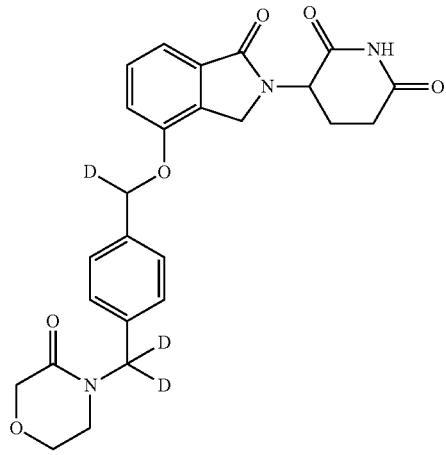 [SMILES: [2H]C(Oc1cccc2c1CN(C1CCC(=O)NC1=O)C2=O)c1ccc(C([2H])([2H])N2CCOCC2=O)cc1]
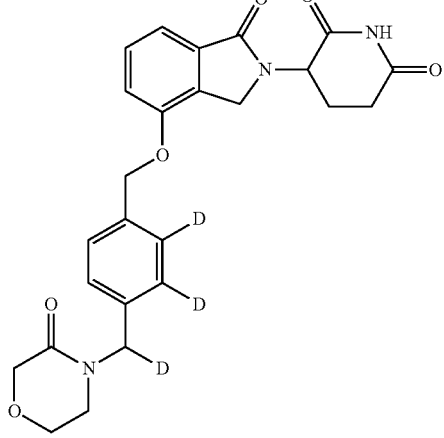
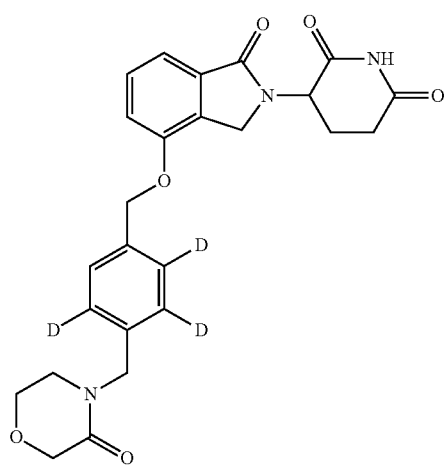 [SMILES: [2H]c1cc(COc2cccc3c2CN(C2CCC(=O)NC2=O)C3=O)c([2H])c([2H])c1CN1CCOCC1=O]
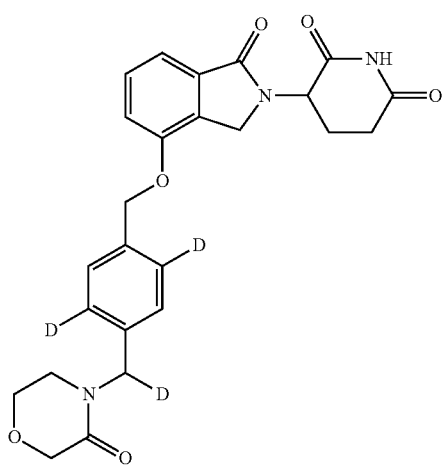
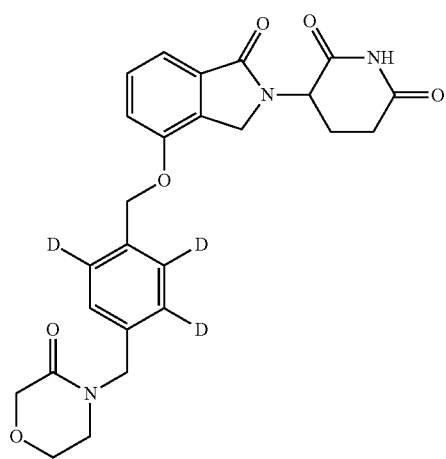 [SMILES: [2H]c1cc(CN2CCOCC2=O)c([2H])c([2H])c1COc1cccc2c1CN(C1CCC(=O)NC1=O)C2=O]
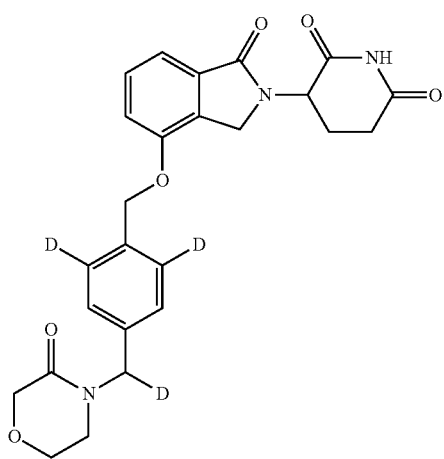 [SMILES: [2H]c1cc(C([2H])N2CCOCC2=O)cc([2H])c1COc1cccc2c1CN(C1CCC(=O)NC1=O)C2=O]

TABLE 3-continued
Deuterium enriched compounds of formula (II):
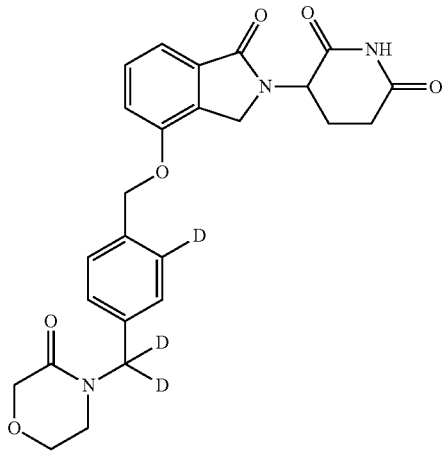 [SMILES: [2H]c1cc(C([2H])([2H])N2CCOCC2=O)ccc1COc1cccc2c1CN(C1CCC(=O)NC1=O)C2=O]
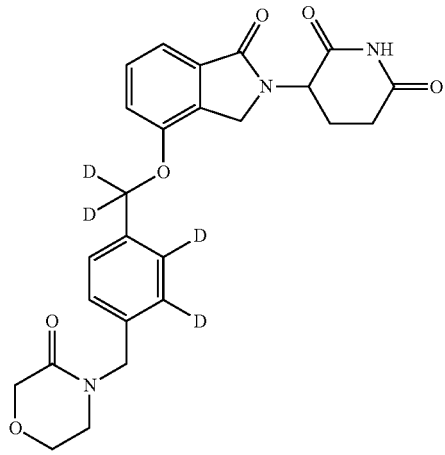
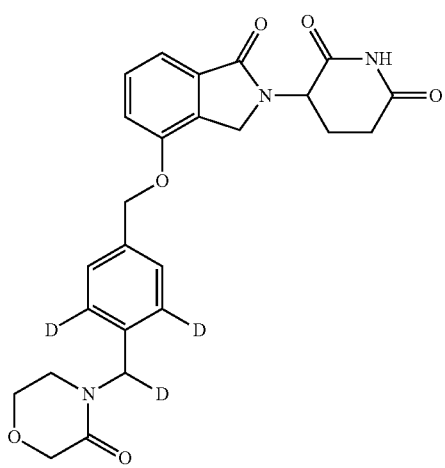 [SMILES: [2H]c1cc(COc2cccc3c2CN(C2CCC(=O)NC2=O)C3=O)cc([2H])c1C([2H])N1CCOCC1=O]
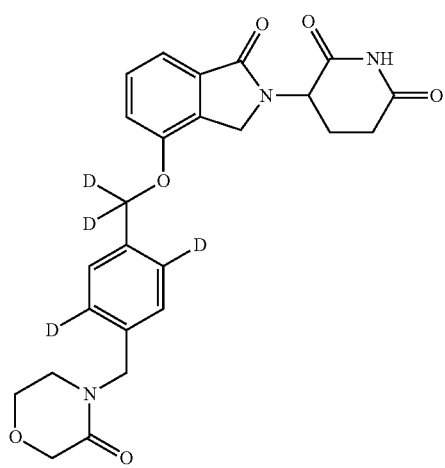
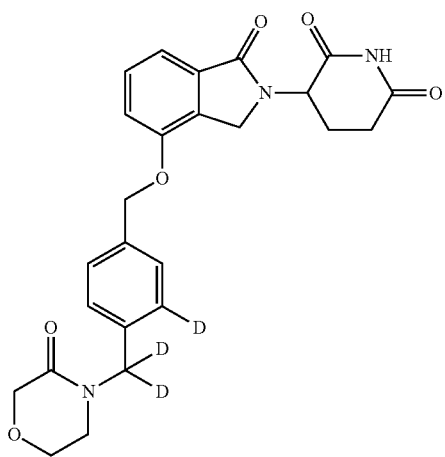 [SMILES: [2H]c1cc(COc2cccc3c2CN(C2CCC(=O)NC2=O)C3=O)ccc1C([2H])([2H])N1CCOCC1=O]
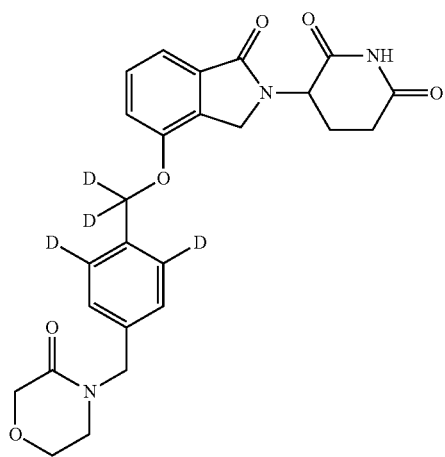 [SMILES: [2H]c1cc(CN2CCOCC2=O)cc([2H])c1C([2H])([2H])Oc1cccc2c1CN(C1CCC(=O)NC1=O)C2=O]

TABLE 3-continued
Deuterium enriched compounds of formula (II):
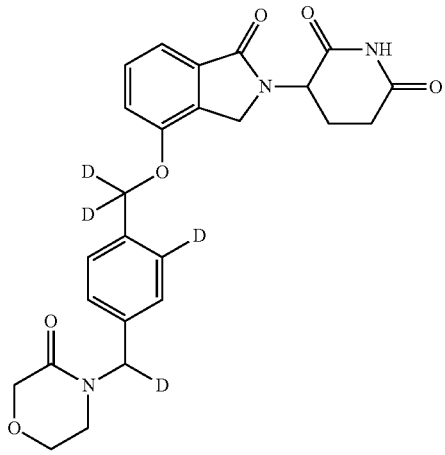 [SMILES: [2H]c1cc(C([2H])N2CCOCC2=O)ccc1C([2H])([2H])Oc1cccc2c1CN(C1CCC(=O)NC1=O)C2=O]
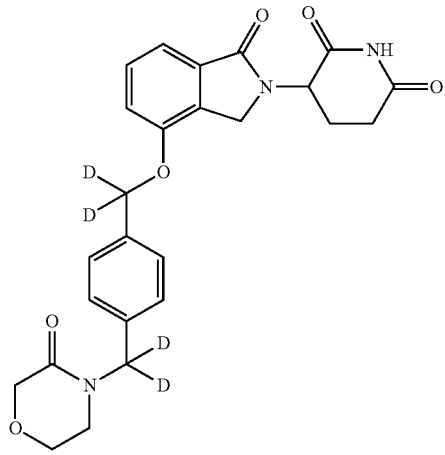
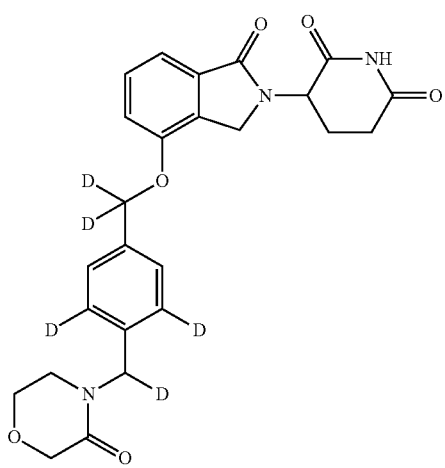 [SMILES: [2H]c1cc(C([2H])([2H])Oc2cccc3c2CN(C2CCC(=O)NC2=O)C3=O)cc([2H])c1C([2H])N1CCOCC1=O]
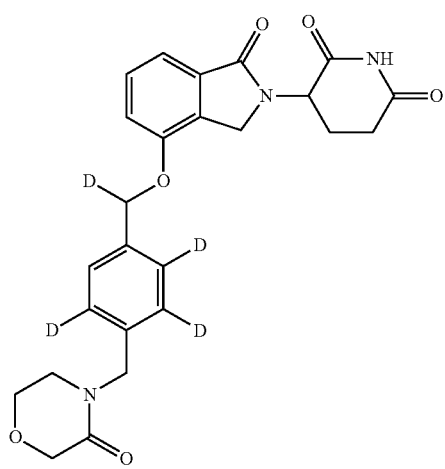
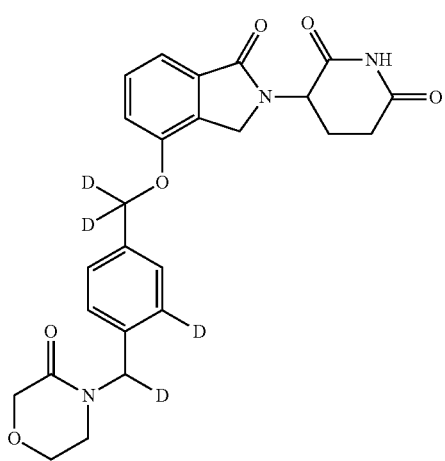 [SMILES: [2H]c1cc(C([2H])([2H])Oc2cccc3c2CN(C2CCC(=O)NC2=O)C3=O)ccc1C([2H])N1CCOCC1=O]
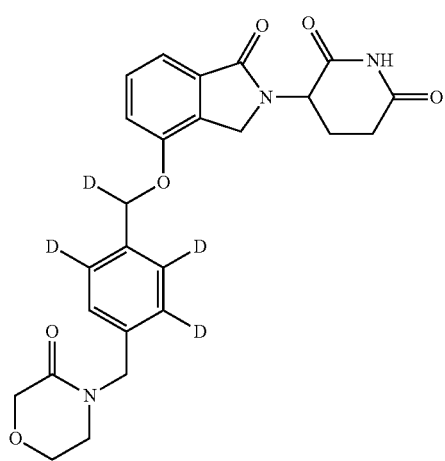 [SMILES: [2H]c1cc(CN2CCOCC2=O)c([2H])c([2H])c1C([2H])Oc1cccc2c1CN(C1CCC(=O)NC1=O)C2=O]

TABLE 3-continued

Deuterium enriched compounds of formula (II):

TABLE 3-continued
Deuterium enriched compounds of formula (II):
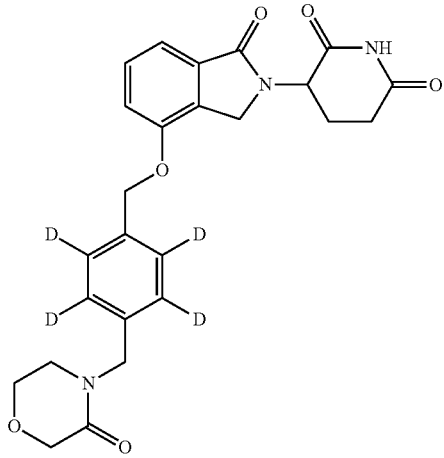 [SMILES: [2H]c1c([2H])c(CN2CCOCC2=O)c([2H])c([2H])c1COc1cccc2c1CN(C1CCC(=O)NC1=O)C2=O]
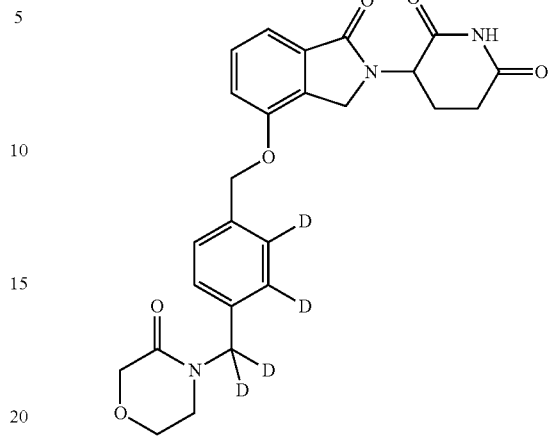
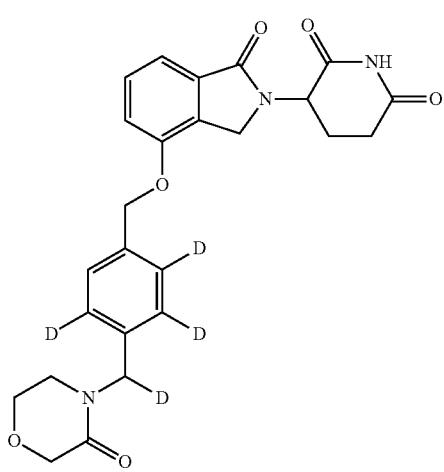 [SMILES: [2H]c1cc(COc2cccc3c2CN(C2CCC(=O)NC2=O)C3=O)c([2H])c([2H])c1C([2H])N1CCOCC1=O]
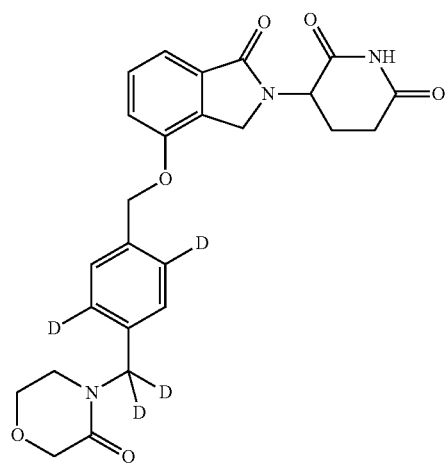 [SMILES: [2H]c1cc(C([2H])([2H])N2CCOCC2=O)c([2H])cc1COc1cccc2c1CN(C1CCC(=O)NC1=O)C2=O]
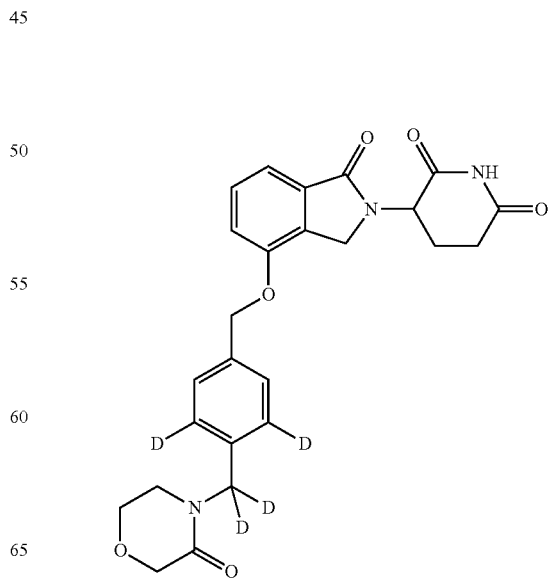

TABLE 3-continued
Deuterium enriched compounds of formula (II):
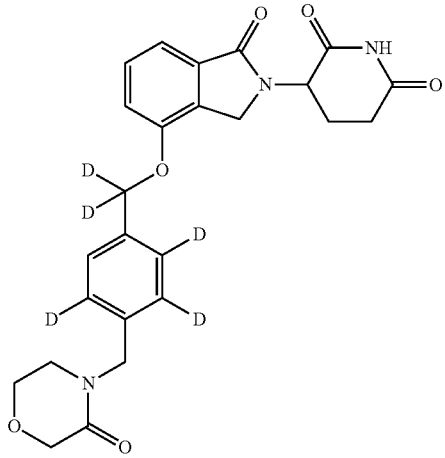 [SMILES: [2H]c1cc(C([2H])([2H])Oc2cccc3c2CN(C2CCC(=O)NC2=O)C3=O)c([2H])c([2H])c1CN1CCOCC1=O]
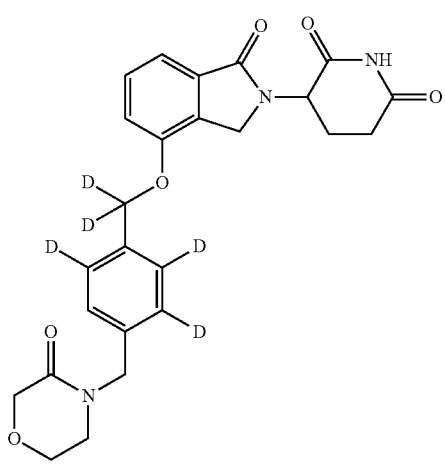 [SMILES: [2H]c1cc(CN2CCOCC2=O)c([2H])c([2H])c1C([2H])([2H])Oc1cccc2c1CN(C1CCC(=O)NC1=O)C2=O]
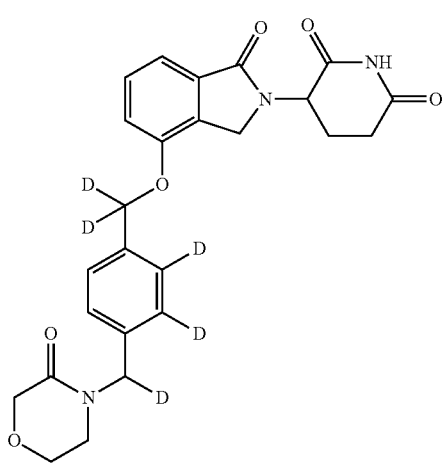 [SMILES: [2H]c1c(C([2H])N2CCOCC2=O)ccc(C([2H])([2H])Oc2cccc3c2CN(C2CCC(=O)NC2=O)C3=O)c1[2H]]
TABLE 3-continued
Deuterium enriched compounds of formula (II):
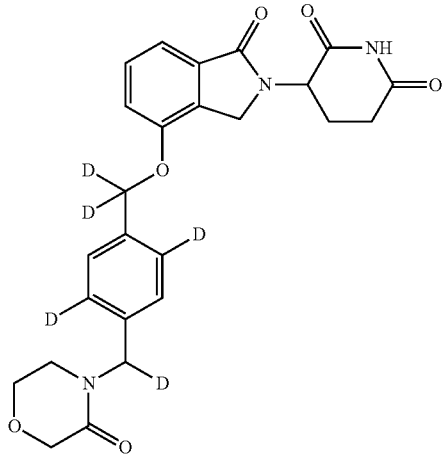 [SMILES: [2H]c1cc(C([2H])([2H])Oc2cccc3c2CN(C2CCC(=O)NC2=O)C3=O)c([2H])cc1C([2H])N1CCOCC1=O]
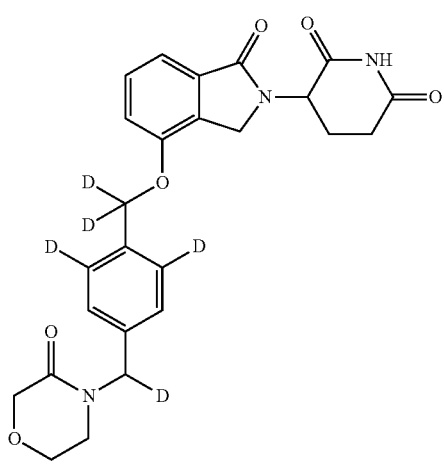 [SMILES: [2H]c1cc(C([2H])N2CCOCC2=O)cc([2H])c1C([2H])([2H])Oc1cccc2c1CN(C1CCC(=O)NC1=O)C2=O]
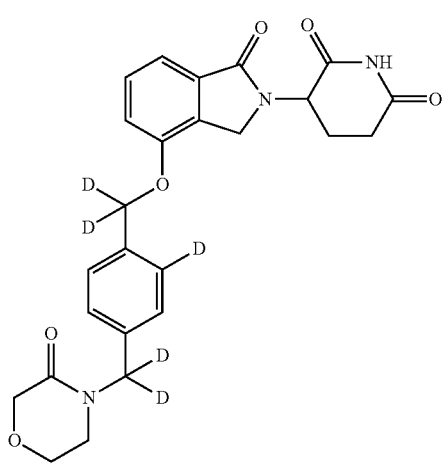 [SMILES: [2H]c1cc(C([2H])([2H])N2CCOCC2=O)ccc1C([2H])([2H])Oc1cccc2c1CN(C1CCC(=O)NC1=O)C2=O]

TABLE 3-continued
Deuterium enriched compounds of formula (II):
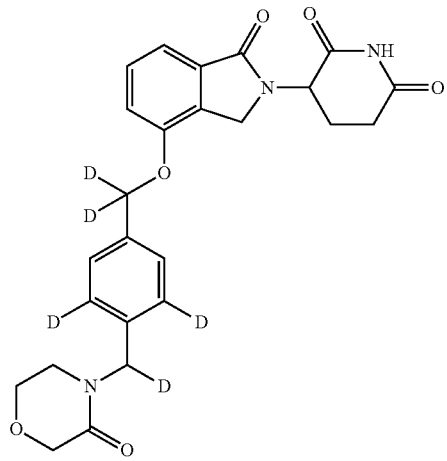 [SMILES: [2H]c1cc(C([2H])([2H])Oc2cccc3c2CN(C2CCC(=O)NC2=O)C3=O)cc([2H])c1C([2H])N1CCOCC1=O]
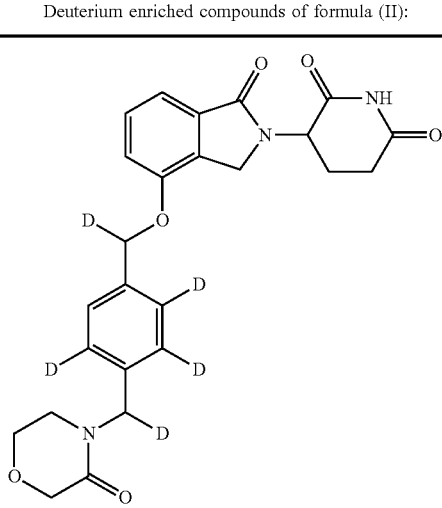
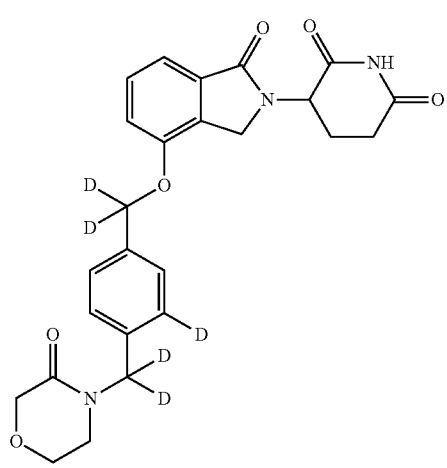 [SMILES: [2H]c1cc(C([2H])([2H])Oc2cccc3c2CN(C2CCC(=O)NC2=O)C3=O)ccc1C([2H])([2H])N1CCOCC1=O]
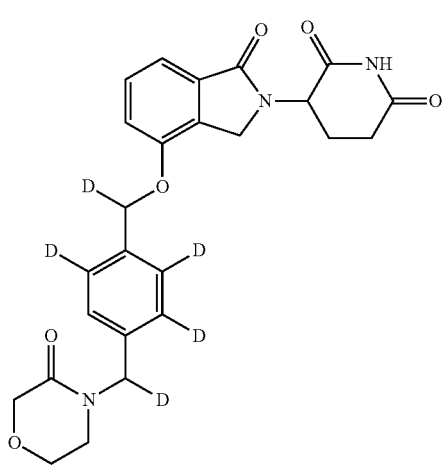
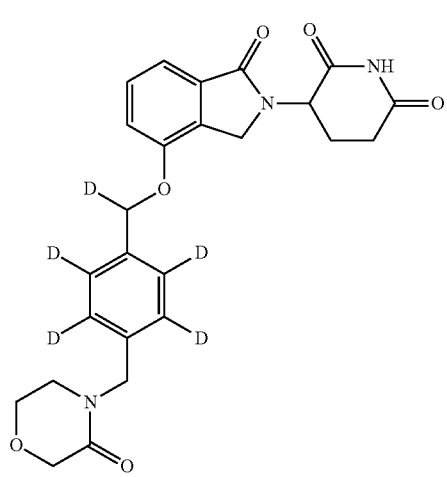 [SMILES: [2H]c1c([2H])c(C([2H])Oc2cccc3c2CN(C2CCC(=O)NC2=O)C3=O)c([2H])c([2H])c1CN1CCOCC1=O]
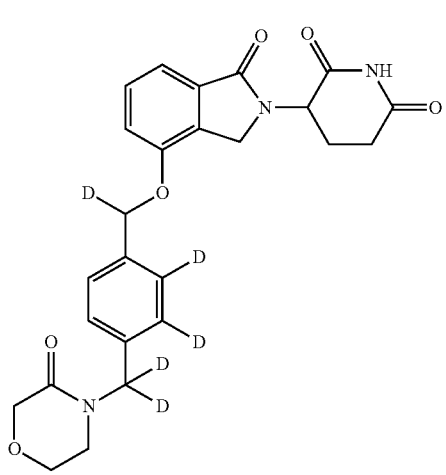 [SMILES: [2H]c1c(C([2H])Oc2cccc3c2CN(C2CCC(=O)NC2=O)C3=O)ccc(C([2H])([2H])N2CCOCC2=O)c1[2H]]

TABLE 3-continued
Deuterium enriched compounds of formula (II):
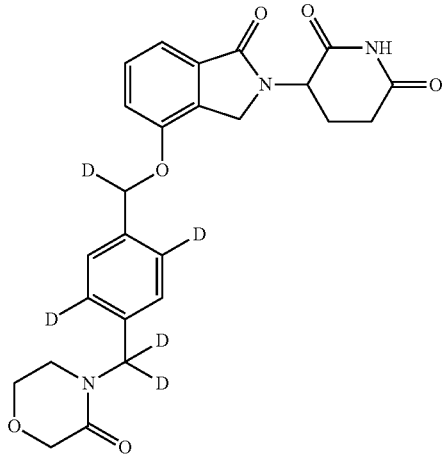 [SMILES: [2H]c1cc(C([2H])([2H])N2CCOCC2=O)c([2H])cc1C([2H])Oc1cccc2c1CN(C1CCC(=O)NC1=O)C2=O]
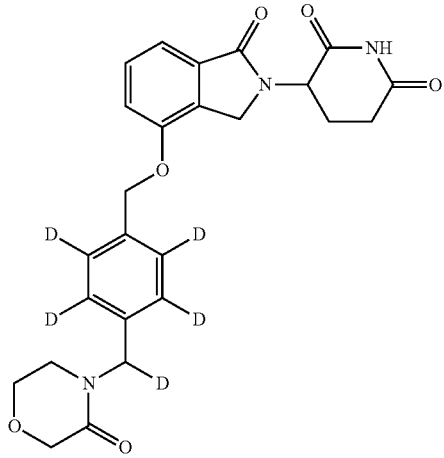
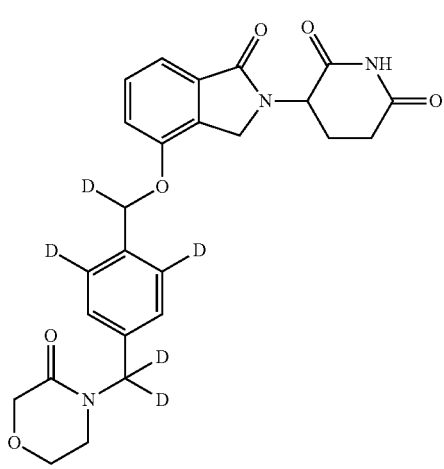 [SMILES: [2H]c1cc(C([2H])([2H])N2CCOCC2=O)cc([2H])c1C([2H])Oc1cccc2c1CN(C1CCC(=O)NC1=O)C2=O]
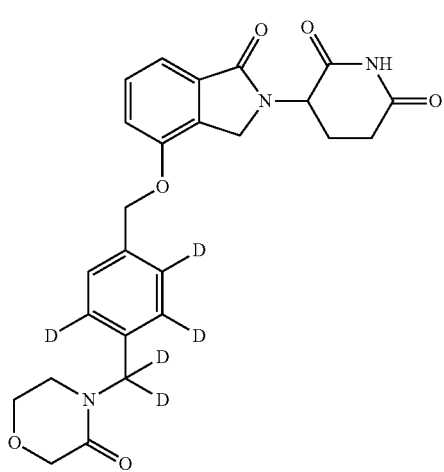
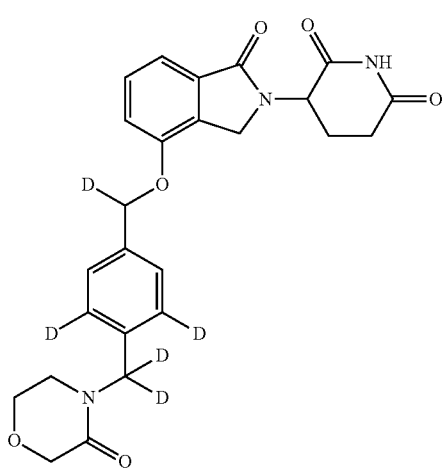 [SMILES: [2H]c1cc(C([2H])Oc2cccc3c2CN(C2CCC(=O)NC2=O)C3=O)cc([2H])c1C([2H])([2H])N1CCOCC1=O]
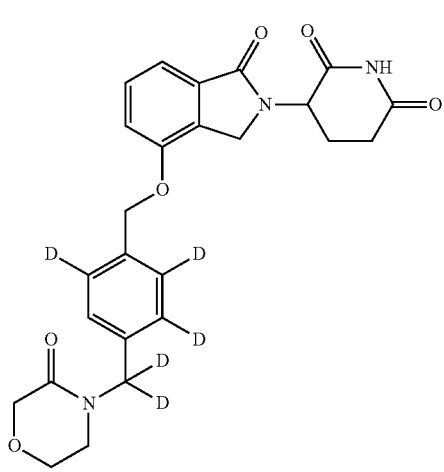 [SMILES: [2H]c1cc(C([2H])([2H])N2CCOCC2=O)c([2H])c([2H])c1COc1cccc2c1CN(C1CCC(=O)NC1=O)C2=O]

TABLE 3-continued
Deuterium enriched compounds of formula (II):
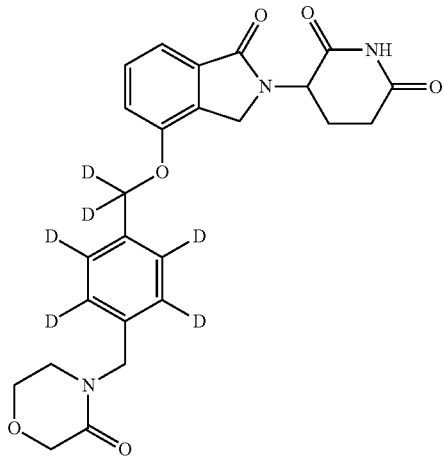 [SMILES: [2H]c1c([2H])c(C([2H])([2H])Oc2cccc3c2CN(C2CCC(=O)NC2=O)C3=O)c([2H])c([2H])c1CN1CCOCC1=O]
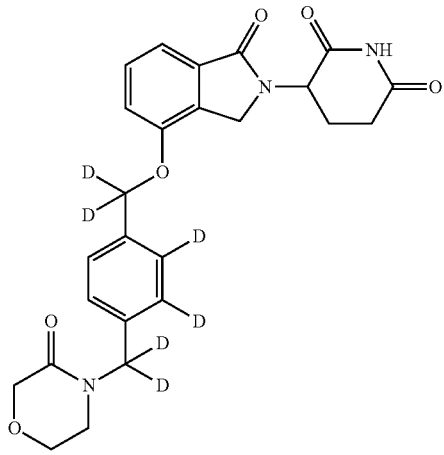
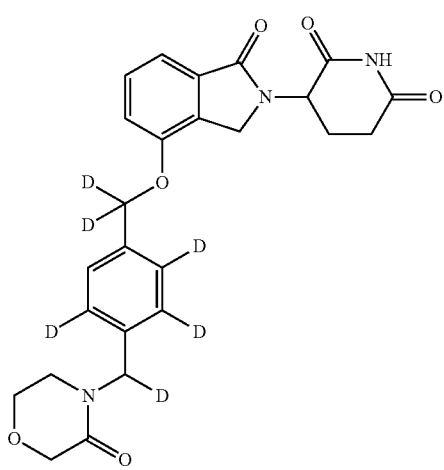 [SMILES: [2H]c1cc(C([2H])([2H])Oc2cccc3c2CN(C2CCC(=O)NC2=O)C3=O)c([2H])c([2H])c1C([2H])N1CCOCC1=O]
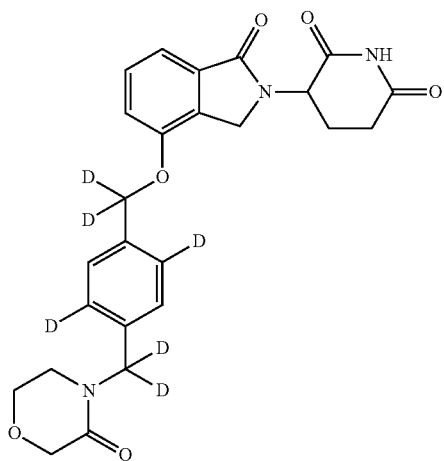
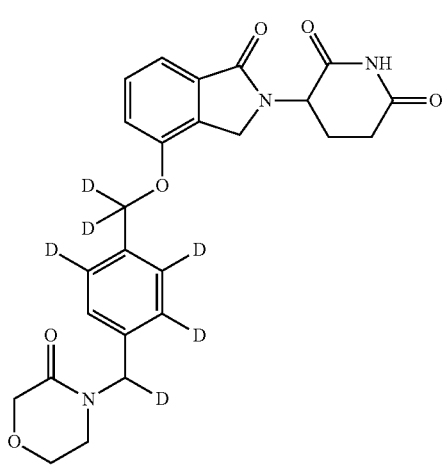 [SMILES: [2H]c1cc(C([2H])N2CCOCC2=O)c([2H])c([2H])c1C([2H])([2H])Oc1cccc2c1CN(C1CCC(=O)NC1=O)C2=O]
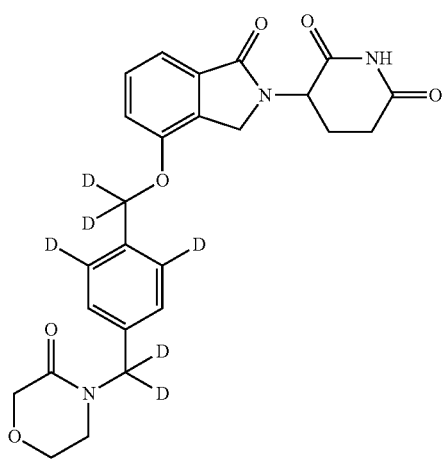 [SMILES: [2H]c1cc(C([2H])([2H])N2CCOCC2=O)cc([2H])c1C([2H])([2H])Oc1cccc2c1CN(C1CCC(=O)NC1=O)C2=O]

TABLE 3-continued
Deuterium enriched compounds of formula (II):
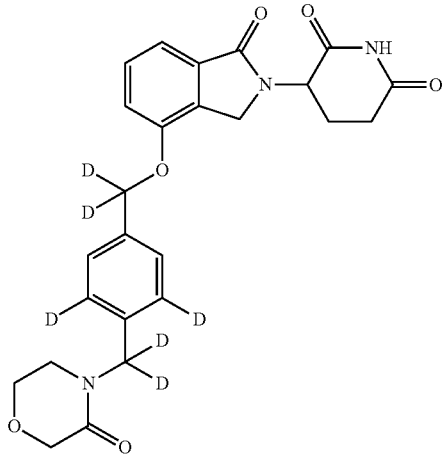 [SMILES: [2H]c1cc(C([2H])([2H])Oc2cccc3c2CN(C2CCC(=O)NC2=O)C3=O)cc([2H])c1C([2H])([2H])N1CCOCC1=O]
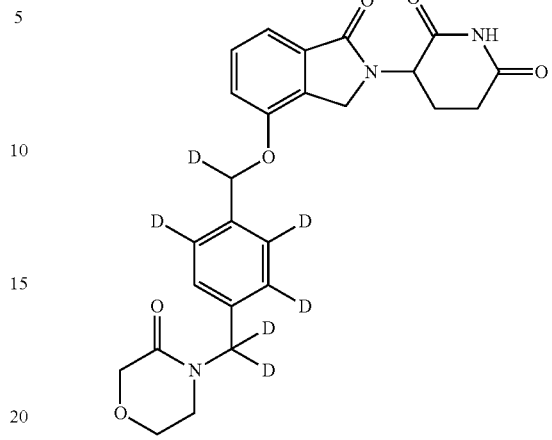
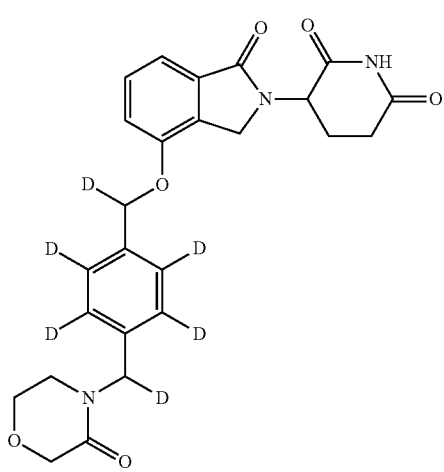 [SMILES: [2H]c1c([2H])c(C([2H])N2CCOCC2=O)c([2H])c([2H])c1C([2H])Oc1cccc2c1CN(C1CCC(=O)NC1=O)C2=O]
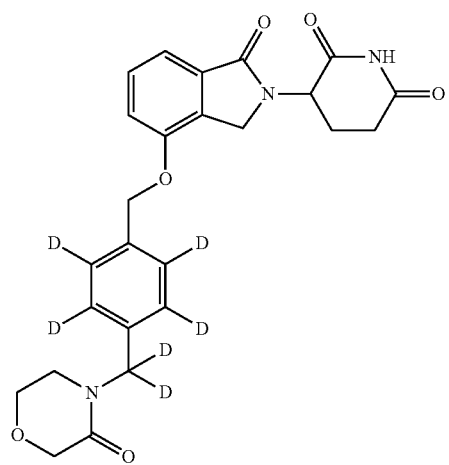
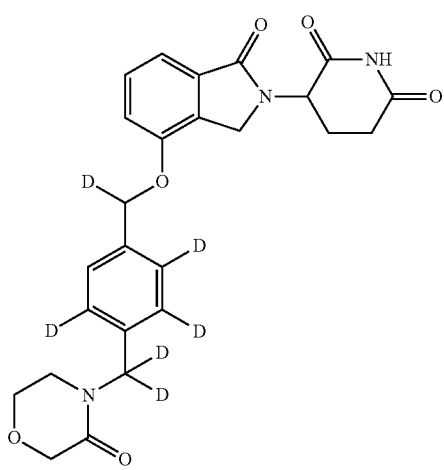 [SMILES: [2H]c1cc(C([2H])Oc2cccc3c2CN(C2CCC(=O)NC2=O)C3=O)c([2H])c([2H])c1C([2H])([2H])N1CCOCC1=O]
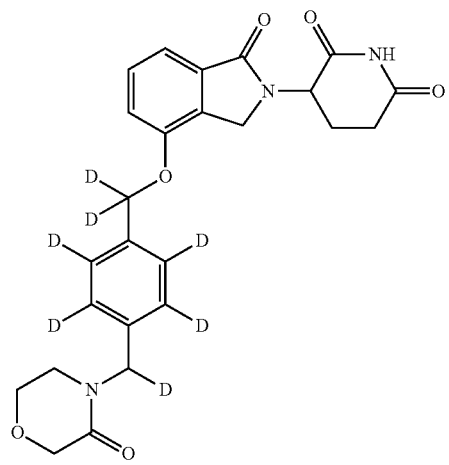 [SMILES: [2H]c1c([2H])c(C([2H])([2H])Oc2cccc3c2CN(C2CCC(=O)NC2=O)C3=O)c([2H])c([2H])c1C([2H])N1CCOCC1=O]

TABLE 3-continued
Deuterium enriched compounds of formula (II):
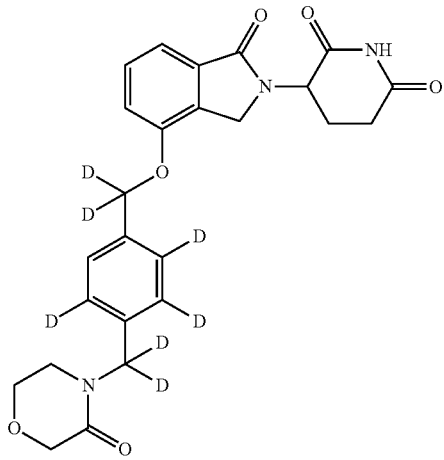 [SMILES: [2H]c1cc(C([2H])([2H])Oc2cccc3c2CN(C2CCC(=O)NC2=O)C3=O)c([2H])c([2H])c1C([2H])([2H])N1CCOCC1=O]
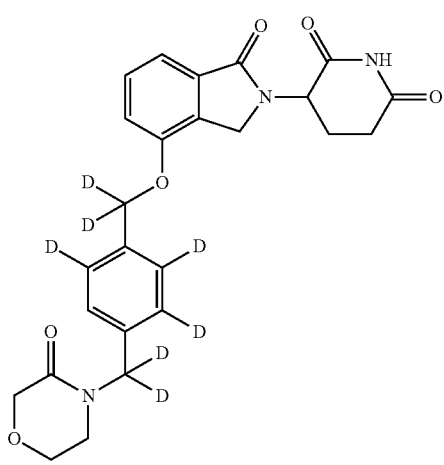 [SMILES: [2H]c1cc(C([2H])([2H])N2CCOCC2=O)c([2H])c([2H])c1C([2H])([2H])Oc1cccc2c1CN(C1CCC(=O)NC1=O)C2=O]
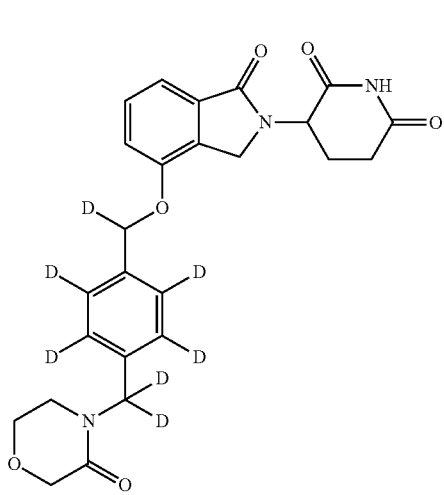 [SMILES: [2H]c1c([2H])c(C([2H])([2H])N2CCOCC2=O)c([2H])c([2H])c1C([2H])Oc1cccc2c1CN(C1CCC(=O)NC1=O)C2=O]
TABLE 3-continued
Deuterium enriched compounds of formula (II):
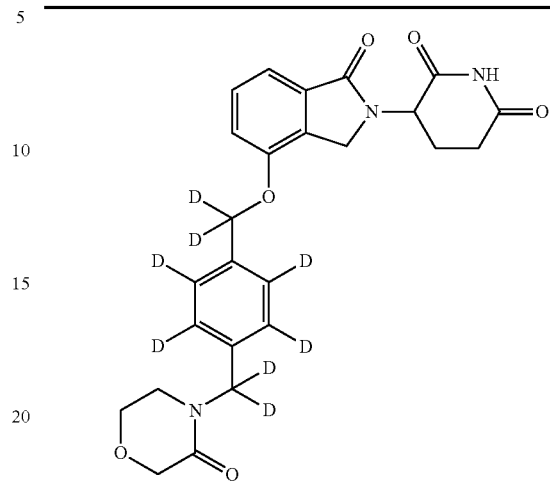
TABLE 4
Deuterium enriched compounds of formula (II):
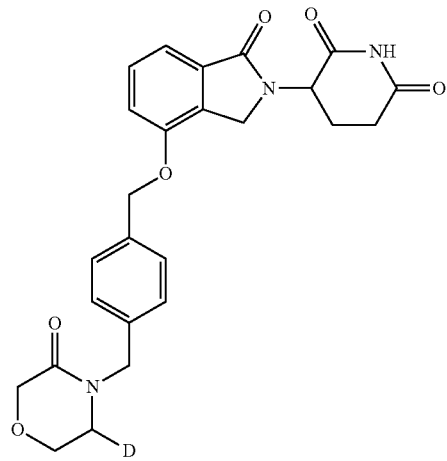 [SMILES: [2H]C1COCC(=O)N1Cc1ccc(COc2cccc3c2CN(C2CCC(=O)NC2=O)C3=O)cc1]
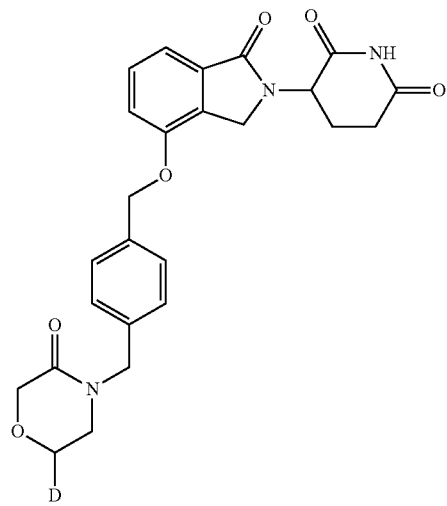 [SMILES: [2H]C1CN(Cc2ccc(COc3cccc4c3CN(C3CCC(=O)NC3=O)C4=O)cc2)C(=O)CO1]

TABLE 4-continued
Deuterium enriched compounds of formula (II):
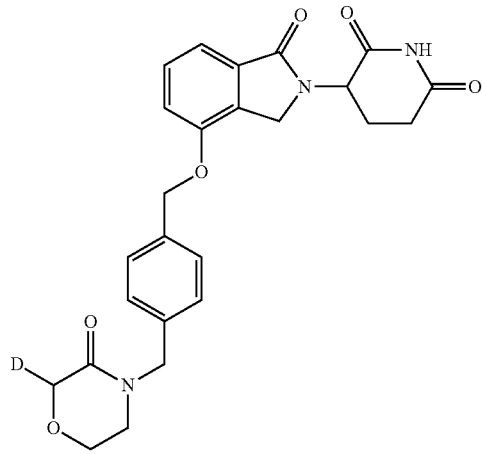 [SMILES: [2H]C1OCCN(Cc2ccc(COc3cccc4c3CN(C3CCC(=O)NC3=O)C4=O)cc2)C1=O]
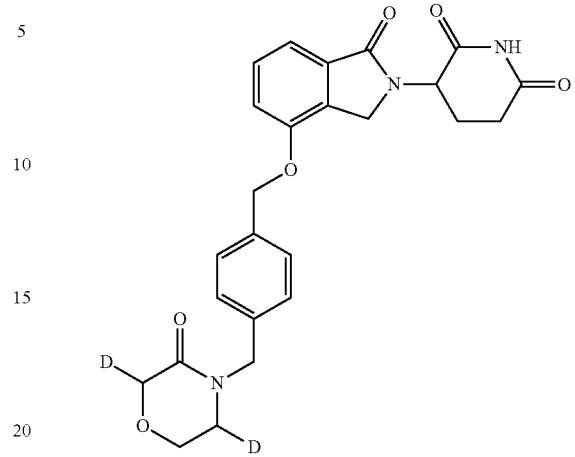
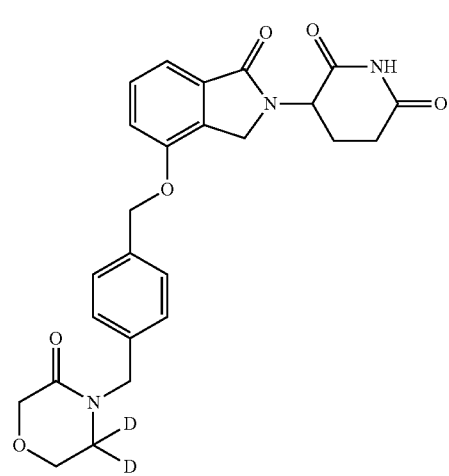 [SMILES: [2H]C1([2H])COCC(=O)N1Cc1ccc(COc2cccc3c2CN(C2CCC(=O)NC2=O)C3=O)cc1]
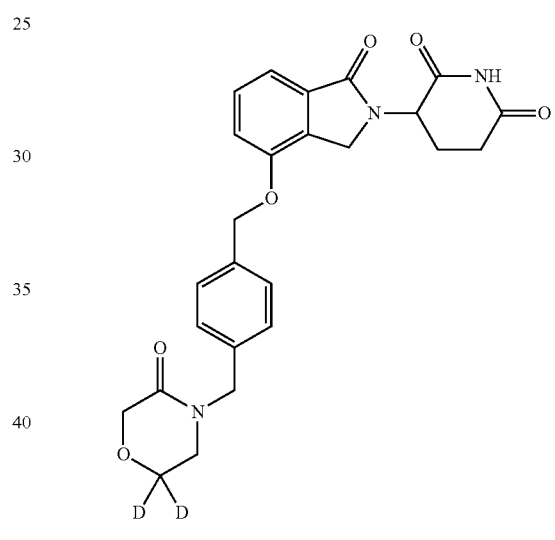
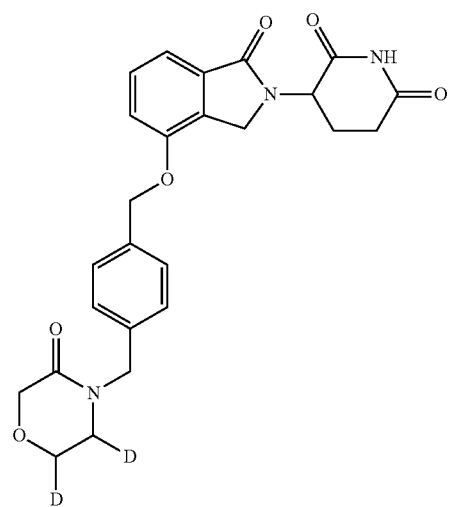 [SMILES: [2H]C1OCC(=O)N(Cc2ccc(COc3cccc4c3CN(C3CCC(=O)NC3=O)C4=O)cc2)C1[2H]]
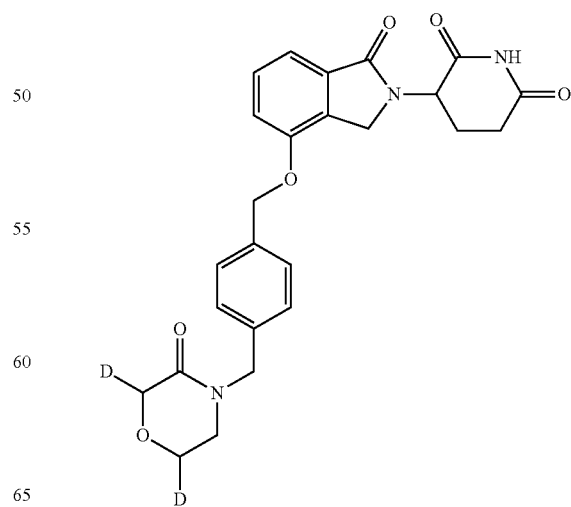

TABLE 4-continued
Deuterium enriched compounds of formula (II):
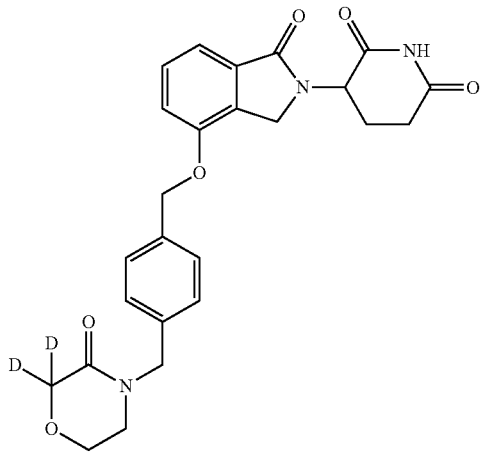 [SMILES: [2H]C1([2H])OCCN(Cc2ccc(COc3cccc4c3CN(C3CCC(=O)NC3=O)C4=O)cc2)C1=O]
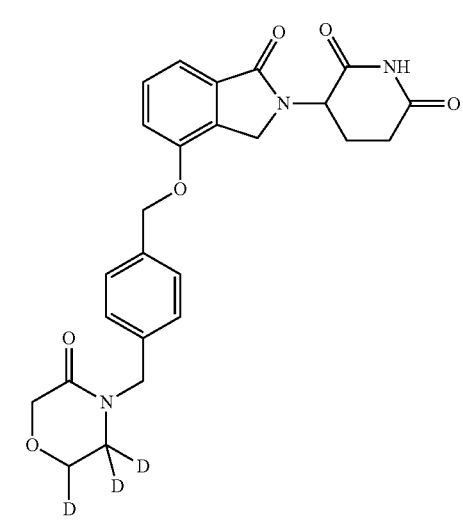 [SMILES: [2H]C1OCC(=O)N(Cc2ccc(COc3cccc4c3CN(C3CCC(=O)NC3=O)C4=O)cc2)C1([2H])[2H]]
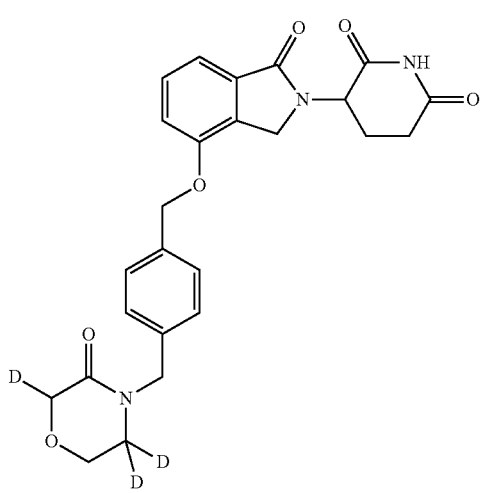 [SMILES: [2H]C1OCC([2H])([2H])N(Cc2ccc(COc3cccc4c3CN(C3CCC(=O)NC3=O)C4=O)cc2)C1=O]
TABLE 4-continued
Deuterium enriched compounds of formula (II):
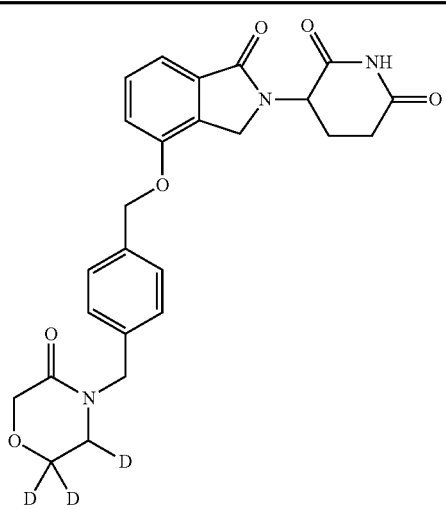
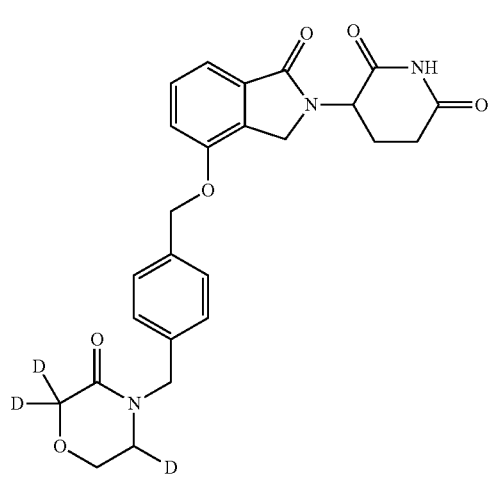 [SMILES: [2H]C1COC([2H])([2H])C(=O)N1Cc1ccc(COc2cccc3c2CN(C2CCC(=O)NC2=O)C3=O)cc1]

TABLE 4-continued
Deuterium enriched compounds of formula (II):
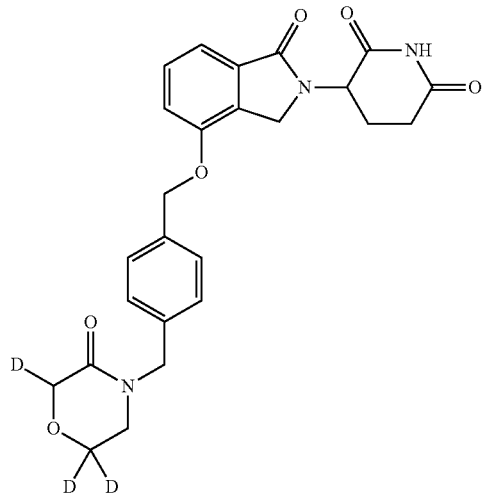 [SMILES: [2H]C1OC([2H])([2H])CN(Cc2ccc(COc3cccc4c3CN(C3CCC(=O)NC3=O)C4=O)cc2)C1=O]
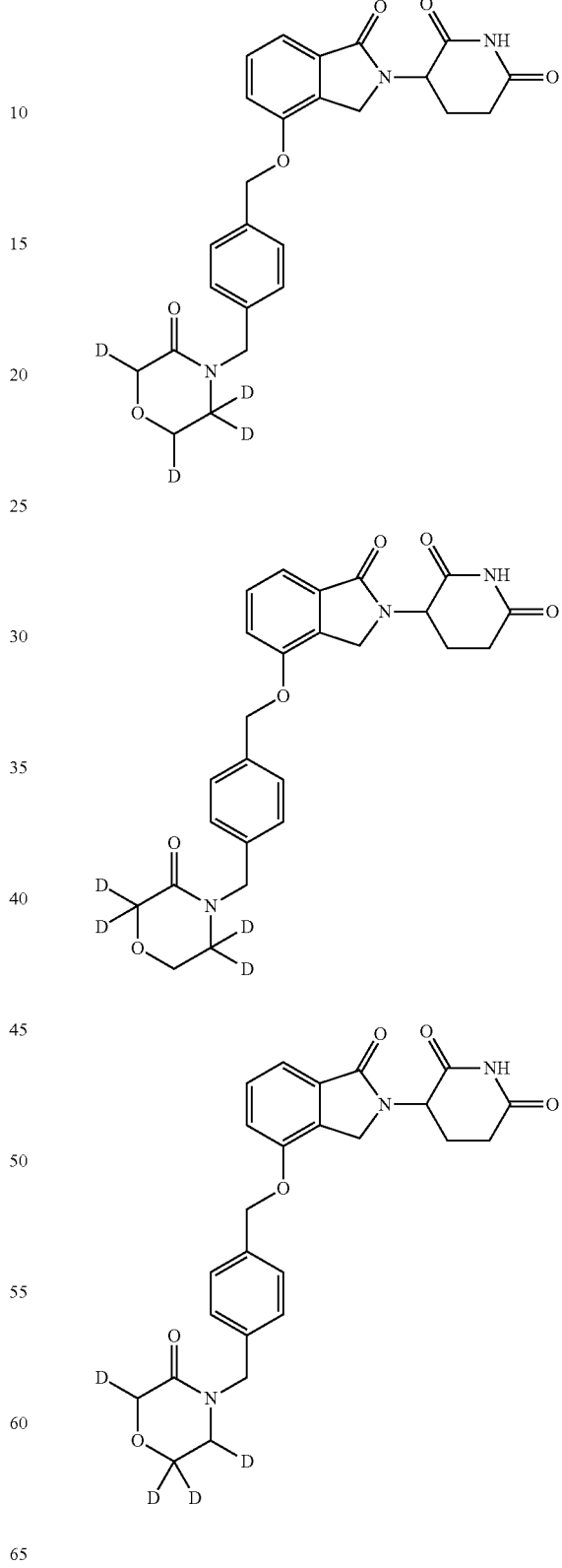

TABLE 4-continued
Deuterium enriched compounds of formula (II):
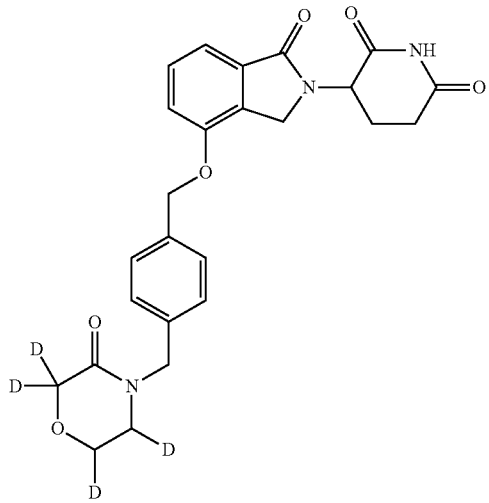 [SMILES: [2H]C1OC([2H])([2H])C(=O)N(Cc2ccc(COc3cccc4c3CN(C3CCC(=O)NC3=O)C4=O)cc2)C1[2H]]
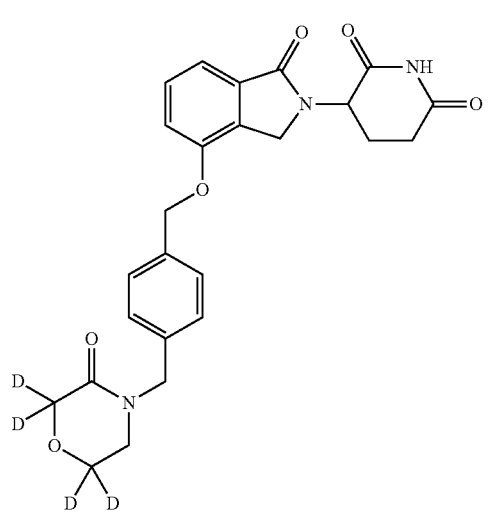 [SMILES: [2H]C1([2H])CN(Cc2ccc(COc3cccc4c3CN(C3CCC(=O)NC3=O)C4=O)cc2)C(=O)C([2H])([2H])O1]
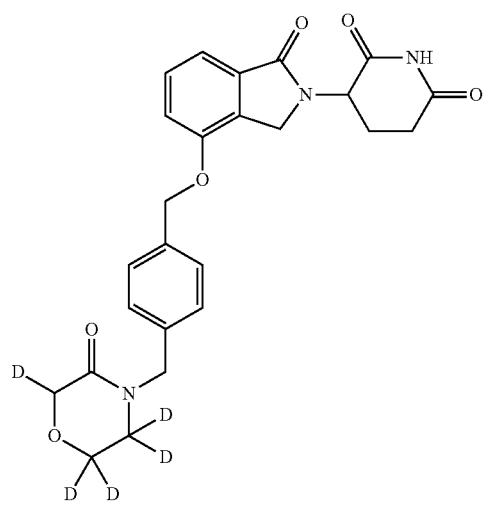 [SMILES: [2H]C1OC([2H])([2H])C([2H])([2H])N(Cc2ccc(COc3cccc4c3CN(C3CCC(=O)NC3=O)C4=O)cc2)C1=O]
TABLE 4-continued
Deuterium enriched compounds of formula (II):
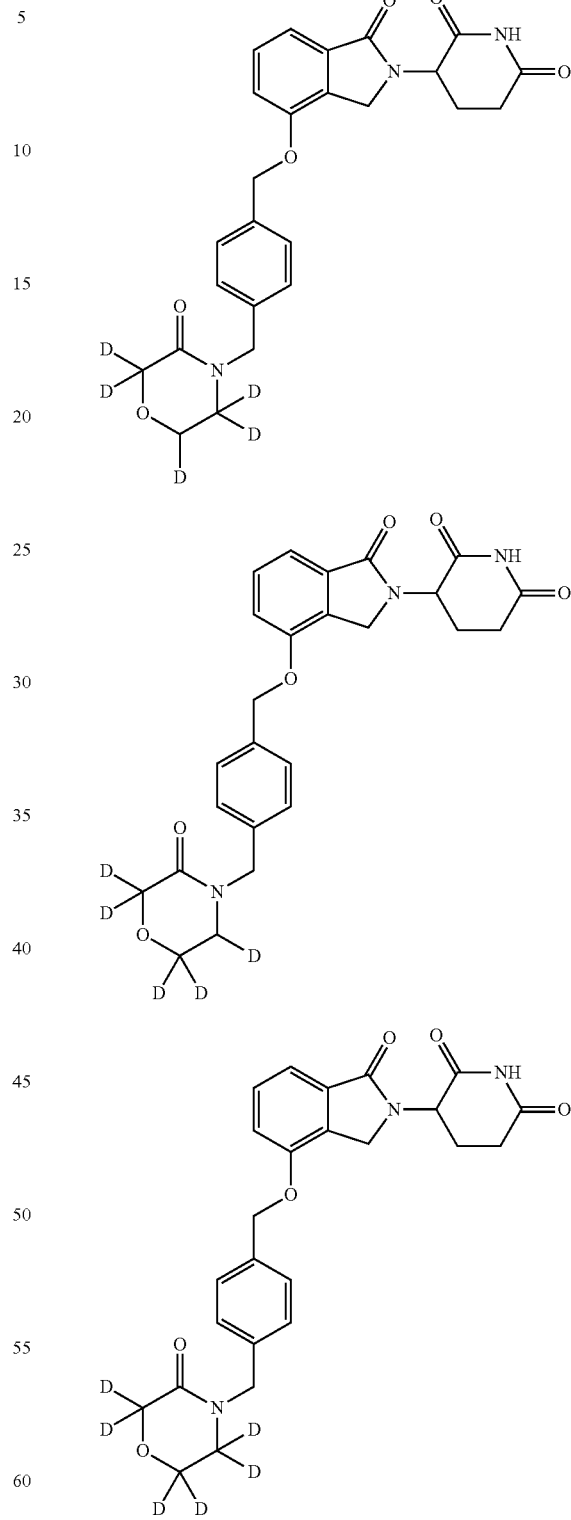
In certain embodiments, a compound provided herein may be any combination of deuterium substitutions as disclosed herein above in Tables 1 to 4. In other words, any combination of the deuterated glutarimide portion as shown in Table 1, deuterated isoindoline portion as shown in Table 2, deuterated phenyl alkyl portion as shown in Table 3 and deuterated morpholine portion as shown in Table 4 is encompassed herein.

In certain embodiments, a compound provided herein may be a stereoisomer of a compound of any one of Tables 1 to 4, or any combination thereof. In one embodiment, the S-enantiomer of a compound of any one of Tables 1 to 4, or any combination of deuterium substitutions thereof, is provided herein. In one embodiment, the R-enantiomer of a compound of any one of Tables 1 to 4, or any combination of deuterium substitutions thereof, is provided herein. For example, provided herein are the following S-enantiomer and R-enantiomer:

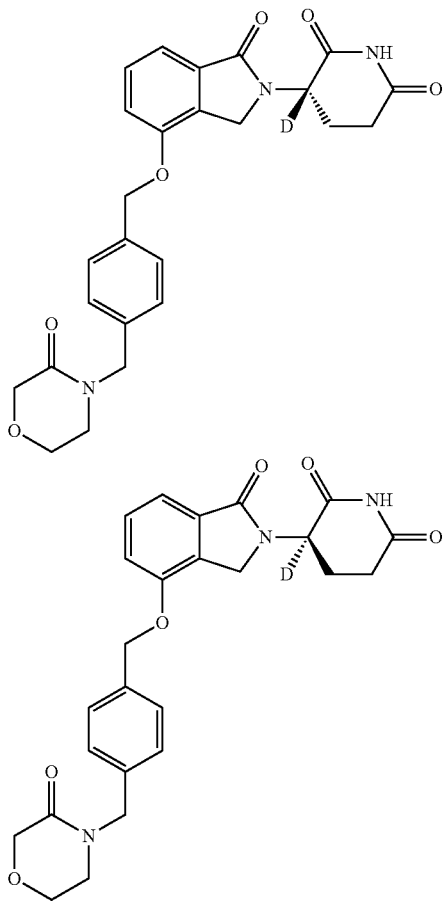

Methods of Treatment

In certain embodiments, provided herein are methods of treating, preventing, and/or managing various diseases or disorders using a compound provided herein. In certain embodiments, provided herein are methods of treating various diseases or disorders using a compound provided herein. In certain embodiments, provided herein are methods of managing various diseases or disorders using a compound provided herein. In certain embodiments, provided herein are methods of preventing various diseases or disorders using a compound provided herein. In certain embodiments, provided herein are methods of treating and managing various diseases or disorders using a compound provided herein. In certain embodiments, provided herein are methods of treating and preventing various diseases or disorders using a compound provided herein.

Also provided herein are the inventive compounds for use in any of the methods described herein.

Examples of diseases or disorders include, but are not limited to, cancer, disorders associated with angiogenesis, immunodeficiency disorders, hemoglobinopathy and related disorders (e.g., anemia), TNFα related disorders, and other various diseases and disorders.

In certain embodiments, provided herein is a method of treating, preventing, and/or managing an inflammatory disease, disorder, or condition, comprising administering to a subject a therapeutically effective amount of a treatment compound provided herein.

In certain embodiments, the disease is lupus, scleroderma, or Sjögren syndrome. In certain embodiments, the disease is lupus or scleroderma. In one embodiment, the disease is systemic lupus erythematosus. In one embodiment, the disease is scleroderma.

In certain embodiments, provided herein is a method of treating, preventing, and/or managing scleroderma or a symptom thereof, comprising administering to a subject having scleroderma a therapeutically effective amount of a treatment compound provided herein. In certain embodiments, provided herein is a method of treating, preventing, and/or managing scleroderma or a symptom thereof, comprising administering to a subject having scleroderma or at risk of having scleroderma a therapeutically effective amount of a treatment provided herein.

In certain embodiments, the scleroderma is localized, systemic, limited, or diffuse scleroderma.

In certain embodiments, the systemic scleroderma comprises CREST syndrome (Calcinosis, Raynaud's syndrome, esophagaeal dysfunction or dysmotility, sclerodactyly, and telangiectasia). Scleroderma is also known as systemic sclerosis or progressive systemic sclerosis.

In certain embodiments, the disease is Raynaud's disease. In certain embodiments, systemic sclerosis comprises scleroderma lung disease, scleroderma renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life.

In certain embodiments, limited scleroderma is limited to the hands, the face, neck, or combinations thereof.

In certain embodiments, diffuse scleroderma comprises skin tightening and also occurs above the wrists (or elbows). In certain embodiments, the diffuse systemic sclerosis is sine scleroderma, comprising internal organ fibrosis, but no skin tightening; or familial progressive systemic sclerosis.

In certain embodiments, scleroderma is not associated with wasting, such as disease-related wasting.

In certain embodiments, provided herein is a method for the reduction, inhibition, or prevention of one or more of the following symptoms of scleroderma: (i) gradual hardening, thickening, and tightening of the skin (e.g., in extremities, such as hands, face, and feet); (ii) skin discoloration; (iii) numbness of extremities; (iv) shiny skin; (v) small white lumps under the surface of the skin that erupt into a chalky white fluid; (vi) Raynaud's esophageal dysfunction (pain, numbness, and/or color changes in the hands caused by spasm of the blood vessels upon exposure to cold or emotional stress); (vii) telangiectasia (red spots on, e.g., the hands, palms, forearms, face, and lips); (viii) pain and/or stiffness of the joints; (ix) swelling of the hands and feet; (x) itching of the skin; (xi) stiffening and curling of the fingers; (xii) ulcers (sores) on the outside of certain joints, such as knuckles and elbows; (xiii) digestive problems, such as heartburn, difficulty in swallowing, diarrhea, irritable bowel, and constipation; (xiv) fatigue and weakness; (xv) shortness of breath; (xvi) arthritis; (xvii) hair loss; (xviii) internal organ problems; (xix) digital ulcers; or (xx) digital auto-amputation, comprising administering a therapeutically effective amount of a treatment provided herein to a subject in need thereof.

Without being bound to any particular theory, it is believed that the treatment provided herein compounds provided herein enhance Th1 immune response, and suppresses Th2 immune response, which may result in anti-fibrotic effects in the skin.

In certain embodiments, provided herein is a method for improving or reducing the skin thickness of a subject having scleroderma, comprising administering to the subject a therapeutically effective amount of a treatment compound provided herein. In certain embodiments, the skin thickness is reduced by about 20%, about 25%, about 30%, about 40%, about 50%, about 60%, about 70% about 80%, about 90% or more.

In certain embodiments, provided herein is a method for achieving one or more clinical endpoints in treating a subject with scleroderma, comprising administering to the subject a therapeutically effective amount of a treatment compound provided herein.

In certain embodiments, provided herein is a method for decreasing mortality, respiratory mortality and/or respiratory hospitalization of a subject having scleroderma, comprising administering to the subject a therapeutically effective amount of a treatment compound provided herein.

In certain embodiments, provided herein is a method for improving the modified Rodnan skin score of a subject having scleroderma, comprising administering to the subject a therapeutically effective amount of a treatment provided herein. In certain embodiments, the improvement in modified Rodnan skin score is about 5, about 10, about 15, or about 20 points or more.

In certain embodiments, provided herein is a method for improving or reducing the skin thickness of a subject having scleroderma, comprising administering to the subject a therapeutically effective amount of a treatment compound provided herein. In certain embodiments, the skin thickness is reduced by about 20%, about 25%, about 30%, about 40%, about 50%, about 60%, about 70% about 80%, about 90% or more.

In certain embodiments, provided herein is a method for improving or reducing skin induration of a subject having scleroderma, comprising administering to the subject a therapeutically effective amount of a treatment compound provided herein.

In certain embodiments, provided herein is a method for improving the dermatology quality of life index of a subject having scleroderma, comprising administering to the subject a therapeutically effective amount of a treatment compound provided herein.

In certain embodiments, provided herein is a method for improving the pulmonary function of a subject having scleroderma, comprising administering to the subject a therapeutically effective amount of a treatment compound provided herein.

In certain embodiments, provided herein is a method for improving the carbon monoxide diffusing capacity of a subject having scleroderma, comprising administering to the subject a therapeutically effective amount of a treatment compound provided herein. In certain embodiments, the carbon monoxide diffusing capacity of a subject is improved by an improvement in the diffusing capacity of the lung for carbon monoxide ($D_Lco$) of about 10%, about 20%, about 25%, about 30%, about 40%, about 50%, about 60%, about 70% about 80%, about 90% or more.

In certain embodiments, provided herein is a method for improving the Mahler Dyspnea index of a subject having scleroderma, comprising administering to the subject a therapeutically effective amount of a treatment compound provided herein. In certain embodiments, the improvement in Mahler Dyspnea index is about 4, about 5, about 6, about 7, about 8, about 9, or about 10 points or more.

In certain embodiments, provided herein is a method for improving the Saint George's Respiratory Questionnaire score of a subject having scleroderma, comprising administering to the subject a therapeutically effective amount of a treatment compound provided herein. In certain embodiments, the improvement in Saint George's Respiratory Questionnaire score is about 4, about 8, about 12, about 16, about 20, about 24, about 28, about 32, about 36, about 40, about 44, about 48, about 52 points or more.

In certain embodiments, provided herein is a method for improving the UCLA scleroderma clinical trial consortium gastrointestinal tract score of a subject having scleroderma, comprising administering to the subject a therapeutically effective amount of a treatment compound provided herein.

In certain embodiments, provided herein is a method for treating or preventing digital ulcer of a subject having scleroderma, comprising administering to the subject a therapeutically effective amount of a treatment compound provided herein.

In certain embodiments, provided herein is a method for improving flow-mediated dilatation of a subject having scleroderma, comprising administering to the subject a therapeutically effective amount of a treatment compound provided herein.

In certain embodiments, provided herein is a method for improving or increasing the six minute walk distance of a subject having scleroderma, comprising administering to the subject a therapeutically effective amount of a treatment compound provided herein. In certain embodiments, the improvement in the six minute walk distance is about 200 meters, about 250 meters, about 300 meters, about 350 meters, about 400 meters or more.

In certain embodiments, provided herein is a method of treating, preventing, and/or managing lupus erythematosus or a symptom thereof, comprising administering to a subject having lupus erythematosus a therapeutically effective amount of a treatment compound provided herein.

In certain embodiments, provided herein is a method of preventing lupus erythematosus or a symptom thereof, comprising administering to a subject at risk of having lupus erythematosus a therapeutically effective amount of a treatment compound provided herein.

In certain embodiments, the disease is systemic lupus erythematosus (SLE), cutaneous lupus erythematosus (CLE), or drug-induced lupus.

The phrase "Systemic lupus erythematosus" is interchangeably used herein with SLE and lupus and refers to all manifestations of the disease as known in the art (including remissions and flares). In SLE, abnormal hyperactivity of B lymphocytes and massive abnormal production of immunoglobulin gamma (IgG) auto-antibodies play a key role. This pathological process results in sequestration and destruction of Ig-coated cells, fixation and cleaving of complement proteins, and release of chemotaxins, vasoactive peptides and destructive enzymes into tissues (Hahn B H. Systemic Lupus Erythematosus. In: Kasper D L, Braunwald E, Fauci A S, Hauser S L, Longo D L, Jameson, J L, editors. In: *Harrison's Principles of Internal Medicine* (16th edition); New York (US): McGraw-Hill; 2005. pp. 1960-1967).

Symptoms of SLE vary from person to person, and may come and go. In most patients, the symptoms include joint pain and swelling. Frequently affected joints are the fingers, hands, wrists, and knees. Some patients develop arthritis. Other common symptoms include: chest pain when taking a deep breath, fatigue, fever with no other cause, general discomfort, uneasiness, or ill feeling (malaise), hair loss, mouth sores, swollen lymph nodes, sensitivity to sunlight, skin rash—a "butterfly" rash over the cheeks and bridge of the nose affects about half of people with SLE, in some patients, the rash gets worse in sunlight, and the rash may also be widespread.

Other symptoms depend on what part of the body is affected, and may include the following:
Brain and nervous system: headaches, numbness, tingling, seizures, vision problems, personality changes,
Digestive tract: abdominal pain, nausea, and vomiting,
Heart: abnormal heart rhythms (arrhythmias),
Lung: coughing up blood and difficulty breathing, and
Skin: patchy skin color, fingers that change color when cold (Raynaud's phenomenon).

Some patients only have skin symptoms. This is called discoid lupus.

In certain embodiments, the disease is moderate, severe, or very severe SLE. The term "severe SLE" as used herein refers to an SLE condition where the patient has one or more severe or life-threatening symptoms (such as hemolytic anemia, extensive heart or lung involvement, kidney disease, or central nervous system involvement).

In certain embodiments, provided herein is a method for achieving one or more clinical endpoints in treating a subject with SLE, comprising administering to the subject a therapeutically effective amount of a treatment compound provided herein.

In certain embodiments, provided herein is a method for the overall survival, objective response rate, time to progression, progression-free survival and/or time-to-treatment failure of a subject having SLE, comprising administering to the subject a therapeutically effective amount of a treatment compound provided herein.

In certain embodiment, certain treatment compounds provided herein act as an inhibitor of primary human memory CD 19+ B-cell differentiation to the plasmablast stage. Without being bound to any particular theory, it is believed that certain treatment compounds provided herein block cells at a premature stage thereby decreasing the numbers of plasmablasts that are capable of producing high levels of immunoglobulin. A functional consequence of this effect is reduced immunoglobulin G (IgG) and immunoglobulin M (IgM) production in these differentiation cultures.

In certain embodiments, provided herein is a method for treating, managing, or preventing an immune-related disease, disorder, or condition, comprising administering to a subject a therapeutically effective amount of a treatment compound provided herein.

In certain embodiments, provided herein is a method of treating a disease, disorder, or condition caused by, or is associated with, an inappropriate or undesirable immune response, comprising administering to a subject a therapeutically effective amount of a treatment compound provided herein.

In certain embodiments, provided herein is a method of treating a disease, disorder, or condition that can be treated beneficially by immunosuppression, comprising administering to a subject a therapeutically effective amount of a treatment compound provided herein.

In certain embodiments, the immune-related disease, i.e., a disease, disorder, or condition caused by, or is associated with, an inappropriate or undesirable immune response, is Sjögren syndrome, ANCA-induced vasculitis, anti-phospholipid syndrome, myasthenia gravis, Addison's disease, alopecia areata, ankylosing spondylitis, antiphospholipid antibody syndrome, antiphospholipid syndrome (primary or secondary), asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatrical pemphigoid (e.g., mucous membrane pemphigoid), cold agglutinin disease, degos disease, dermatitis hepatiformis, essential mixed cryoglobulinemia, Goodpasture's syndrome, Graves' disease, Guillain-Barre syndrome, Hashimoto's thyroiditis (Hashimoto's disease; autoimmune thyroditis), idiopathic pulmonary fibrosis, idiopathic thrombocytopenia purpura, IgA nephropathy, juvenile arthritis, lichen planus, Meniere disease, mixed connective tissue disease, morephea, narcolepsy, neuromyotonia, pediatric autoimmune neuropsychiatric disorders (PANDAs), pemphigus vulgaris, pernicious anemia, polyarteritis nodosa, polychondritis, polymyalgia rheumatica, primary agammaglobulinemia, primary biliary cirrhosis, Raynaud disease (Raynaud phenomenon), Reiter's syndrome, relapsing polychondritis, rheumatic fever, Sjogren's syndrome, stiff-person syndrome (Moersch-Woltmann syndrome), Takayasu's arteritis, temporal arteritis (giant cell arteritis), uveitis, vasculitis (e.g., vasculitis not associated with lupus erythematosus), vitiligo, or Wegener's granulomatosis.

In one embodiment, provided herein is a method of treating and preventing cancer, which comprises administering to a patient a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof.

In another embodiment, provided herein is method of managing cancer, which comprises administering to a patient a compound provided herein, e.g., or an isotopologue thereof, or an enantiomer or a mixture of enantiomers thereof, or a pharmaceutically acceptable salt, solvate (e.g., hydrate), prodrug, clathrate, polymorph, or co-crystal thereof.

Provided herein are methods of treating or managing lymphoma, particularly non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

Also provided herein are methods of treating patients who have been previously treated for cancer but are non-responsive to standard therapies, as well as those who have not previously been treated. Provided herein are methods of treating patients regardless of patient's age, although some diseases or disorders are more common in certain age groups. In one embodiment, provided herein are methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and hematological or blood borne tumors. The term "cancer" refers to disease of skin tissues, organs, blood, and vessels, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a blood borne tumor. In certain embodiments, the blood borne tumor is metastatic. In certain embodiments, the blood borne tumor is drug resistant. In certain embodiments, the cancer is myeloma, leukemia, or lymphoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, provided herein are methods of treating, preventing, and/or managing disease in patients with impaired renal function. In certain embodiments, provided herein are method of treating, preventing, and/or managing cancer in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, and/or managing multiple myeloma, comprising administering to a patient in need thereof a therapeutically effective amount of a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof. In one embodiment, the multiple myeloma is relapsed/refractory multiple myeloma.

In certain embodiments, provided herein are methods of treating, preventing, and/or managing multiple myeloma, comprising administering to a patient in need thereof a therapeutically effective amount of a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, in combination with dexamethasone. In one embodiment, the multiple myeloma is relapsed/refractory multiple myeloma. In one embodiment, the combination therapy is administered in one or more 28-day cycles. In one embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered daily for 21 days (e.g., days 1-21) followed by 7-day rest (e.g., days 22-28). In one embodiment, the combination therapy is administered in one or more 7-day cycles. In one embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered daily for 5 days (e.g., days 1-5) followed by 2-day rest (e.g., days 6-7). In one embodiment, dexamethasone is administered once every 7 days. In one embodiment, dexamethasone is administered on days 1, 8, 15, and 22 of each 28-day cycle. In one embodiment, dexamethasone is administered at a dose of from about 10 mg to about 50 mg. In one embodiment, dexamethasone is administered at a dose of from about 20 mg to about 40 mg. In one embodiment, dexamethasone is administered at a dose of 20 mg (e.g., in subjects >75 years old). In one embodiment, dexamethasone is administered at a dose of 40 mg (e.g., in subjects ≤75 years old). In one embodiment, dexamethasone is administered orally.

In certain embodiments, provided herein are methods of treating, preventing, and/or managing relapsed/refractory multiple myeloma in patients with impaired renal function or a symptom thereof, comprising administering a therapeutically effective amount of the compound of Formula (I), or an enantiomer or a mixture of enantiomers thereof, or a pharmaceutically acceptable salt, solvate, hydrate, stereoisomer, tautomer or racemic mixtures thereof to a patient having relapsed/refractory multiple myeloma with impaired renal function.

In one embodiment, provided herein are methods of preventing relapsed/refractory multiple myeloma in patients with impaired renal function or a symptom thereof, comprising administering an effective amount of a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, to a patient at risk of having relapsed/refractory multiple myeloma with impaired renal function.

In certain embodiments, provided herein are methods for treating, preventing, and/or managing relapsed/refractory multiple myeloma in patients with impaired renal function.

In certain embodiments, provided herein is a method for increasing the overall survival, objective response rate, time to progression, progression-free survival and/or time-to-treatment failure of a subject having cancer, comprising administering to the subject a therapeutically effective amount of a treatment compound provided herein.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiment, a therapeutically or prophylactically effective amount is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day.

In certain embodiments, the therapeutically or prophylactically effective amount is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day to patients with NHL (e.g., DLBCL). In a particular embodiment, the compound can be administered in an amount of about 10 mg/day to patients with NHL (e.g., DLBCL).

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the patient to be treated with one of the methods provided herein has not been treated with anticancer therapy prior to the administration of a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof. In certain embodiments, the patient to be treated with one of the methods provided herein has been treated with anticancer therapy prior to the administration of a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof. In certain embodiments, the patient to be treated with one of the methods provided herein has developed drug resistance to the anticancer therapy.

Depending on the disease to be treated and the subject's condition, a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. A compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, may be formulated, alone or together, in suitable dosage unit with pharmaceutically acceptable excipients, carriers, adjuvants and vehicles, appropriate for each route of administration.

In one embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered orally. In another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered parenterally. In yet another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered intravenously.

The compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound of Formula (I), is administered once or more than once each day, for example, for a period of time. The term "continuous" is intended to mean that a therapeutic compound, such as the compound of Formula (I), is administered daily for an uninterrupted period of at least 10 days to 52 weeks. The term "intermittent" or "intermittently" as used herein is intended to mean stopping and starting at either regular or irregular intervals. For example, intermittent administration of the compound of Formula (I) is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound of Formula (I), is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered once a day. In another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered twice a day. In yet another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered three times a day. In still another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered four times a day.

In certain embodiments, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered once per day from one day to six months, from one week to three months, from one week to four weeks, from one week to three weeks, or from one week to two weeks. In certain embodiments, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered once per day for one week, two weeks, three weeks, or four weeks. In one embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered once per day for one week. In another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered once per day for two weeks. In yet another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered once per day for three weeks. In still another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered once per day for four weeks.

Second Active Agents

A compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, can be combined with other pharmacologically active compounds ("second active agents") in methods and compositions provided herein. Certain combinations may work synergistically in the treatment of particular types diseases or disorders, and conditions and symptoms associated with such diseases or disorders. A compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, can also work to alleviate adverse effects associated with certain second active agents, and vice versa.

In certain embodiments, a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered in combination or alternation with a therapeutically effective amount of one or more additional active agents. Second active agents include small molecules and large molecules (e.g., proteins and antibodies), examples of which are provided herein, as well as stem cells. Methods or therapies that can be used in combination with the administration of the compound provided herein include, but are not limited to, surgery, blood transfusions, immunotherapy, biological therapy, radiation therapy, and other non-drug based therapies presently used to treat, prevent or manage disease and conditions associated with or characterized by undesired angiogenesis.

In one embodiment, the additional active agent is selected from the group consisting of an alkylating agent, an adenosine analog, a glucocorticoid, a kinase inhibitor, a SYK inhibitor, a PDE3 inhibitor, a PDE7 inhibitor, doxorubicin, chlorambucil, vincristine, bendamustine, forskolin, rituximab, or a combination thereof.

In one embodiment, the additional active agent is rituximab. In another embodiment, the additional active agent is prednisone.

In one embodiment, the glucocorticoid is hydrocortisone. In one embodiment, the glucocorticoid is dexamethasone.

In certain embodiments, a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered to patients with relapsed or refractory multiple myeloma in combination with doxorubicin (Doxil®), vincristine and/or dexamethasone (Decadron®). In one embodiment, the compound is administered in combination with dexamethasone.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); anti-CD38 drugs (such as, for example, Daratumumab); histone deacetlyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, anticancer agents and antibiotics (e.g., clarithromycin).

In certain embodiments, a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered in combination with a chimeric antigen receptors or chimeric T cell receptors or CAR-T cells. CD19, CD22, CD123 and BCMA have all been made targets of CAR T cells. In certain embodiments, a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered in combination with one or more checkpoint inhibitor(s). In one embodiment, combination therapies described herein include one checkpoint inhibitor administered in combination with a compound described herein. In another embodiment, combination therapies described herein include two checkpoint inhibitors administered in combination with a compound described herein. In yet another embodiment, combination therapies described herein include three or more checkpoint inhibitors administered in combination with a compound described herein in connection with methods provided herein. In still another embodiment combination therapies described herein include one checkpoint inhibitor administered in combination with one or more secondary active agents described herein. Also contemplated herein is administration of one or more checkpoint inhibitor administered in combination with a compound described herein and a second therapeutic agent as described herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, *Nature Reviews Cancer*, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one aspect, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™. Accordingly, provided herein are combination therapies that include one or more CTLA-4 inhibitors and a compound as described herein. In certain instances, the combination therapy includes tremelimumab (ticilimumab or CP-675, 206) and a compound as described herein. The combination therapy can include ipilimumab (MDX-010 or MDX-101) and a compound as described herein. Such combination therapies can include CTLA-4 inhibitors and compounds described herein at concentrations and amounts as set forth herein.

In another aspect, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating AML at relapse. In yet another embodiment, the anti-PD-1 antibody is AMP-224, a fusion protein.

Accordingly, provided herein are combination therapies that include a PD-1 inhibitor and a compound as described herein. In one embodiment is a combination therapy that includes an anti-PD-1 antibody and a compound as described herein. In another embodiment is a combination therapy that includes nivolumab (ONO-4538, BMS-936558, and MDX1106) and a compound as described herein. In yet another embodiment is a combination therapy that includes pembrolizumab and a compound as described herein. In still another embodiment is a combination therapy that includes CT-011 and a compound as described herein. In yet another embodiment is a combination therapy that includes AMP-224 and a compound as described herein. Such embodiments that include PD-1 inhibitors and compounds as described herein at concentrations and amounts as set forth herein.

In another aspect, the checkpoint inhibitor is a PD-L1 inhibitor. In one embodiment, the PD-L1 inhibitor is an anti-PD-L1 antibody. In one embodiment, the anti-PD-L1 antibody is durvalumab (MEDI4736). In another embodiment, the anti-PD-L1 antibody is BMS-936559 (also known as MDX-1105-01). Accordingly, provided herein are combination therapies that include a PD-L1 inhibitor and a compound as described herein. In one embodiment is a combination therapy that includes durvalumab and a compound as described herein. In another embodiment is a combination therapy that includes BMS-936559 (MDX-1105-1) and a compound as described herein. Such embodiments include PD-L1 inhibitors and compounds as described herein at concentrations and amounts as set forth herein. In still another embodiment, the combination includes a PD-L1 antibody such as durvalumab in combination with one or more secondary active agents described herein.

In still another aspect, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A. Thus, provided herein are combination therapies that include an anti-PD-L2 inhibitor as described herein and a compound as described herein. In one embodiment is a combination therapy that includes rHIgM12B7A and a compound as described herein. Such embodiments include PD-L2 inhibitors and compounds as described herein at concentrations and amounts as set forth herein.

In still another aspect, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016. Thus, provided herein are combination therapies that include a LAG-3 inhibitor as described herein and a compound as described herein. In one embodiment is a combination therapy that includes IMP321 and a compound as described herein. In another embodiment is a combination therapy that includes BMS-986016 and a compound as described herein. Such embodiments include LAG-3 inhibitors and compounds as described herein at concentrations and amounts as set forth herein.

In yet another aspect, the checkpoint inhibitor is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834). Thus, provided herein are combination therapies that include a B7 inhibitor and a compound described herein. In one embodiment is a combination therapy that includes B7-H3 inhibitor as described herein and a compound as described herein. In another embodiment is a combination therapy that includes a B7-H4 inhibitor as described herein and a compound as described herein. In still another embodiment is a combination therapy that includes MGA271 and a compound as described herein. Such embodiments include a B7 inhibitor as described herein and a compound as described herein at concentrations and amounts as set forth herein.

In another aspect, the checkpoint inhibitors is a TIM-3 (T-cell immunoglobulin domain and mucin domain 3) inhibitor (Fourcade et al., *J. Exp. Med.*, 2010, 207, 2175-86; Sakuishi et al., *J. Exp. Med.*, 2010, 207, 2187-94). Accordingly, in one embodiment is a combination therapy that includes a TIM-3 inhibitor and a compound as described herein, at concentrations and amounts as set forth herein.

In another aspect, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469. Accordingly, in one embodiment is a combination therapy that includes an OX40 agonist and a compound as described herein. In another embodiment is a combination therapy that includes an anti-OX40 antibody and a compound a described herein. In still another embodiment is a combination therapy that includes anti-OX-40 and a compound as described herein. In yet another embodiment is a combination therapy that includes MEDI6469 and a compound as described herein. Such embodiments include OX40 agonists and compounds, as described herein, at concentrations and amounts as set forth herein.

In still another aspect, the checkpoint inhibitor is a GITR agonist. In one embodiment, the checkpoint inhibitor is an anti-GITR antibody. In one embodiment, the anti-GITR antibody is TRX518. Thus provided herein are combination therapies that include a GITR agonist and a compound as described herein. In one embodiment is a combination therapy that includes an anti-GITR antibody and a compound as described herein. In another embodiment is a combination therapy that includes TRX518 and a compound as described herein. Such embodiments include GITR agonists and compounds, as described herein, at concentrations and amounts as set forth herein.

In yet another aspect, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566. Provided herein are combination therapies that include a CD137 agonist and a compound as described herein. In one embodiment is a combination therapy that includes an anti-CD137 antibody and a compound as described herein. In another embodiment is a combination therapy that includes urelumab and a compound as described herein. In still another embodiment is a combination therapy that includes PF-05082566 and a compound as described herein. Such embodiments include CD137 agonists and compounds, as described herein, at concentrations and amounts as set forth herein.

In another aspect, the checkpoint inhibitor is a CD40 agonist. In one embodiment, the checkpoint inhibitor is an anti-CD40 antibody. In one embodiment, the anti-CD40 antibody is CF-870,893. Provided herein are combination therapies that include a CD40 agonist and a compound as described herein. In one embodiment is a combination therapy that includes an anti-CD40 antibody and a compound as described herein. In another embodiment is a combination therapy that includes CF-870,893 and a compound as described herein. Such embodiments include CD40 agonists and compounds, as described herein, at concentrations and amounts as set forth herein.

In yet another aspect, the checkpoint inhibitor is recombinant human interleukin-15 (rhIL-15). Thus, in one embodiment is a combination therapy that includes rhIL-15 and a compound as described herein at concentrations and amounts as set forth herein.

In another aspect, the checkpoint inhibitor is an IDO inhibitor. In one embodiment, the IDO inhibitor is INCB024360. In another embodiment, the IDO inhibitor is indoximod. Thus provided herein are combination therapies that include an IDO inhibitor as described herein and a compound as described herein. In one embodiment is a combination therapy that includes INCB024360 and a compound as described herein. In another embodiment is a combination therapy that includes indoximod and a compound as described herein. Such embodiments include an IDO inhibitor and a compound, as described herein, in concentrations and amounts as set forth herein.

In certain embodiments, the above described combination therapies can include two or more of the checkpoint inhibitors described herein (including checkpoint inhibitors of the same or different class). Moreover, the combination therapies described herein (e.g., a compound described herein and one or more checkpoint inhibitors) can be used in combination with another active agents as described herein where appropriate for treating diseases described herein and understood in the art. In one embodiment, the another active agent is a steroid. In one embodiment, the another active agent is a corticosteroid. In one embodiment, the another active agent is dexamethasone.

In certain embodiments, a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered in combination with one or more checkpoint inhibitor(s), and further in combination with dexamethasone.

Specific second active compounds that can be combined with compounds provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin;

cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Administration of a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One of administration for compounds provided herein is oral. Routes of administration for the second active agents or ingredients are known to those of ordinary skill in the art. See, e.g., *Physicians' Desk Reference* (60$^{th}$ ed., 2006).

In certain embodiments, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

Use with Transplantation Therapy

The compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, provided herein can be used to reduce the risk of Graft Versus Host Disease (GVHD). Therefore, encompassed herein is a method of treating, preventing and/or managing cancer, which comprises administering the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, provided herein and transplantation therapy provides a unique and unexpected synergism. In particular, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, exhibits immunomodulatory activity that may provide additive or synergistic effects when given concurrently with transplantation therapy in patients with cancer.

The compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, can work in combination with transplantation therapy reducing complications associated with the invasive procedure of transplantation and risk of GVHD. Encompassed herein is a method of treating, preventing and/or managing cancer which comprises administering to a patient (e.g., a human) the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered to patients with multiple myeloma before, during, or after the transplantation of autologous peripheral blood progenitor cell.

In another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered to patients with relapsing multiple myeloma after the stem cell transplantation.

In yet another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, and prednisone are administered as maintenance therapy to patients with multiple myeloma following the transplantation of autologous stem cell.

In yet another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, and dexamethasone are administered as salvage therapy for low risk post transplantation to patients with multiple myeloma.

In yet another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, and dexamethasone are administered as maintenance therapy to patients with multiple myeloma following the transplantation of autologous bone marrow.

In yet another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered following the administration of high dose of melphalan and the transplantation of autologous stem cell to patients with chemotherapy responsive multiple myeloma.

In yet another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, and PEG INTRO-A are administered as maintenance therapy to patients with multiple myeloma following the transplantation of autologous CD34-selected peripheral stem cell.

In yet another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered with post transplant consolidation chemotherapy to patients with newly diagnosed multiple myeloma to evaluate anti-angiogenesis.

In still another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, and dexamethasone are administered as maintenance therapy after DCEP consolidation, following the treatment with high dose of melphalan and the transplantation of peripheral blood stem cell to 65 years of age or older patients with multiple myeloma.

In one embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered to patients with NHL (e.g., DLBCL) before, during, or after the transplantation of autologous peripheral blood progenitor cell.

In another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered to patients with NHL (e.g., DLBCL) after a stem cell transplantation.

Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, provided herein is administered daily in a single or divided doses in a four to six week cycle with a rest period of about a week or two weeks. The cycling method further allows the frequency, number, and length of dosing cycles to be increased. Thus, encompassed herein in certain embodiments is the administration of a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, for more cycles than are typical when it is administered alone. In certain embodiments, a compound provided herein, e.g., the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered for a greater number of cycles that would typically cause dose-limiting toxicity in a patient to whom a second active ingredient is not also being administered.

In one embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, is administered daily and continuously for three or four weeks at a dose of from about 0.1 to about 150 mg/d followed by a break of one or two weeks.

In another embodiment, the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, and a second active ingredient are administered orally, with administration of the compound of Formula I occurring 30 to 60 minutes prior to a second active ingredient, during a cycle of four to six weeks. In certain embodiments, the combination of the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, and a second active ingredient is administered by intravenous infusion over about 90 minutes every cycle. In certain embodiments, one cycle comprises the administration from about 0.1 to about 150 mg/day of the compound of Formula (I), or an isotopologue thereof, or an enantiomer or a mixture of enantiomers thereof, or a pharmaceutically acceptable salt, solvate (e.g., hydrate), prodrug, clathrate, polymorph, or co-crystal thereof, and from about 50 to about 200 mg/m$^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are described above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., Remington's Pharmaceutical Sciences, 18th ed., Mack Publishing, Easton Pa. (1990).

In certain embodiments, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In certain embodiments, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in certain embodiments, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In certain embodiments, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In certain embodiments, oral dosage forms are tablets or capsules, in which case solid excipients are employed. In certain embodiments, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in certain embodiments, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In certain embodiments, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In certain embodiments, a solid oral dosage form comprises a compound provided herein, anhydrous lactose, microcrystalline cellulose, polyvinylpyrrolidone, stearic acid, colloidal anhydrous silica, and gelatin.

Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In certain embodiments, provided are single unit dosage forms suitable for oral administration such as, but not limited to, tablets, capsules, gelcaps, and caplets that are adapted for controlled-release.

In certain embodiments, controlled-release pharmaceutical products improve drug therapy over that achieved by their non-controlled counterparts. In certain embodiments, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In certain embodiments, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In certain embodiments, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenternal Dosage Forms

Parenteral dosage forms can be administered to patients by various routes including, but not limited to, subcutaneous, intravenous (including bolus injection), intramuscular, and intraarterial. In certain embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In certain embodiments, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences*, 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

Kits

In certain embodiments, active ingredients provided herein are not administered to a patient at the same time or by the same route of administration. In certain embodiments, provided are kits which can simplify the administration of appropriate amounts of active ingredients.

In certain embodiments, a kit comprises a dosage form of a compound provided herein. Kits can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those provided herein.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); M (molar); mM (millimolar); µM (micromolar); eq. (equivalent); mmol (millimoles); Hz (Hertz); MHz (megahertz); hr or hrs (hour or hours); min (minutes); and MS (mass spectrometry). Unless otherwise specified, the water content in a compound provided herein is determined by Karl Fisher (KF) method.

For all of the following examples, unless otherwise specified, standard work-up and purification methods known to those skilled in the art can be utilized. Unless otherwise specified, all temperatures are expressed in ° C. (degrees Centigrade). All reactions were conducted at room temperature unless otherwise noted. Synthetic methodologies illustrated herein are intended to exemplify the applicable chemistry through the use of specific examples and are not indicative of the scope of the disclosure.

General Synthetic Scheme

In one embodiment, Compound I-S and its deuterium isotopologues can be prepared according to the following reaction scheme:

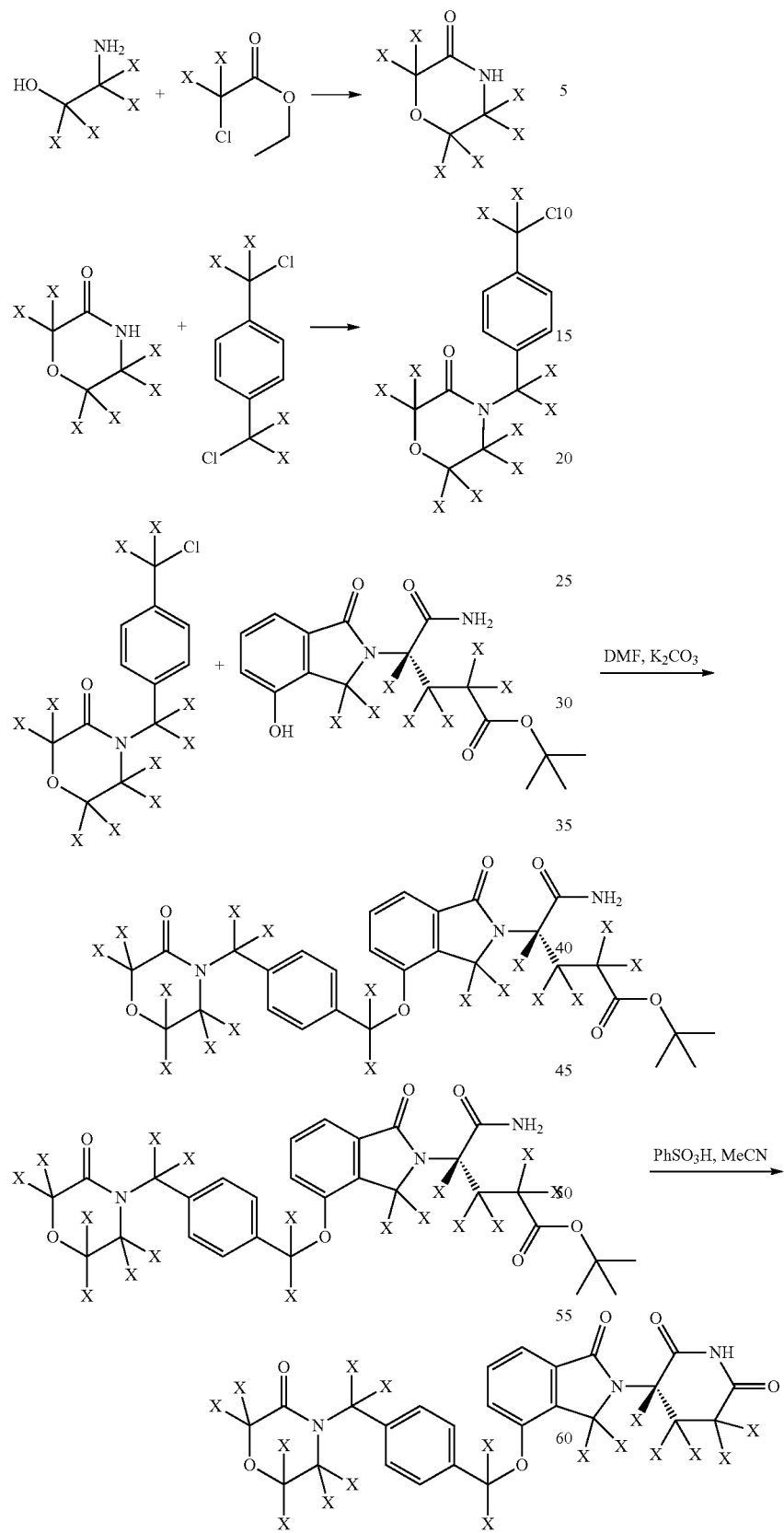
X = H or D

It would be understood by a skilled artisan that additional isotopologues can be prepared when corresponding deuterium-enriched starting materials are used (e.g., deuterium-enriched on the phenyl moiety). Racemic starting material, intermediate, or products can also be separated by chiral separation or other chiral resolution techniques to provide the corresponding enantiomers.

Example 1 Preparation of Compound I-S

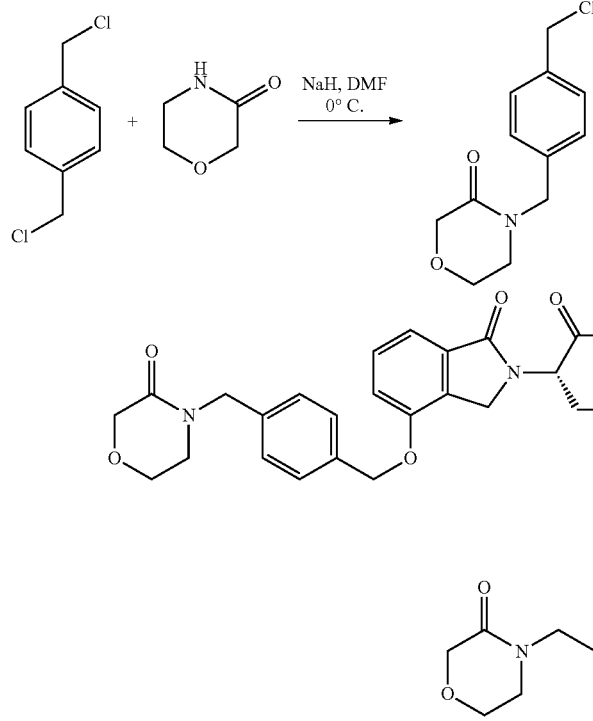

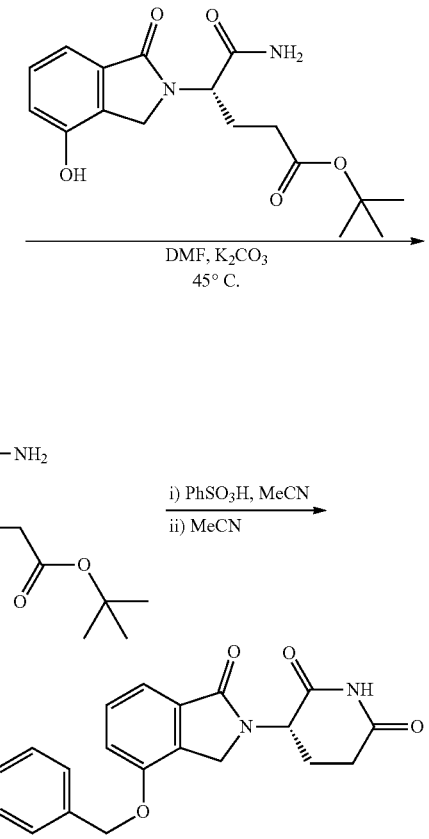

Step 1: Preparation of 4-(4-(chloromethyl)benzyl)morpholin-3-one

A 250-mL three-necked round-bottomed flask equipped with stir bar was charged with DMF (60 mL) and sodium hydride (1.4 g, 36 mmol). The mixture was cooled to 0° C. and morpholin-3-one (3.0 g, 30 mmol) was charged. After gas evolution stopped, 1,4-bis(chloromethyl)benzene (6.2 g, 36 mmol) was charged in one portion. The reaction mixture was warmed up to 20° C. and stirred at 20° C. for 19 hours. The reaction was quenched with HCl (1N, 36 mL), water was added (24 mL), and the mixture was extracted with ethyl acetate (120 mL×3). The combined organic layers were washed with water (60 mL×3) and brine (60 mL). The organic phase was dried over magnesium sulfate and filtered. The filtrate was evaporated to dryness. The residue was purified by chromatography (120 g silica gel column, eluted with DCM-10% MeOH in DCM, gradient: 0-10% in 40 min.) to provide the title compound (1.5 g, 21% yield). $^1$H NMR (300 MHz, DMSO-$d_6$) δ 3.25 (t, J=5.2 Hz, 2H, CH$_2$), 3.73-3.90 (m, 2H, CH$_2$), 4.12 (s, 2H, CH$_2$), 4.55 (s, 2H, CH$_2$), 4.75 (s, 2H, CH$_2$), 7.27 (d, J=7.9 Hz, 2H, Ar), 7.42 (d, J=8.1 Hz, 2H, Ar).

Step 2: Preparation of (S)-tert-butyl 5-amino-5-oxo-4-(1-oxo-4-((4-((3-oxomorpholino)methyl)benzyl)oxy)isoindolin-2-yl)pentanoate To a 40 mL reaction vial equipped with stir bar was charged 4-(4-(chloromethyl)benzy-1)morpholin-3-one (1.00 g, 4.17 mmol), (S)-tert-butyl 5-amino-4-(4-hydroxy-1-oxoisoindolin-2-yl)-5-oxopentanoate (1.40 g, 4.17 mmol), potassium carbonate (1.44 g, 10.43 mmol) and N,N-dimethylformamide (8.34 mL). The reaction mixture was heated at 45° C. for 18 hours and then cooled to 20° C. 50 mL of ethyl acetate and 10 mL of water were added sequentially and the mixture was stirred for 5 min. The organic layer was separated and washed with water (5 mL×4), brine (5 mL), dried over magnesium sulfate and filtered. The filtrate was evaporated to dryness to provide the title compound as a foam like solid (2.2 g, yield 98%). The product was used in next step without further purification. $^1$H NMR (300 MHz, DMSO-$d_6$) δ 1.32 (s, 9H, CH$_3$), 1.94-2.23 (m, 4H, CH$_2$, CH$_2$), 3.23-3.30 (m, 2H, CH$_2$), 3.82 (t, J=5.1 Hz, 2H, CH$_2$), 4.12 (s, 2H, CH$_2$), 4.34-4.60 (m, 4H, CH$_2$, CH$_2$), 4.71 (dd, J=4.1, 10.1 Hz, 1H, CH), 5.23 (s, 2H, CH$_2$), 7.18 (br. s., 1H, NH), 7.30 (dd, J=1.9, 7.9 Hz, 4H, Ar), 7.40-7.52 (m, 3H, Ar), 7.56 (br. s., 1H, NH).

Step 3: Preparation of (S)-3-(1-oxo-4-((4-((3-oxo-morpholino)methyl)benzyl)oxy)isoindolin-2-yl)piperidine-2,6-dione (Compound I-S)

To a 50 mL jacket flask equipped with stir bar and distillation apparatus charge (S)-tert-butyl 5-amino-5-oxo-4-(1-oxo-4-(4-((3-oxomorpholino)methyl)benzyloxy)isoindolin-2-yl) pentanoate (1 g, 1.860 mmol) in acetonitrile (30 mL) and benzenesulfonic acid (0.088 g, 0.558 mmol). The jacket was heated to 92° C. and the mixture was distilled under a nitrogen sweep. After 10 mL of acetonitrile had distilled, additional acetonitrile was charged to maintain a constant volume at 20× (Vol.). The reaction was monitored by HPLC to until reaching the endpoint (uncyclized intermediate NMT 2% relative to product). The reaction mixture was distilled to 10×, and then cooled to 20° C. overnight. The precipitate was filtered and the cake was washed with acetonitrile (5 mL×2) to provide crude product as off white solid. Two batches were conducted and net 1.1 g product was obtained, with an average yield 64%. Batch 1, 0.51 g, yield 59%; Batch 2, 0.59 g, yield 69%. $^1$H NMR (300 MHz, DMSO-$d_6$) δ 1.92-2.06 (m, 1H, CHH), 2.43 (d, J=4.3 Hz, 1H, CHH), 2.55-2.68 (m, 1H, CHH), 2.80-3.04 (m, 1H, CHH), 3.26 (t, J=5.1 Hz, 2H, CH$_2$), 3.81 (t, J=5.1 Hz, 2H, CH$_2$), 4.11 (s, 2H, CH$_2$), 4.19-4.48 (m, 2H, CH$_2$), 4.55 (s, 2H, CH$_2$), 5.11 (dd, J=5.0, 13.1 Hz, 1H, CH), 5.24 (s, 2H, CH$_2$), 7.31 (dd, J=7.9, 11.1 Hz, 4H, ArH), 7.42-7.54 (m, 3H, ArH), 10.97 (s, 1H, NH).

To a 50 mL jacket European style flask equipped with stir bar was charged the crude product (1.1 g, 2.37 mmol) and acetonitrile (11 mL, 10×). The mixture was heated to reflux for 30 minutes, the cloudy mixture was cooled to 20° C. in 2 hour and then stirred at 20° C. for 1 hour. The solid was filtered, washed with acetonitrile (3×5 mL) and dried under vacuum at 40° C. overnight to provide 0.96 g the title compound product as white solid, in 87% yield. Elemental Analysis: Calcd: $C_{25}H_{25}N_3O_6$+0.8H$_2$O C, 62.83; H, 5.61; N, 8.79. Found: C, 62.90; H, 5.56: N, 8.89. KF 4.95%. $^1$H NMR (300 MHz, DMSO-$d_6$) δ 1.92-2.06 (m, 1H, CHH), 2.43 (d, J=4.3 Hz, 1H, CHH), 2.55-2.68 (m, 1H, CHH), 2.80-3.04 (m, 1H, CHH), 3.26 (t, J=5.1 Hz, 2H, CH$_2$), 3.81 (t, J=5.1 Hz, 2H, CH$_2$), 4.11 (s, 2H, CH$_2$), 4.19-4.48 (m, 2H, CH$_2$), 4.55 (s, 2H, CH$_2$), 5.11 (dd, J=5.0, 13.1 Hz, 1H, CH), 5.24 (s, 2H, CH$_2$), 7.31 (dd, J=7.9, 11.1 Hz, 4H, ArH), 7.42-7.54 (m, 3H, ArH), 10.97 (s, 1H, NH). $^{13}$C NMR (75 MHz, DMSO-$d_6$): δ 22.36, 31.20, 45.09, 45.59, 48.25, 51.59, 63.21, 67.40, 69.31, 114.98, 115.26, 127.83, 128.02, 129.82, 129.97, 133.32, 135.67, 136.66, 153.47, 166.07, 167.99, 170.96, 172.82.

Example 2

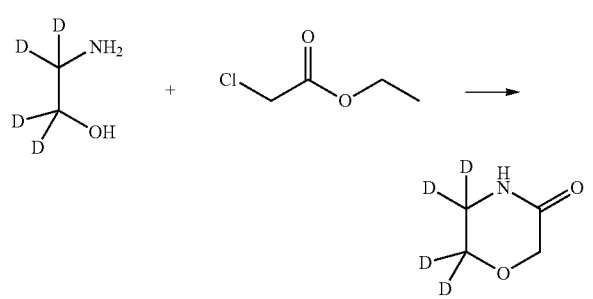

Small pieces of sodium is added to a solution of 2-amino ($^2$H4)ethan-1-ol (0.10 mol) in i-PrOH (100 mL). The mixture is heated at 50° C., and then cooled in an ice-water bath. Ethyl chloroacetate (0.09 mol) is added at 0° C. The mixture is heated at 80° C. The product is purified by column chromatograph to provide (5,5,6,6-$^2$H4)morpholin-3-one.

Example 3

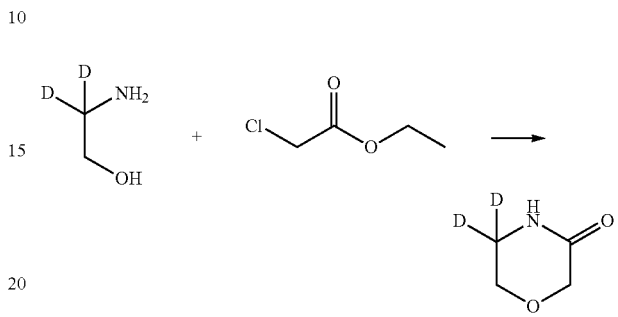

Small pieces of sodium is added to a solution of 2-amino (2,2-$^2$H$_2$)ethan-1-ol (0.10 mol) in i-PrOH (100 mL). The mixture is heated at 50° C., and then cooled in an ice-water bath. Ethyl chloroacetate (0.09 mol) is added at 0° C. The mixture is heated at 80° C. The product is purified by column chromatograph to provide (5,5-$^2$H$_2$)morpholin-3-one.

Example 4

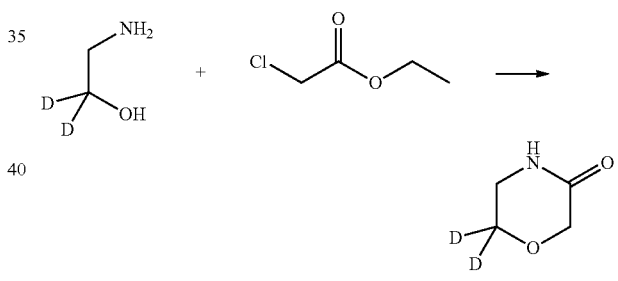

Small pieces of sodium is added to a solution of 2-amino (1,1-$^2$H$_2$)ethan-1-ol (0.10 mol) in i-PrOH (100 mL). The mixture is heated at 50° C., and then cooled in an ice-water bath. Ethyl chloroacetate (0.09 mol) is added at 0° C. The mixture is heated at 80° C. The product is purified by column chromatograph to provide (6,6-$^2$H$_2$)morpholin-3-one.

Example 5

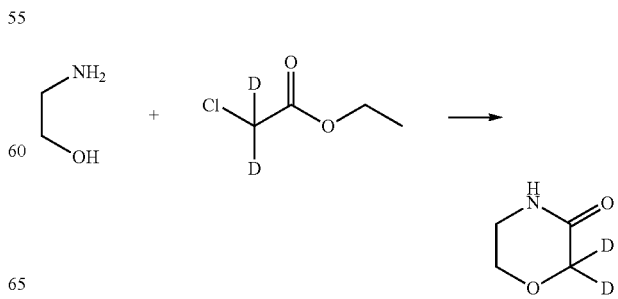

Small pieces of sodium is added to a solution of ethanol amine (0.10 mol) in i-PrOH (100 mL). The mixture is heated at 50° C., and then cooled in an ice-water bath. Ethyl chloro($^2$H$_2$)acetate (0.09 mol) (Stack et al., *Journal of the American Chemical Society*, 112(7), 1990, 2716-29) is added at 0° C. The mixture is heated at 80° C. The product is purified by column chromatograph to provide (2,2-$^2$H$_2$) morpholin-3-one.

Example 6

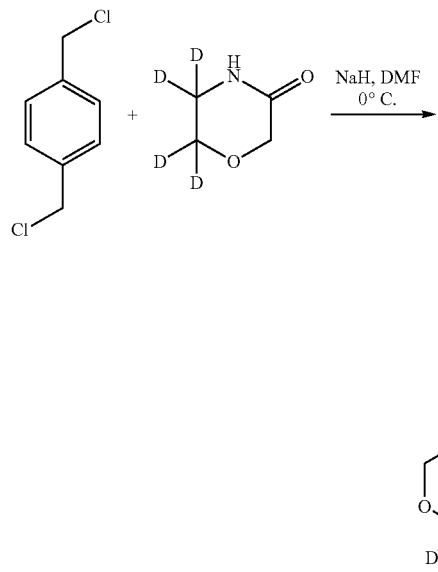

The mixture of sodium hydride (36 mmol) in DMF (60 mL) is cooled to 0° C. To the solution is charged 5,5,6,6-d$_4$-morpholin-3-one (30 mmol). 1,4-bis(chloromethyl)benzene (36 mmol) is charged. The reaction mixture is warmed to 20° C. and stirred at 20° C. The reaction is quenched with HCl (1N, 36 mL) and water (24 mL). The mixture is extracted with ethyl acetate (120 mL×3). The combined organic layers are washed with water (60 mL×3) and brine (60 mL). The organic phase is dried over magnesium sulfate and filtered. The filtrate is evaporated to dryness. The residue is purified by chromatograph (120 g silica gel column) to provide 5,5,6,6-d$_4$-4-((4-(chloromethyl-d$_2$)phenyl)methyl-d$_2$)-morpholin-3-one.

Example 7

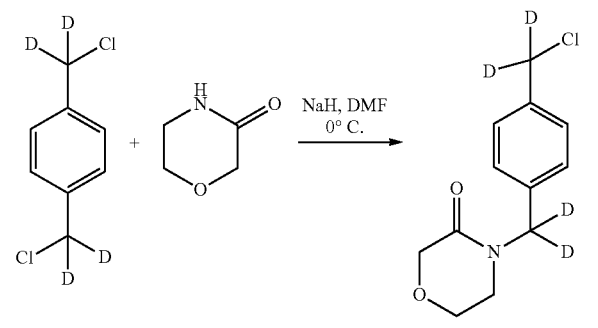

The mixture of sodium hydride (36 mmol) in DMF (60 mL) is cooled to 0° C. To the solution is charged morpholin-3-one (30 mmol). 1,4-Bis[chloro($^2$H$_2$)methyl]benzene (36 mmol) (Holland et al., *Journal of the Chemical Society, Perkin Transactions* 2. *Physical Organic Chemistry*, 10, 1990, 1651-5) is charged to the mixture. The reaction mixture is warmed to 20° C. and stirred at 20° C. The reaction is quenched with HCl (1N, 36 mL) and water (24 mL). The mixture is extracted with ethyl acetate. The combined organic layers is washed with water and brine. The organic phase is dried over magnesium sulfate and filtered. The filtrate is evaporated to dryness. The residue is purified by chromatograph to provide 4-[{4-[chloro($^2$H$_2$) methyl]phenyl}($^2$H$_2$)methyl]morpholin-3-one.

Example 8

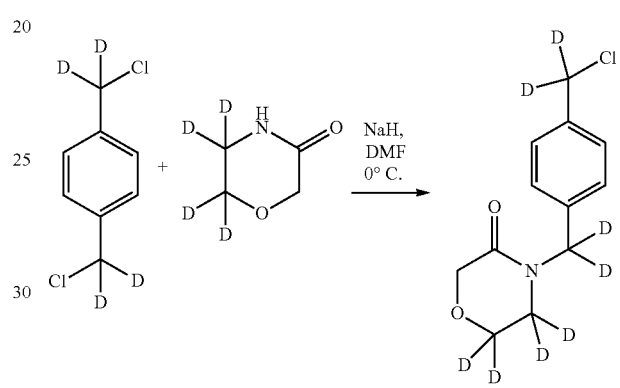

The mixture of sodium hydride (36 mmol) in DMF (60 mL) is cooled to 0° C. To the solution is charged (5,5,6,6-$^2$H$_4$)morpholin-3-one (30 mmol). 1,4-Bis[chloro($^2$H$_2$) methyl]benzene (36 mmol) (Holland et al., *Journal of Chemical Society, Perkin Transactions* 2: *Physical Organic Chemistry*, 10, 1990, 1651-5) is charged to the mixture. The reaction mixture is warmed to 20° C. and stirred at 20° C. The reaction is quenched with HCl (1N, 36 mL) and water (24 mL). The mixture is extracted with ethyl acetate. The combined organic layers is washed with water and brine. The organic phase is dried over magnesium sulfate and filtered. The filtrate is evaporated to dryness. The residue is purified by chromatograph to provide 4-[{4-[chloro($^2$H$_2$) methyl]phenyl}($^2$H$_2$)methyl](5,5,6,6-$^2$H$_4$)morpholin-3-one.

Example 9

The following analogs are prepared using the method in Example 6-8.

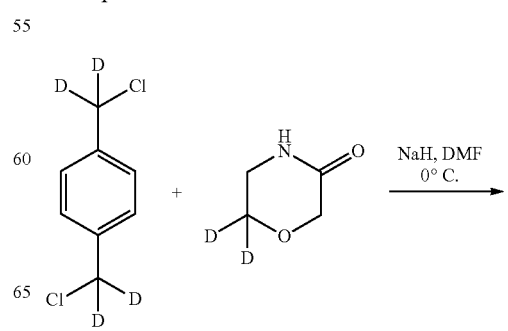

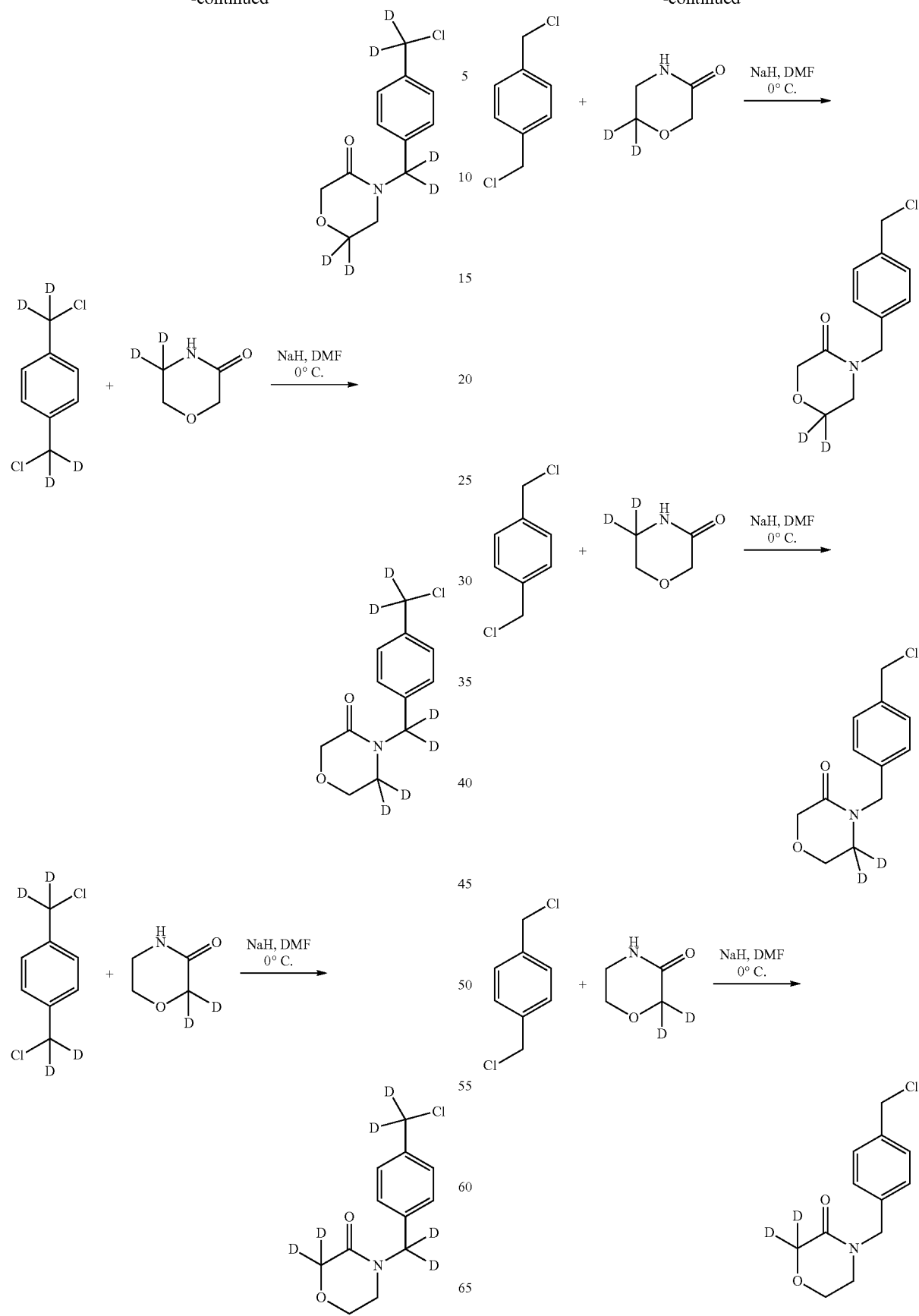

Example 10

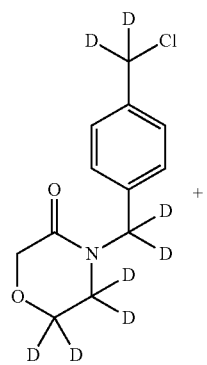

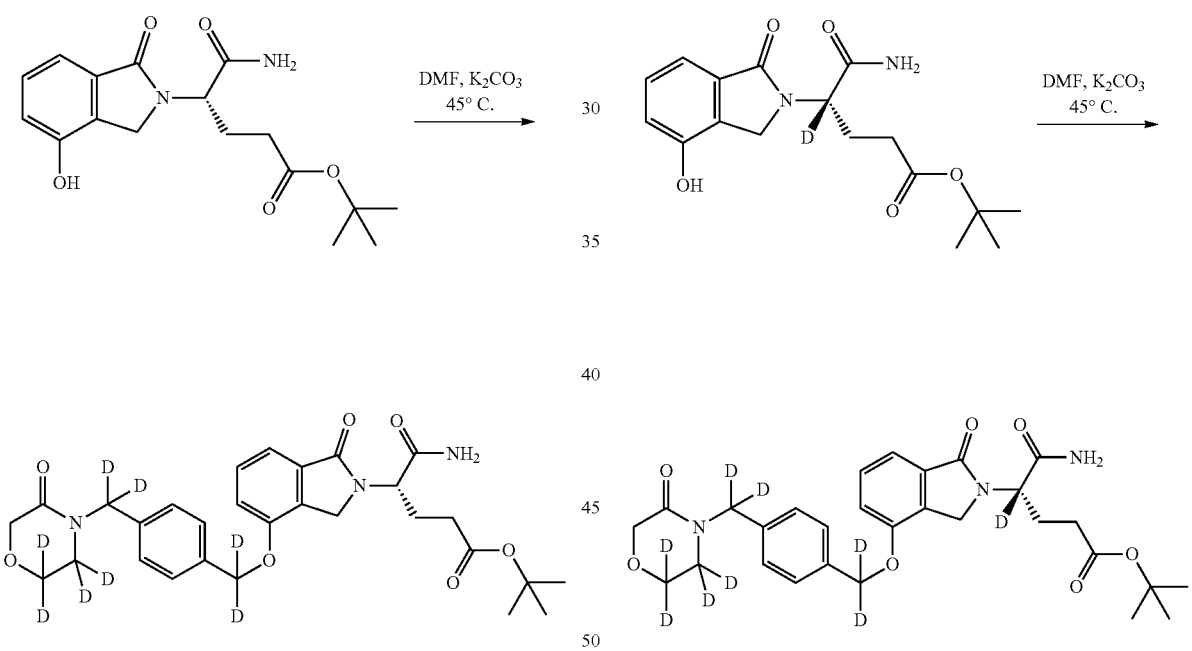

A solution of 4-[{4-[chloro($^2H_2$)methyl]phenyl}($^2H_2$)methyl](5,5,6,6-$^2H_4$)morpholin-3-one (1.00 g), tert-butyl (4S)-5-amino-4-(4-hydroxy-1-oxo-1,3-dihydro-2H-isoindol-2-yl)-5-oxopentanoate (1.40 g), potassium carbonate (1.44 g) and N,N-dimethylformamide is heated at 45° C. for 18 hours and then cooled to 20° C. Ethyl acetate and water is added. The organic layer is washed with water, brine, dried over magnesium sulfate and filtered. The filtrate is evaporated to dryness and purified by chromatograph to provide tert-butyl (4S)-5-amino-5-oxo-4-(1-oxo-4-{[(4-{[3-oxo(5,5,6,6-$^2H_4$)morpholin-4-yl]($^2H_2$)methyl}phenyl)($^2H_2$)methyl]oxy}-1,3-dihydro-2H-isoindol-2-yl)pentanoate.

Example 11

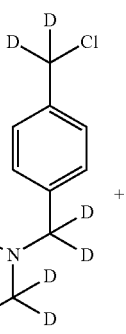

A solution of 4-[{4-[chloro($^2H_2$)methyl]phenyl}($^2H_2$)methyl](5,5,6,6-$^2H_4$)morpholin-3-one (1.00 g), tert-butyl (4S)-5-amino-4-(4-hydroxy-1-oxo-1,3-dihydro-2H-isoindol-2-yl)-5-oxo(4-2H)pentanoate (1.40 g), potassium carbonate (1.44 g) and N,N-dimethylformamide is heated at 45° C. for 18 hours and then cooled to 20° C. Ethyl acetate and water is added. The organic layer is washed with water, brine, dried over magnesium sulfate and filtered. The filtrate is evaporated to dryness and purified by chromatograph to provide tert-butyl (4S)-5-amino-5-oxo-4-(1-oxo-4-{[(4-{[3-oxo(5,5,6,6-$^2H_4$)morpholin-4-yl]($^2H_2$)methyl}phenyl)($^2H_2$)methyl]oxy}-1,3-dihydro-2H-isoindol-2-yl)(4-$^2H$)pentanoate.

Example 12

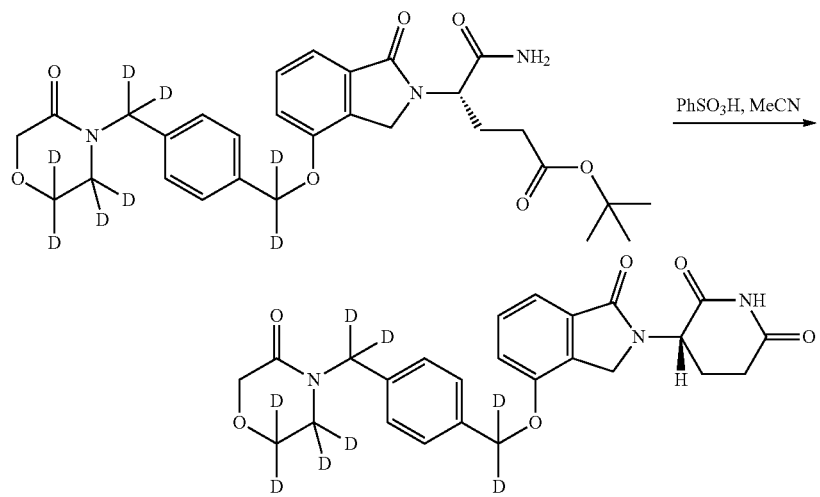

The mixture of tert-butyl (4S)-5-amino-5-oxo-4-(1-oxo-4-{[(4-{[3-oxo(5,5,6,6-$^2$H$_4$)morpholin-4-yl]($^2$H$_2$)methyl}phenyl)($^2$H$_2$)methyl]oxy}-1,3-dihydro-2H-isoindol-2-yl)pentanoate (1.860 mmol) in acetonitrile (30 mL) and benzenesulfonic acid (0.558 mmol) is heated to 92° C. The mixture is distilled under a nitrogen sweep. Additional acetonitrile is charged to maintain a constant volume at 20× (Vol.). The reaction mixture is cooled to 20° C. The residue is purified by chromatograph (silica gel column) to provide (3S)-3-(1-oxo-4-{[(4-{[3-oxo(5,5,6,6-$^2$H$_4$)morpholin-4-yl]($^2$H$_2$)methyl}phenyl)($^2$H$_2$)methyl]oxy}-1,3-dihydro-2H-isoindol-2-yl)piperidine-2,6-dione.

Example 13

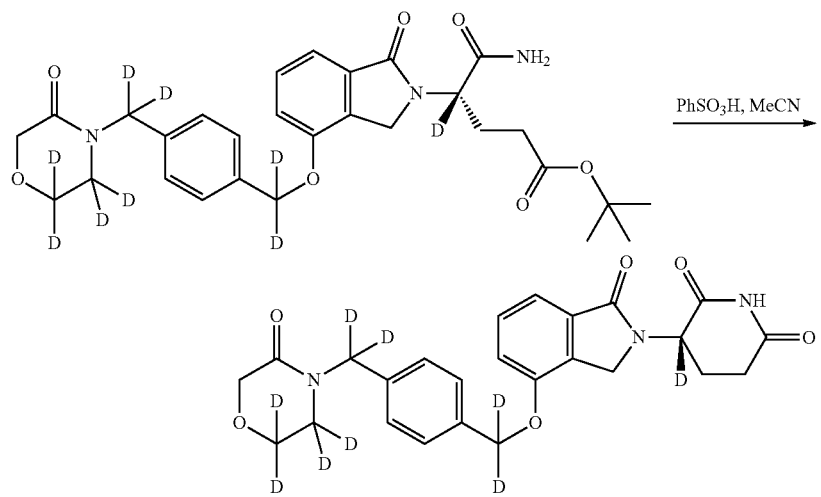

The mixture of tert-butyl (4S)-5-amino-5-oxo-4-(1-oxo-4-{[(4-{[3-oxo(5,5,6,6-$^2$H$_4$)morpholin-4-yl]($^2$H$_2$)methyl}phenyl)($^2$H$_2$)methyl]oxy}-1,3-dihydro-2H-isoindol-2-yl)(4-$^2$H)pentanoate (1.860 mmol) in acetonitrile (30 mL) and benzenesulfonic acid (0.558 mmol) is heated to 92° C. The mixture is distilled under a nitrogen sweep. Additional acetonitrile is charged to maintain a constant volume at 20× (Vol.). The reaction mixture is cooled to 20° C. The residue is purified by chromatograph (silica gel column) to provide (3S)-3-(1-oxo-4-{[(4-{[3-oxo(5,5,6,6-$^2$H$_4$)morpholin-4-yl]($^2$H$_2$)methyl}phenyl)($^2$H$_2$)methyl]oxy}-1,3-dihydro-2H-isoindol-2-yl)(3-$^2$H)piperidine-2,6-dione.

Example 14 Assays

TNFα Inhibition Assay in hPMBC

Human peripheral blood mononuclear cells (hPBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bio-products, Woodland, Calif., USA), 2 mM L-glutamine, 100 U/ml penicillin, and 100 µg/ml streptomycin (Life Technologies).

PBMC (2×10$^5$ cells) are plated in 96-well flat-bottom Costar tissue culture plates (Corning, N.Y., USA) in triplicate. Cells are stimulated with LPS (from *Salmonella abortus equi*, Sigma cat. no. L-1887, St. Louis, Mo., USA) at 1 ng/ml final in the absence or presence of compounds. Compounds provided herein are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% $CO_2$, and supernatants are then collected, diluted with culture medium and assayed for TNFα levels by ELISA (Endogen, Boston, Mass., USA). $IC_{50}$s are calculated using non-linear regression, sigmoidal dose-response, constraining the top to 100% and bottom to 0%, allowing variable slope (GraphPad Prism v3.02).

IL-2 and MIP-3α Production by T Cells

PBMC are depleted of adherent monocytes by placing $1\times10^8$ PBMC in 10 ml complete medium (RPMI 1640 supplemented with 10% heat-inactivated fetal bovine serum, 2 mM L-glutamine, 100 U/ml penicillin, and 100 µg/ml streptomycin) per 10 cm tissue culture dish, in 37° C., 5% $CO_2$ incubator for 30-60 minutes. The dish is rinsed with medium to remove all non-adherent PBMC. T cells are purified by negative selection using the following antibody (Pharmingen) and Dynabead (Dynal) mixture for every $1\times10^8$ non-adherent PBMC: 0.3 ml Sheep anti-mouse IgG beads, 15 µl anti-CD16, 15 µl anti-CD33, 15 µl anti-CD56, 0.23 ml anti-CD19 beads, 0.23 ml anti-HLA class II beads, and 56 µl anti-CD14 beads. The cells and bead/antibody mixture is rotated end-over-end for 30-60 minutes at 4° C. Purified T cells are removed from beads using a Dynal magnet. Typical yield is about 50% T cells, 87-95% $CD3^+$ by flow cytometry.

Tissue culture 96-well flat-bottom plates are coated with anti-CD3 antibody OKT3 at 5 µg/ml in PBS, 100 µl per well, incubated at 37° C. for 3-6 hours, then washed four times with complete medium 100 µl/well just before T cells are added. Compounds are diluted to 20 times of final in a round bottom tissue culture 96-well plate. Final concentrations are about 10 µM to about 0.00064 µM. A 10 mM stock of compounds provided herein is diluted 1:50 in complete for the first 20× dilution of 200 µM in 2% DMSO and serially diluted 1:5 into 2% DMSO. Compound is added at 10 µl per 200 µl culture, to give a final DMSO concentration of 0.1%. Cultures are incubated at 37° C., 5% $CO_2$ for 2-3 days, and supernatants analyzed for IL-2 and MIP-3α by ELISA (R&D Systems). IL-2 and MIP-3a levels are normalized to the amount produced in the presence of an amount of a compound provided herein, and $EC_{50}$s calculated using non-linear regression, sigmoidal dose-response, constraining the top to 100% and bottom to 0%, allowing variable slope (GraphPad Prism v3.02).

Cell Proliferation Assay

Cell lines (e.g., Namalwa, MUTZ-5, UT-7, and various NHL cell lines) are obtained from the Deutsche Sammlung von Mikroorganismen und Zellkulturen GmbH (Braunschweig, Germany). The cell line KG-1 is obtained from the American Type Culture Collection (Manassas, Va., USA). Cell proliferation as indicated by $^3$H-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 µM in a final concentration of about 0.25% DMSO in triplicate at 37° C. in a humidified incubator at 5% $CO_2$ for 72 hours. One microcurie of $^3$H-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 µl/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope. (GraphPad Prism v3.02).

Immunoprecipitation and Immunoblot

Cells (e.g., various NHL cell lines) are treated with DMSO or an amount of a compound provided herein for 1 hour, then stimulated with 10 U/ml of Epo (R&D Systems) for 30 minutes. Cell lysates are prepared and either immunoprecipitated with Epo receptor Ab or separated immediately by SDS-PAGE. Immunoblots are probed with Akt, phospo-Akt (Ser473 or Thr308), phospho-Gab1 (Y627), Gab1, IRS2, actin and IRF-1 Abs and analyzed on a Storm 860 Imager using ImageQuant software (Molecular Dynamics).

Cell Cycle Analysis

Cells are treated with DMSO or an amount of a compound provided herein overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

Apoptosis Analysis

Cells are treated with DMSO or an amount of a compound provided herein at various time points, then washed with annexin-V wash buffer (BD Biosciences). Cells are incubated with annexin-V binding protein and propidium iodide (BD Biosciences) for 10 minutes. Samples are analyzed using flow cytometry.

Luciferase Assay

Namalwa cells are transfected with 4 µg of AP1-luciferase (Stratagene) per $1\times10^6$ cells and 3 µl Lipofectamine 2000 (Invitrogen) reagent according to manufacturer's instructions. Six hours post-transfection, cells are treated with DMSO or an amount of a compound provided herein. Luciferase activity is assayed using luciferase lysis buffer and substrate (Promega) and measured using a luminometer (Turner Designs).

Example 15

The effect of Compound I-S on the expression of transcription factors controlling plasma cell differentiation and immunoglobulin production using an in-vitro human B-cell differentiation culture system was invesitaged according to the procedures below:

Purification of Human Peripheral Blood Mononuclear Cells

Twenty-five milliliters human buffy coat were placed into each of two 50-mL conical tubes and 25 mL sterile Hank's buffered saline solution (HBSS) were added to each conical tube. The tubes were gently mixed by inverting. Fifteen milliliters of room temperature Ficoll-Paque Plus (GE Healthcare; Cat#17-1440-02) were placed into each of four 50-mL conical tubes. Then 25 mL of the buffy coat/HBSS mixture were layered gently and slowly on top of the Ficoll. The samples were centrifuged at 450 rpm for 35 minutes. The interface containing mononuclear cells was transferred into two 50-mL conical tubes and the volume in each conical tube was adjusted to a total of 50 mL using HBSS. The tubes were centrifuged at 1200 rpm for 10 minutes. The cells were incubated with 5 mL of red blood cell lysis buffer (Boston Bioproducts Cat# IBB-197) for 5 minutes. Cells were washed again in HBSS and spun at 1000 rpm for 10 minutes. The cell pellet was resuspended in 20 mL of B cell medium (Iscove's modified Dulbecco's medium+10% premium fetal bovine serum [PFBS], 1% penicillin/streptomycin [P/S], and 5 µg/mL human insulin), pipetted through a 30 micron filter, and an aliquot was counted using the cell counter.

B Cell Enrichment for CD19+ Cells

Aliquots of purified PBMCs ($2\times10^8$ cells) were placed in tubes, centrifuged at 1200 rpm for 5 minutes, and then supernatants were discarded. Cells in each tube were resuspended in 4 mL of Robosep Buffer (StemCell Technologies Catalog #20104), transferred to a 14-mL polystyrene round bottom tube (BD Catalog #352057), and mixed well. Then 200 µL of EasySep Human B cell enrichment cocktail (StemCell Technologies Catalog #19054) were added to each tube. Samples were vortexed and incubated at room temperature for 10 minutes. Next, 300 µL of EasySep Magnetic particles (vortexed) (StemCell Technologies Catalog #19054) were added to each tube. Samples were vortexed and incubated at room temperature for 5 minutes. After the 5-minute incubation, 5 mL of Robosep buffer were added to each tube and the cell suspension was mixed well by pipetting up and down. Each tube was immediately placed in the silver magnet (StemCell Technologies Catalog #18001) and incubated at room temperature for 5 minutes. After incubation, using one continuous motion, the magnet and tube were inverted and the desired fraction from each tube was poured off into a 50-mL conical tube. The enriched PBMC samples from a single donor were combined. The combined fraction was centrifuged at 1200 rpm for 5 minutes and then supernatants were discarded. The enriched $CD19^+$ cells were resuspended in 5 mL of B cell medium and counted on the cell counter.

B Cell Differentiation Assay

Step 1—B Cell Activation—Day 0 Through Day 4:

Fresh B cell cocktail was prepared by adding 50 µg/mL of human transferrin to B cell medium (Iscove's medium with 10% PFBS, 1% P/S, and 5 µg/mL human insulin). The required volume of medium needed for the experiment was filtered through a 0.22 micron filter. Add B cell differentiation cocktail (final concentration): recombinant human Interleukin (IL)-2 (20 U/mL), IL-10 (50 ng/mL), IL-15 (10 ng/mL), CD40 Ligand/TNFSF5/histidine-tagged (50 ng/mL), polyHistidine mouse IgG1 antibody (5 µg/mL), and ODN 2006-Human TLR9 ligand (10 µg/mL) to cells. Five milliliters ($1\times10^5$/mL) of $CD19^+$ B cells were added to each well of a 6-well flat-bottom plate (final cell count=$5\times10^5$/well). Five microliters of a 1× solution of compound or DMSO was added to each test well (0.1% final concentration of DMSO) and incubated at 37° C. for 4 days.

Step 2—Plasmablast Generation—Day 4 Through Day 7:

Cells were harvested and counted on the cell counter, an aliquot was removed for flow analysis, and the remaining cells were washed with phosphate buffered saline (PBS). Fresh B cell cocktail was prepared by adding 1 µg/ml of human transferrin to B cell medium (Iscove's medium with 10% PFBS, 1% P/S, and 5 µg/mL human insulin). The required volume of medium needed for the experiment was filtered through a 0.22 micron filter. B cell differentiation cocktail (final concentration) consisting of: recombinant human IL-2 (20 U/mL), IL-10 (50 ng/mL), IL-15 (10 ng/mL), and IL-6 (50 ng/mL) was added to cells. Fresh B cell cocktail was added to cells. Cells were transferred back to the original wells and the volume was adjusted to 5 mL. Five microliters of a 1× solution of compound or DMSO was added to each test well (0.1% final DMSO) and incubated at 37° C. for 3 days.

On Day 4 and Day 7 cells were harvested and counted on the cell counter. A portion of the cells were then removed for flow analysis and the remaining cells were lysed with RLT buffer and stored at −80° C. for RNA extraction and gene expression. Supernatants were divided into aliquots and frozen at −20° C. for immunoglobulin assays.

Preparation of Test Compound Stock Solutions and Dilutions

All test articles were weighed and dissolved in sterile 100% dimethyl sulfoxide (DMSO) (Research Organics, Cleveland, Ohio) to create 40 mM stock solutions. Dilutions of the 40 mM stock solution were used in the assay to obtain final test compound concentrations based on experimental design.

Ribonucleic Acid Extraction and Gene Expression

Differentiated B cells (see B Cell Differentiation Assay above) were harvested for total ribonucleic acid (RNA) preparation with a Qiacube RNA extraction instrument (Qiagen, Valencia, Calif.) using QIAGEN RNeasy mini spin-column kits (Catalog #74104). Purified RNA was reverse transcribed into cDNA with thermal cycler (MJ Research, Inc., St. Bruno, Quebec, Canada) using a reverse-transcriptase kit (Applied Biosystems). The gene expression assay was carried out using 7500 real time polymerase chain reaction (RT-PCR) system (Applied Biosystems) in triplicate. A glyceraldehyde 3-phosphate dehydrogenase gene expression assay control was run for each sample and used as a normalization control. For each gene, values for samples within each experiment were normalized to the corresponding 0.1% DMSO treatment value for that particular time point.

Immunoglobulin Assay

Supernatants (see B Cell Differentiation Assay above) were harvested and analyzed by ELISA for IgG and IgM production (ZeptoMetrix Corp, Buffalo, N.Y.).

Cell Phenotyping

Differentiated B cells (see B Cell Differentiation Assay above) were harvested, counted, and divided into aliquots of about $1\times10^6$ cells or less per 4-mL tube. The cells were washed once with stain buffer. Next, the cells then were blocked with 10% human serum/PBS for 20 minutes at 2 to 8° C. Following blocking, the cells were centrifuged for 5 minutes at 1200 rpm and supernatants discarded. In the 100 µL of remaining buffer, 20 µL of various BD Pharmigen flow antibodies were added according to experimental design. The cells were stained for 20 to 30 minutes at room temperature. Then the cells were washed twice with stain buffer and supernatants discarded. Next, 500 µL of stain buffer or PBS were added to the tubes. The samples were immediately analyzed or stored at 4° C. overnight. Cells were stained with mouse anti-human CD20 and CD38, CD19 and CD27, or respective isotype control antibodies. All samples were analyzed using a fluorescence activated cell sorting FACSCanto flow cytometer, FACSDiva analysis software (BD Bioscience), and FlowJo Analysis software.

Cell Viability Analysis

To determine live cell count, B cells (see B Cell Differentiation Assay above) were stained with 0.4% Trypan blue (Gibco cat #15250) and live cells counted using the Countess automated cell counter (Invitrogen) in duplicate samples.

Results

Figure 2:
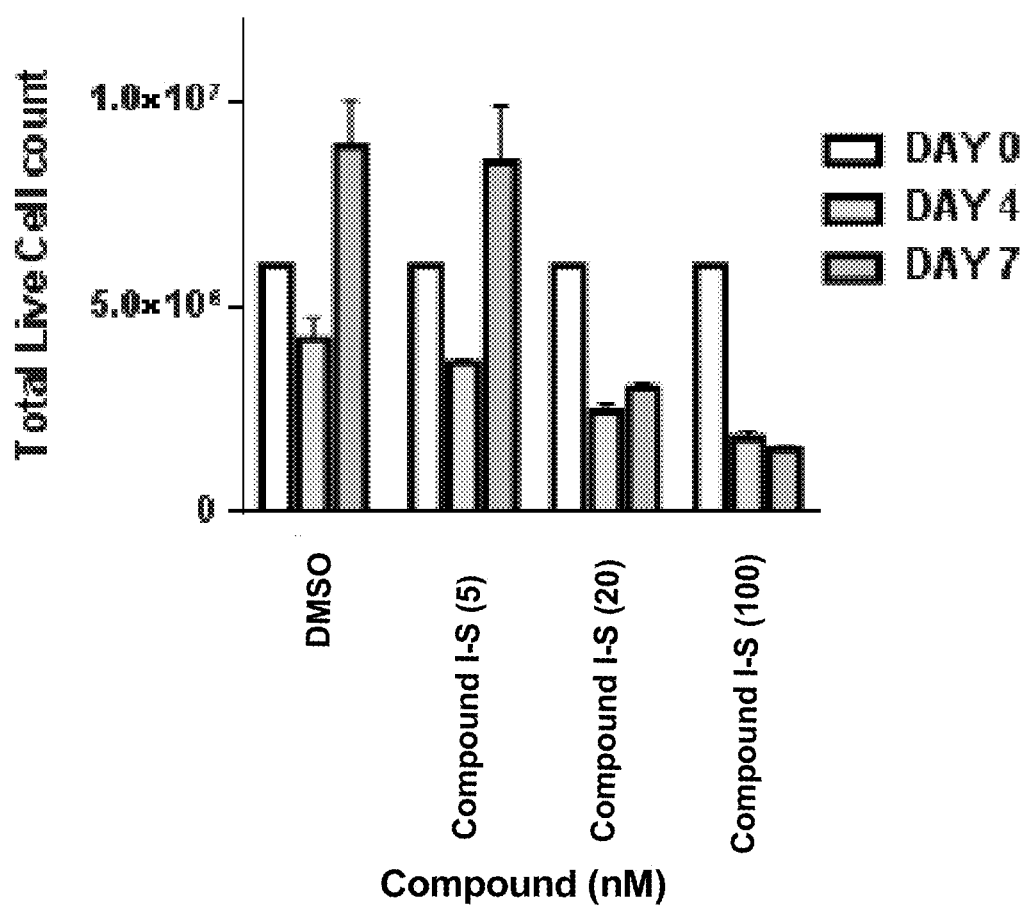
FIG. 2 shows effect of Compound I-S on live cell count for each class of B cell from Day 0 to Day 7.
Figure 3:
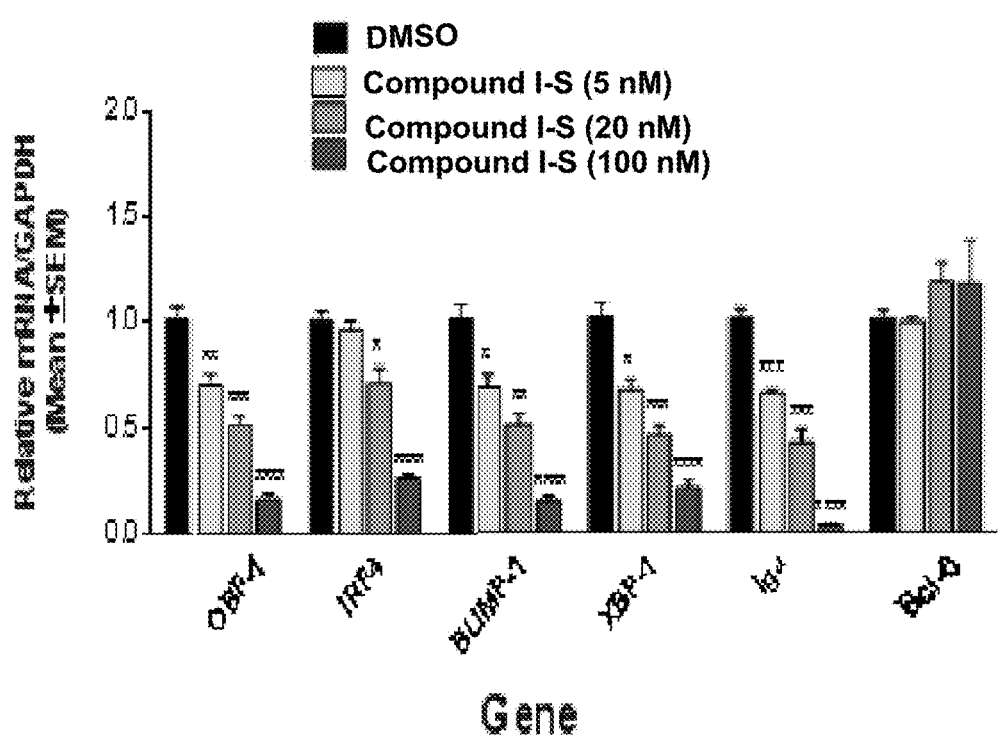
FIG. 3 shows effect of Compound I-S on B and plasma cell transcription factor expression.
Figure 4:
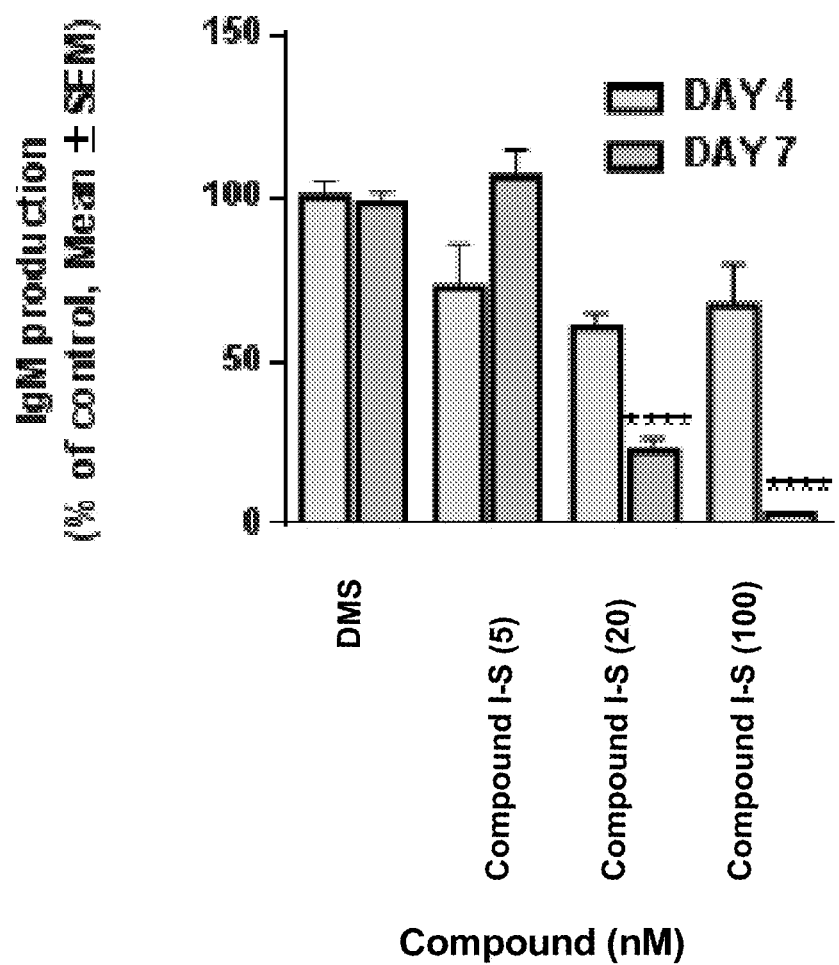
FIG. 4 shows effect of Compound I-S on immunoglobulin M production in plasmablast cultures.
Figure 5:
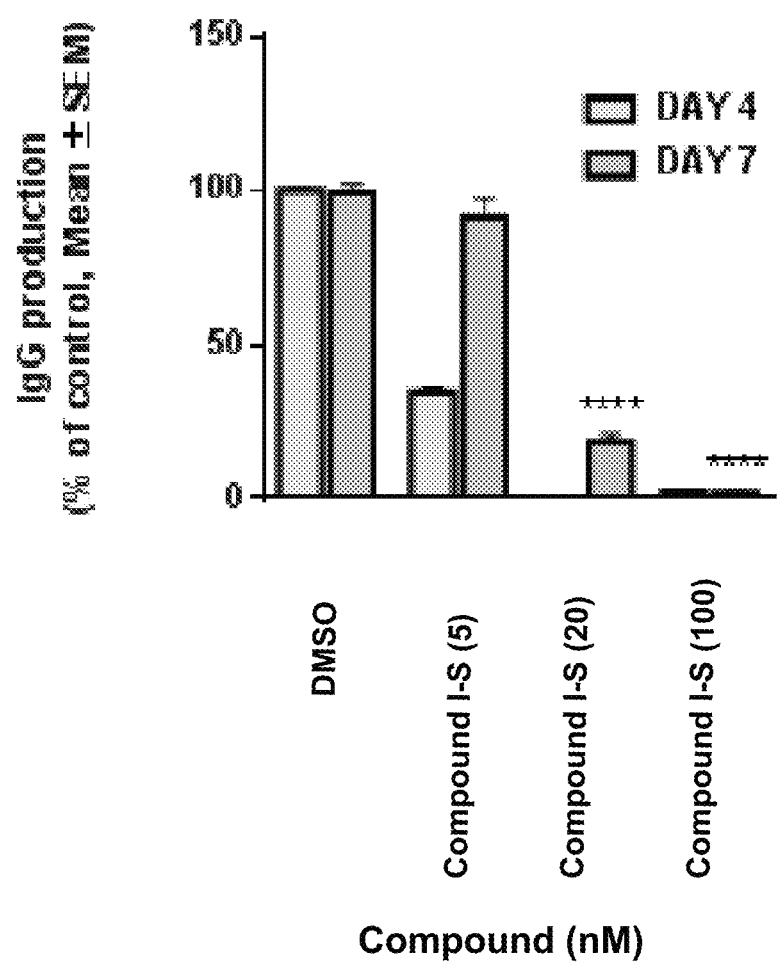
FIG. 5 shows effect of Compound I-S on immunoglobulin G production in plasmablast cultures.

In the in vitro model of primary human B cell differentiation toward the plasma cell lineage, Compound I-S dose-dependently reduced the percentage of $CD20^-CD38^+$ plasmablasts (PB) and increased the percentage of CD20+ CD38− activated B cells (ABC) (FIG. 1). Cell counts (FIG. 2) were performed on Day 4 and Day 7, and Compound I-S was found to reduce B cell viability during the 7 day culture. Gene expression analysis was performed on Day 7 with the differentiated B cells (FIG. 3). Compound I-S dose-dependently and significantly inhibited expression of plasma cell lineage transcription factors IgJ, IRF-4, BLIMP-1, OBF-1, and XBP-1. Compound I-S did not decrease the expression of the germinal center lineage B cell transcription factors BCL-6. Compound I-S significantly inhibited IgM and IgG production during plasmablast differentiation (FIG. 4 and FIG. 5).

BCL6=B-cell CLL/lymphoma 6 germinal center lineage transcription factor; BLIMP-1=B-lymphocyte-induced maturation protein 1 plama cell lineage transcription factor; IgJ=immunoglobulin J-chain gene; IRF-4=interferon regulatory factor 4 plasma cell lineage transcription factor; OBF-1 (POU2AF1)=POU Class 2 Associating Factor 1; XBP-1=X-box binding protein 1 plasma cell lineage transcription factor.

These findings indicate that Compound I-S has the potential to inhibit B cell differentiation to the plasma cell lineage, and suggests that Compound I-S may be useful in the treatment of autoimmune disorders such as SLE, which are characterized by the overproduction of autoantibodies.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

All of the patents, patent applications and publications referred to herein are incorporated herein in their entireties. Citation or identification of any reference in this application is not an admission that such reference is available as prior art to the claimed subject matter.

What is claimed is:

1. A compound of Formula (I):

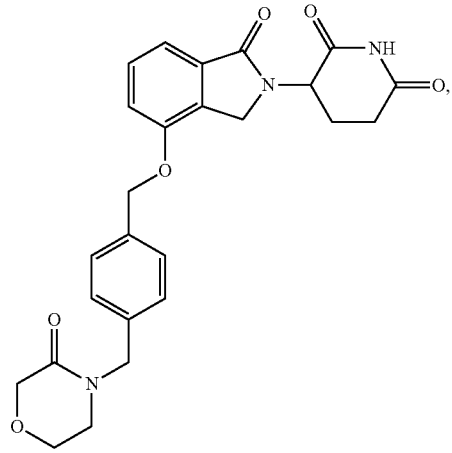

(I)

or an isotopologue thereof, or an enantiomer or a mixture of enantiomers thereof, or a pharmaceutically acceptable salt, solvate, clathrate, polymorph, or co-crystal thereof.

2. The compound of claim 1, which is a compound of Formula (I-S):

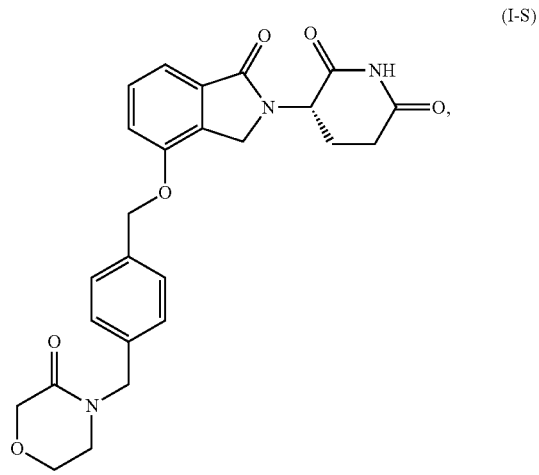 [SMILES: O=C1CC[C@H](N2Cc3c(OCc4ccc(CN5CCOCC5=O)cc4)cccc3C2=O)C(=O)N1]

(I-S)

or an isotopologue thereof, or a pharmaceutically acceptable salt, solvate, clathrate, polymorph, or co-crystal thereof.

3. The compound of claim 2, which is a compound of Formula (I-S):

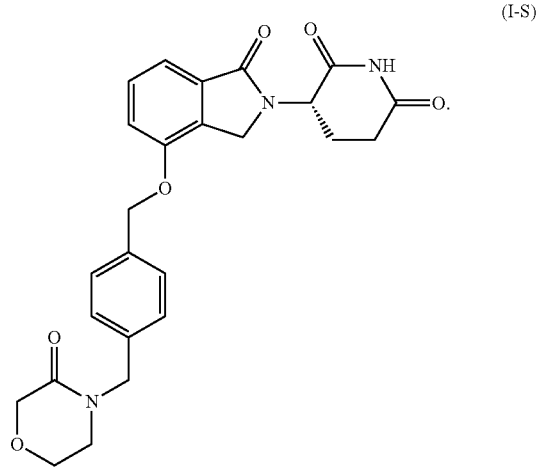 [SMILES: O=C1CC[C@H](N2Cc3c(OCc4ccc(CN5CCOCC5=O)cc4)cccc3C2=O)C(=O)N1]

(I-S)

4. The compound of claim 1, which is substantially pure.

5. The compound of claim 1, which is a compound of Formula (II):

(II)

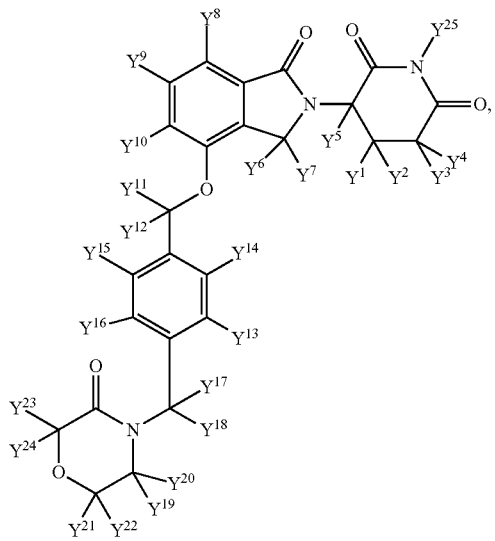

or an enantiomer or a mixture of enantiomers thereof, or a pharmaceutically acceptable salt, solvate, clathrate, polymorph, or co-crystal thereof, wherein one or more of $Y^1, Y^2, Y^3, Y^4, Y^5, Y^6, Y^7, Y^8, Y^9, Y^{10}, Y^{11}, Y^{12}, Y^{13}, Y^{14}, Y^{15}, Y^{16}, Y^{17}, Y^{18}, Y^{19}, Y^{20}, Y^{21}, Y^{22}, Y^{23}, Y^{24}$, and $Y^{25}$ is deuterium, and any remaining Y atoms are non-enriched hydrogen atoms.

6. The compound of claim 5, which is a compound of Formula (II-S):

(II-S)

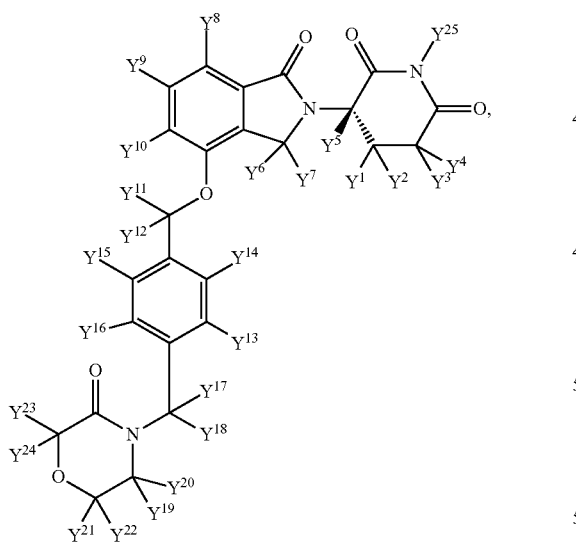

or a pharmaceutically acceptable salt, solvate, clathrate, polymorph, or co-crystal thereof.

7. The compound of claim 5, wherein one of $Y^1, Y^2, Y^3, Y^4, Y^5, Y^6, Y^7, Y^8, Y^9, Y^{10}, Y^{11}, Y^{12}, Y^{13}, Y^{14}, Y^{15}, Y^{16}, Y^{17}, Y^{18}, Y^{19}, Y^{20}, Y^{21}, Y^{22}, Y^{23}, Y^{24}$, and $Y^{25}$ is a deuterium, and the others of $Y^1, Y^2, Y^3, Y^4, Y^5, Y^6, Y^7, Y^8, Y^9, Y^{10}, Y^{11}, Y^{12}, Y^{13}, Y^{14}, Y^{15}, Y^{16}, Y^{17}, Y^{18}, Y^{19}, Y^{20}, Y^{21}, Y^{22}, Y^{23}, Y^{24}$, and $Y^{25}$ are non-enriched hydrogen atoms.

8. The compound of claim 5, wherein two, three, four, five, six, seven, eight, nine, ten, eleven, twelve, thirteen, fourteen, fifteen, sixteen, seventeen, eighteen, nineteen, twenty, twenty one, twenty two, twenty three, or twenty four of $Y^1, Y^2, Y^3, Y^4, Y^5, Y^6, Y^8, Y^9, Y^{10}, Y^{11}, Y^{12}, Y^{13}, Y^{14}, Y^{15}, Y^{16}, Y^{17}, Y^{18}, Y^{19}, Y^{20}, Y^{21}, Y^{22}, Y^{23}, Y^{24}$, and $Y^{25}$ are deuterium, and the others of $Y^1, Y^2, Y^3, Y^4, Y^5, Y^6, Y^7, Y^8, Y^9, Y^{10}, Y^{11}, Y^{12}, Y^{13}, Y^{14}, Y^{15}, Y^{16}, Y^{17}, Y^{18}, Y^{19}, Y^{20}, Y^{21}, Y^{22}, Y^{23}, Y^{24}$, and $Y^{25}$ are non-enriched hydrogen atoms.

9. The compound of claim 5, wherein $Y^{25}$ is a non-enriched hydrogen.

10. The compound of claim 5, wherein $Y^5$ is a deuterium.

11. The compound of claim 5, wherein all of $Y^1, Y^2, Y^3, Y^4, Y^5, Y^6, Y^7, Y^8, Y^9, Y^{10}, Y^{11}, Y^{12}, Y^{13}, Y^{14}, Y^{15}, Y^{16}, Y^{17}, Y^{18}, Y^{19}, Y^{20}, Y^{21}, Y^{22}, Y^{23}, Y^{24}$, and $Y^{25}$ are deuterium.

12. The compound of claim 5, which is a compound of Formula (III):

(III)

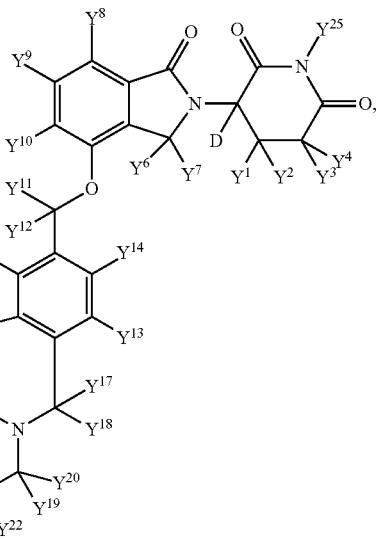

or an enantiomer or a mixture of enantiomers thereof, or a pharmaceutically acceptable salt, solvate, clathrate, polymorph, or co-crystal thereof, wherein one or more of $Y^1, Y^2, Y^3, Y^4, Y^6, Y^7, Y^8, Y^9, Y^{10}, Y^{11}, Y^{12}, Y^{13}, Y^{14}, Y^{15}, Y^{16}, Y^{17}, Y^{18}, Y^{19}, Y^{20}, Y^{21}, Y^{22}, Y^{23}, Y^{24}$ and $Y^{25}$ is deuterium, and any remaining Y atoms are non-enriched hydrogen atoms.

13. The compound of claim 12, which is a compound of Formula (III-S):

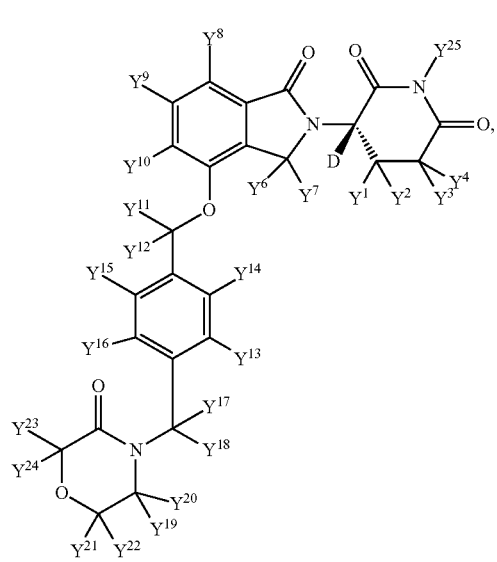

(III-S)

or a pharmaceutically acceptable salt, solvate, clathrate, polymorph, or co-crystal thereof.

14. The compound of claim 5, which is a compound of Formula (IV):

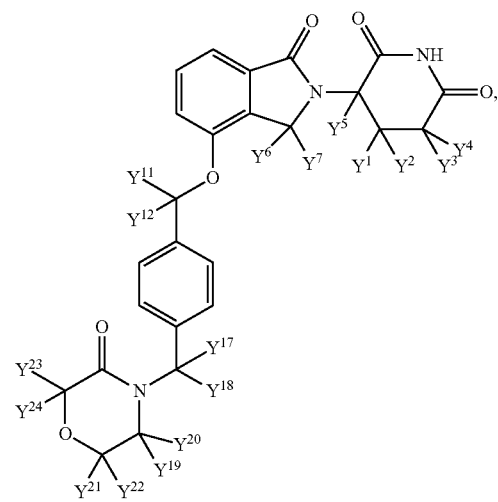

(IV)

or an enantiomer or a mixture of enantiomers thereof, or a pharmaceutically acceptable salt, solvate, clathrate, polymorph, or co-crystal thereof, wherein one or more of $Y^1$, $Y^2$, $Y^3$, $Y^4$, $Y^5$, $Y^6$, $Y^7$, $Y^{11}$, $Y^{12}$, $Y^{17}$, $Y^{18}$, $Y^{19}$, $Y^{20}$, $Y^{21}$, $Y^{22}$, $Y^{23}$, and $Y^{24}$ is deuterium, and any remaining Y atoms are non-enriched hydrogen atoms.

15. The compound of claim 14, which is a compound of Formula (IV-S):

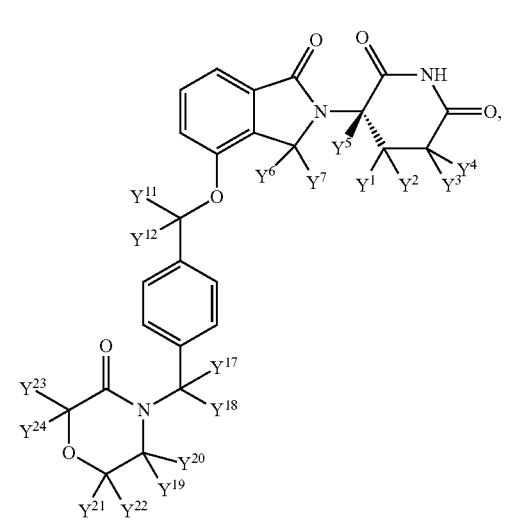

(IV-S)

or a pharmaceutically acceptable salt, solvate, clathrate, polymorph, or co-crystal thereof.

16. The compound of claim 5, which is:

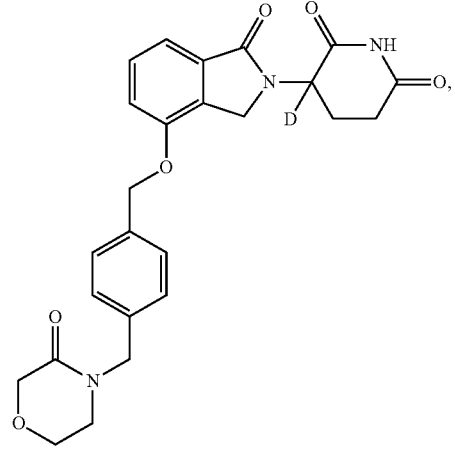 [SMILES: [2H]C1(N2Cc3c(OCc4ccc(CN5CCOCC5=O)cc4)cccc3C2=O)CCC(=O)NC1=O]

or an enantiomer or a mixture of enantiomers thereof, or a pharmaceutically acceptable salt, solvate, clathrate, polymorph, or co-crystal thereof.

17. The compound of claim 16, which is:
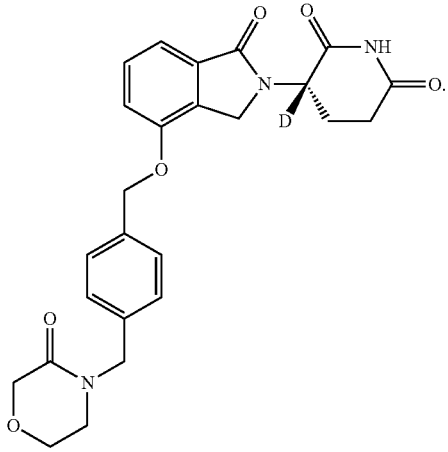 [SMILES: [2H][C@]1(N2Cc3c(OCc4ccc(CN5CCOCC5=O)cc4)cccc3C2=O)CCC(=O)NC1=O]
18. A compound, which is:
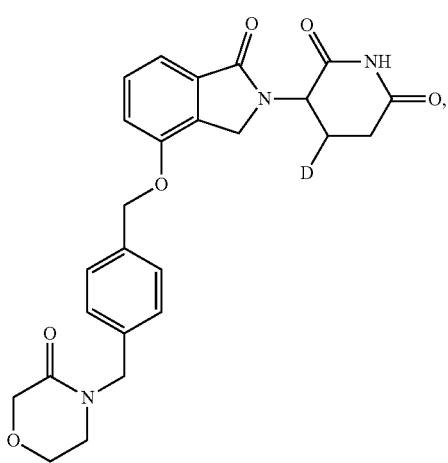
-continued
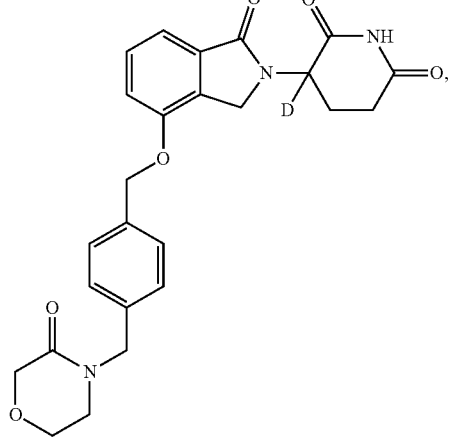
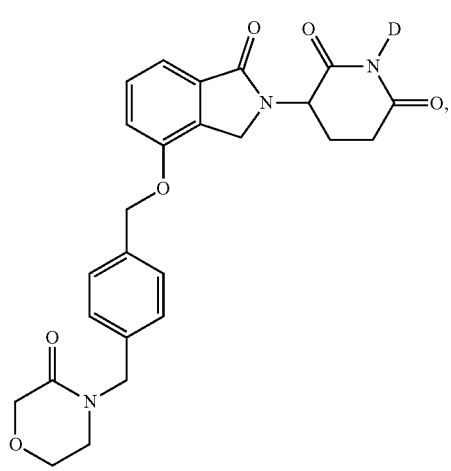
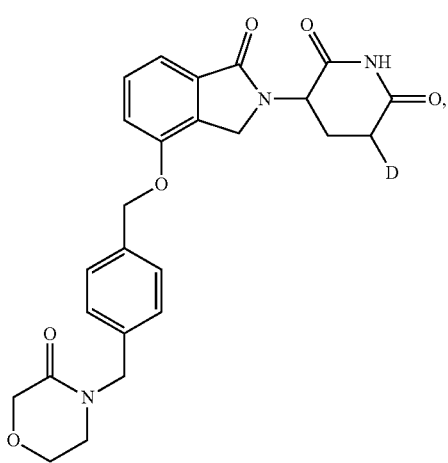
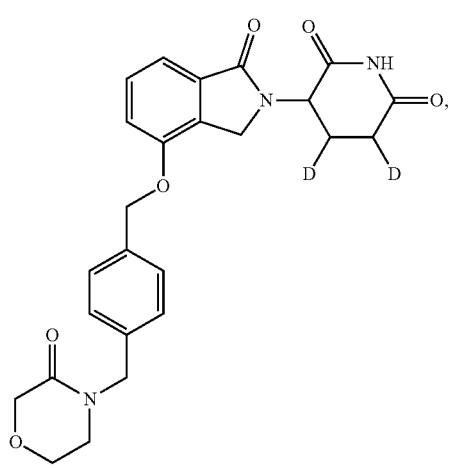

133
-continued
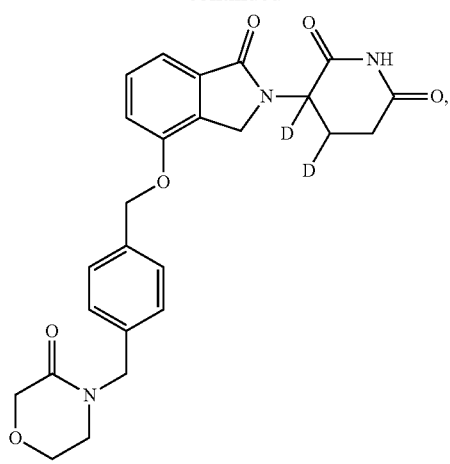
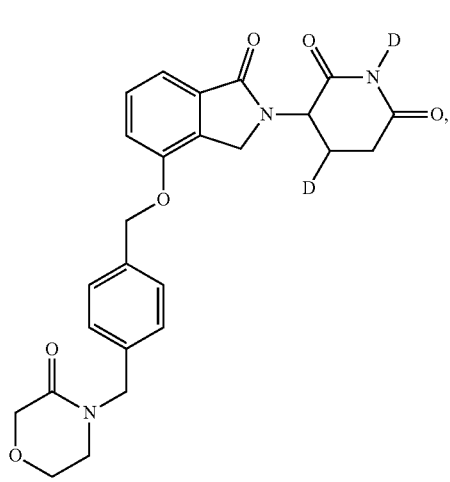
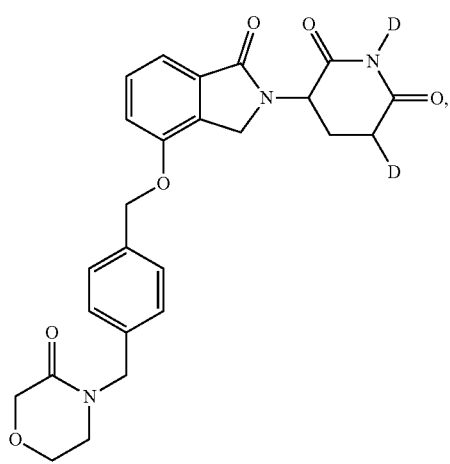
134
-continued
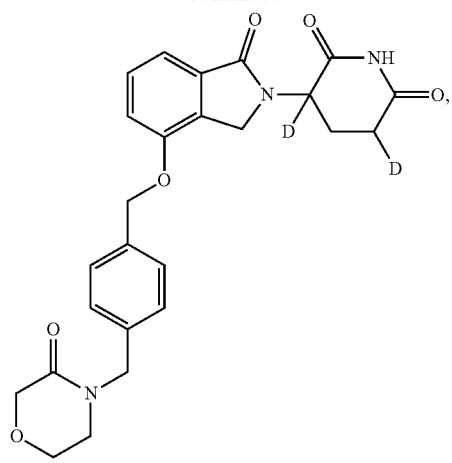
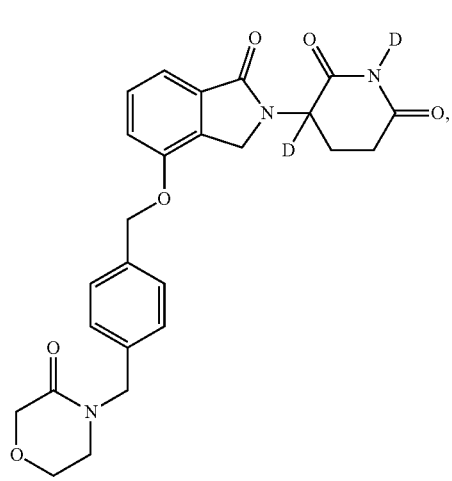
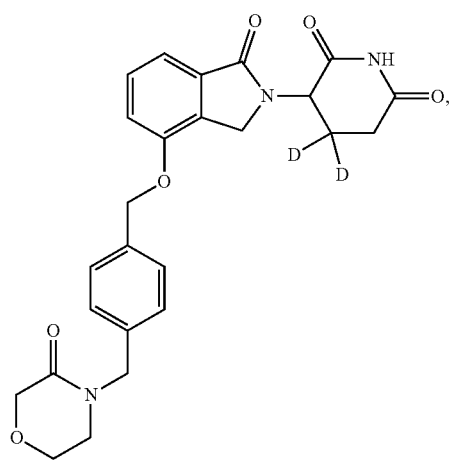

135
-continued
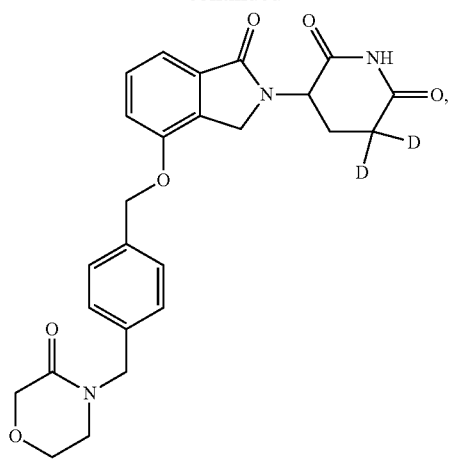
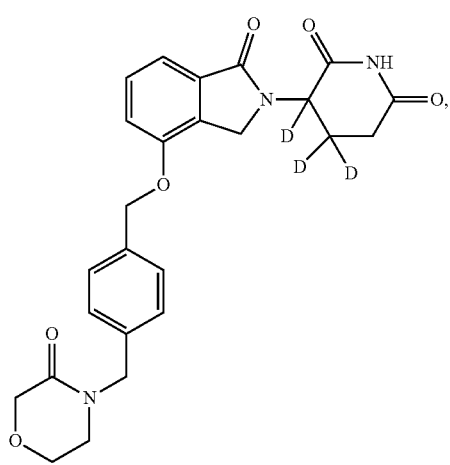
136
-continued
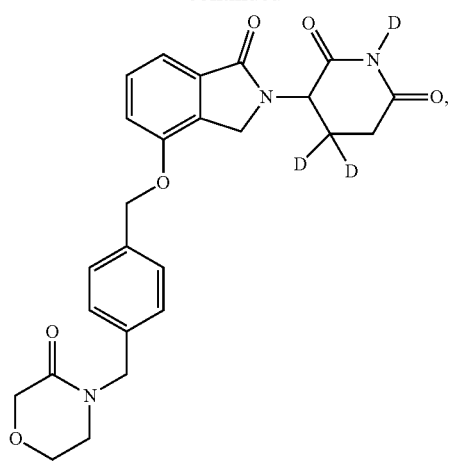

137
-continued
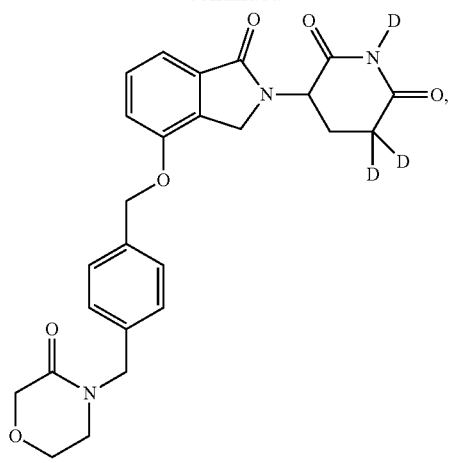
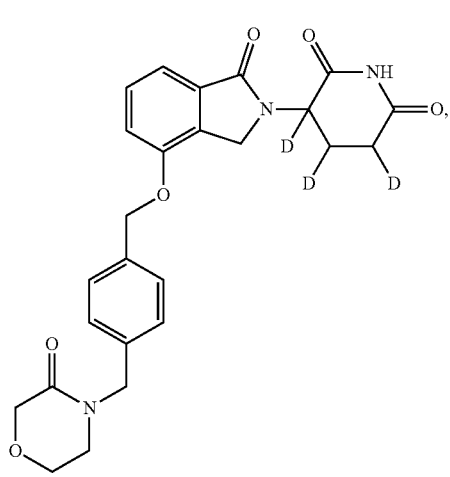
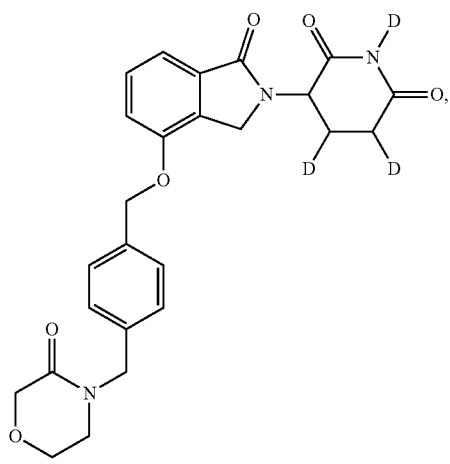
138
-continued
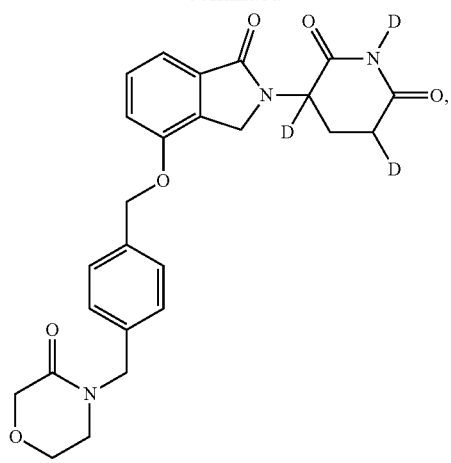
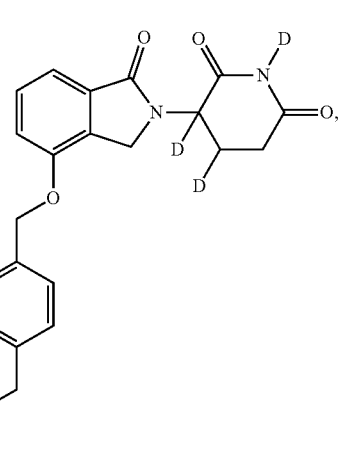
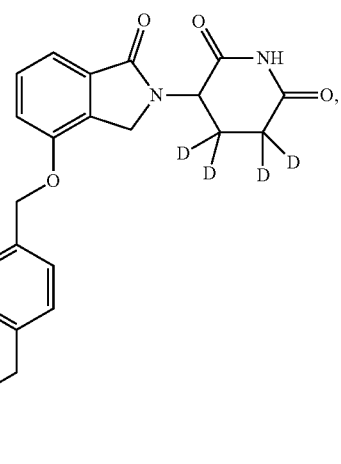

139
-continued
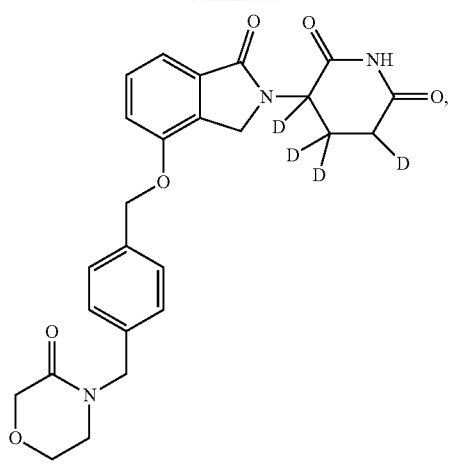
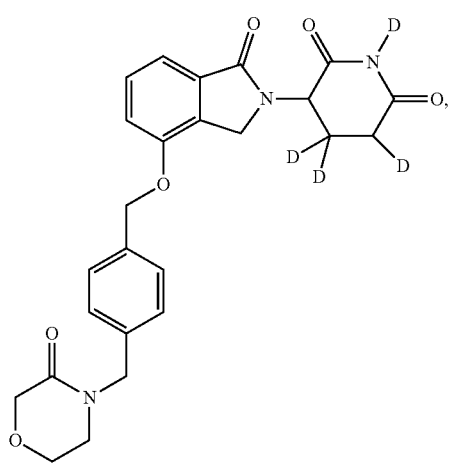
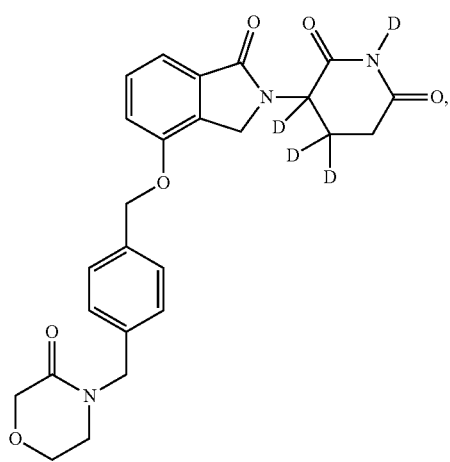
140
-continued
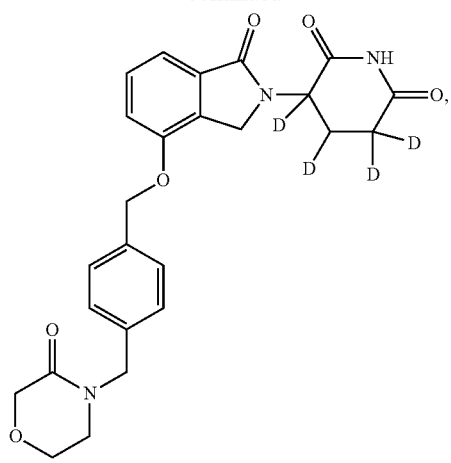
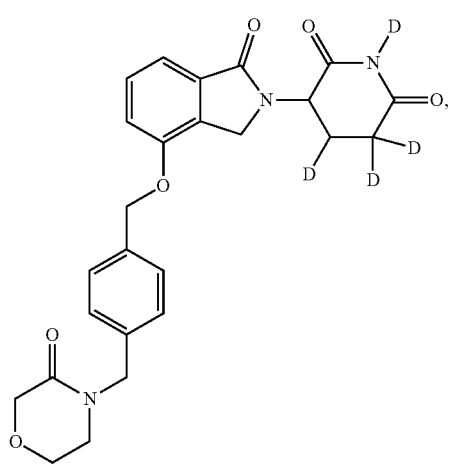
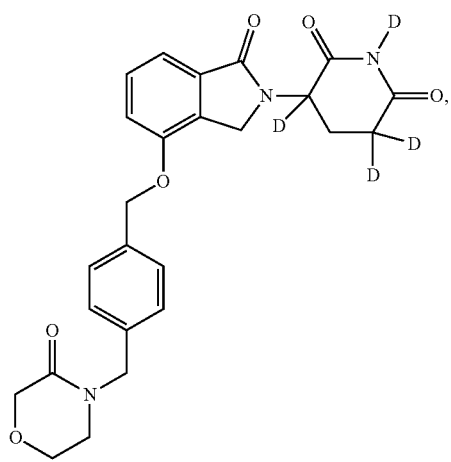

141
-continued
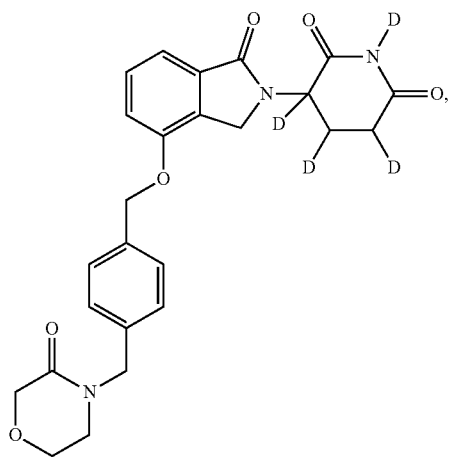
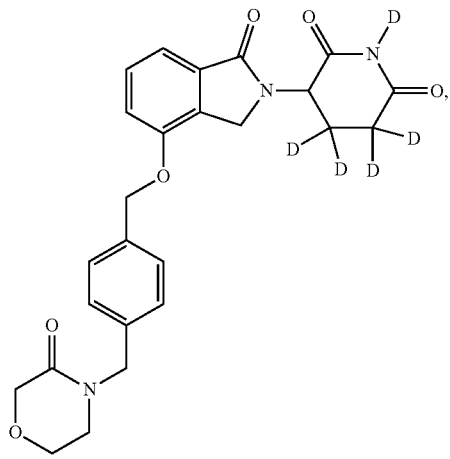
142
-continued
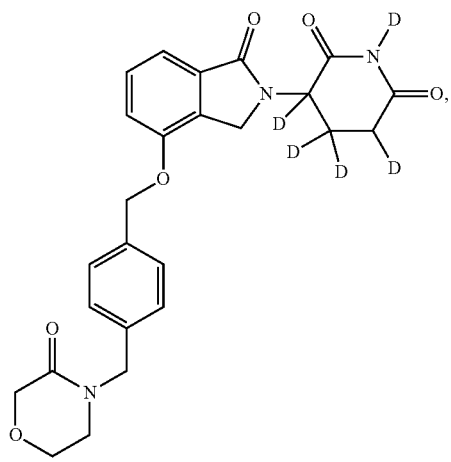

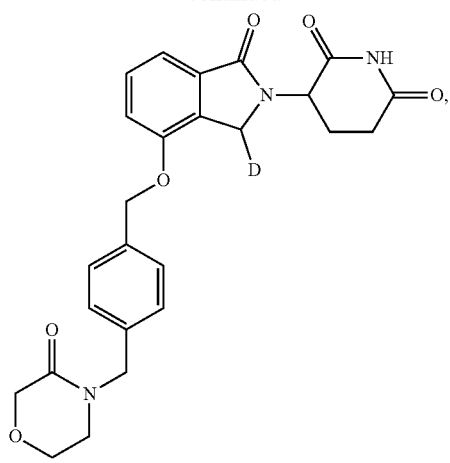
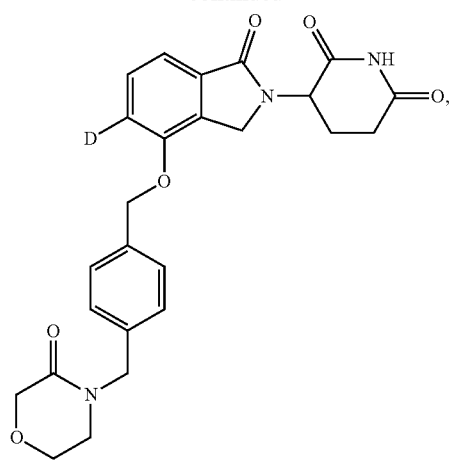
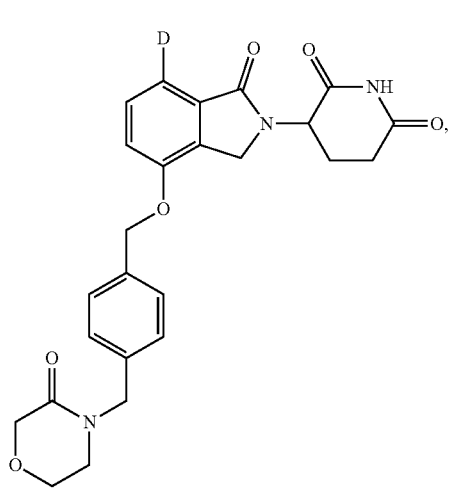
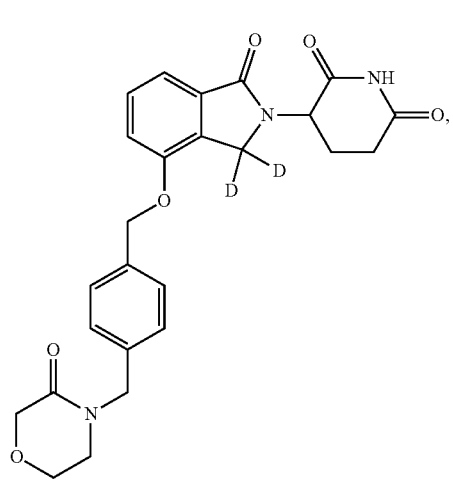
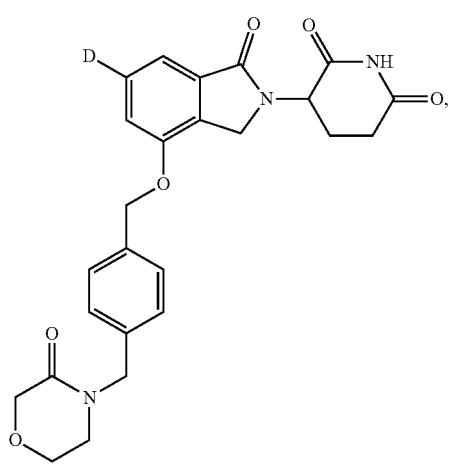
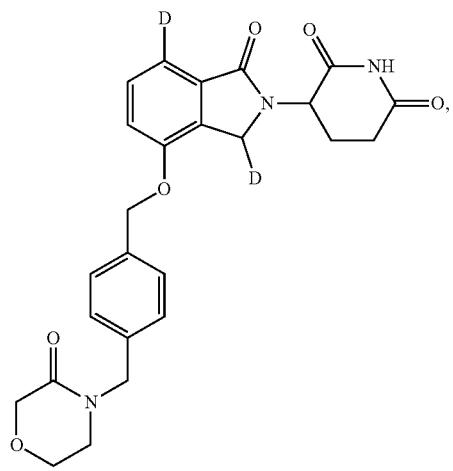

145
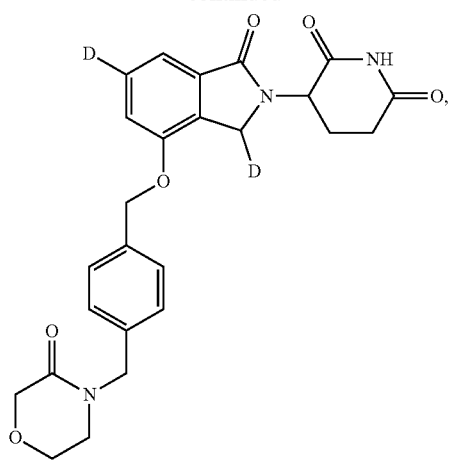
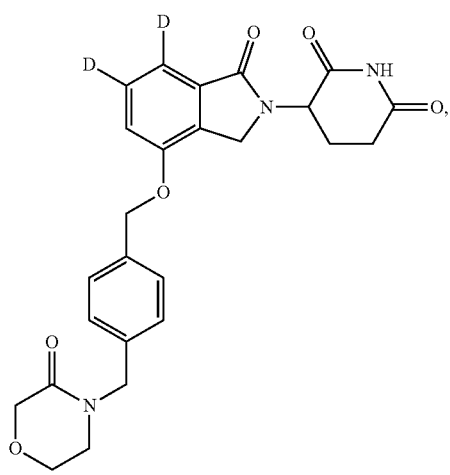
146
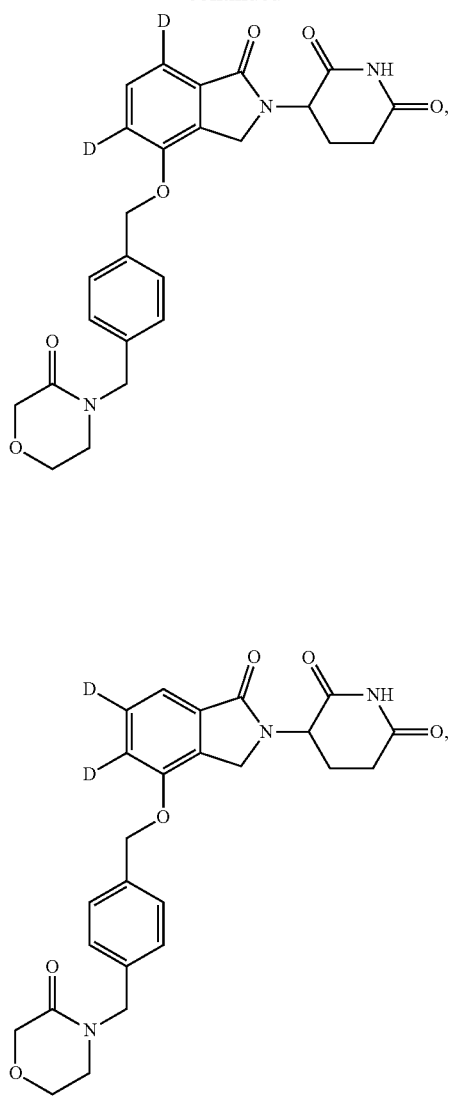
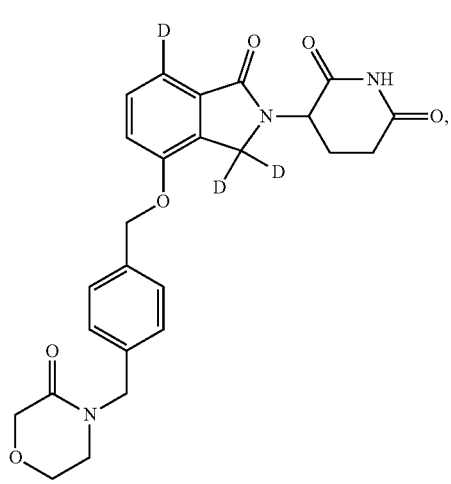

147
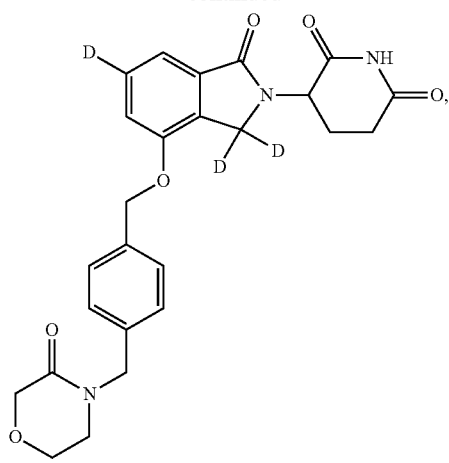
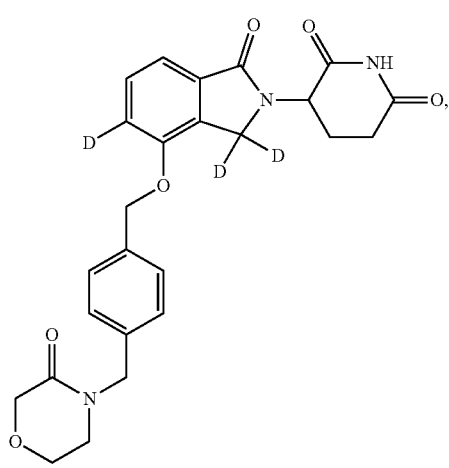
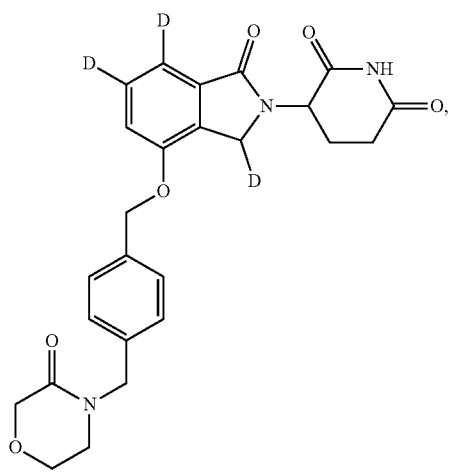
148
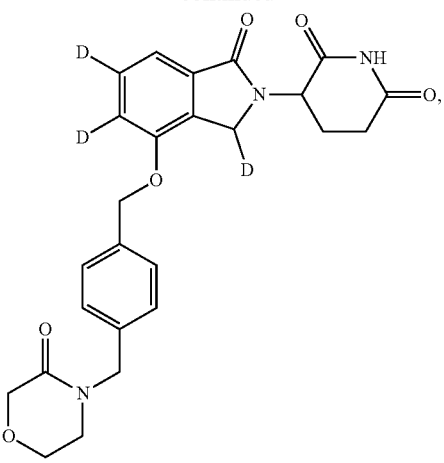
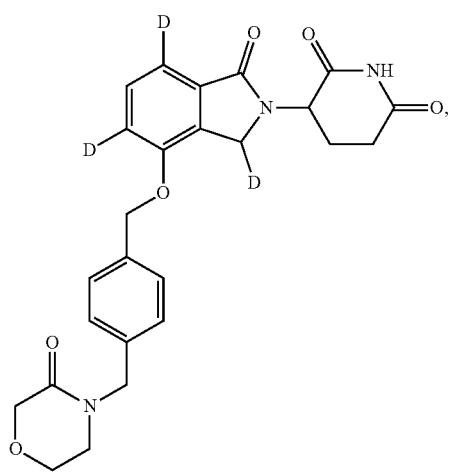
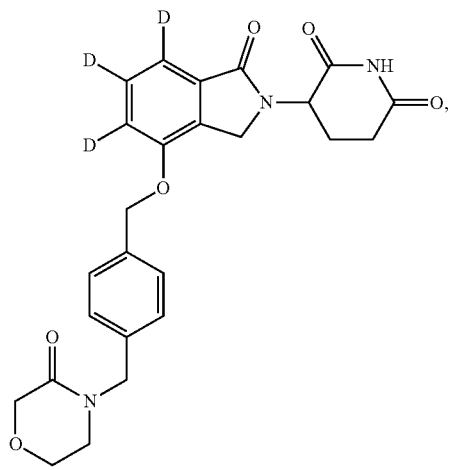

149
-continued
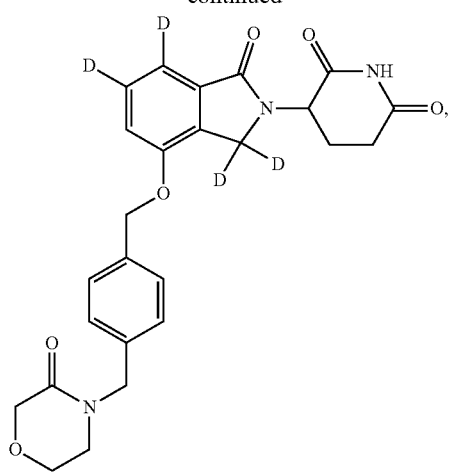
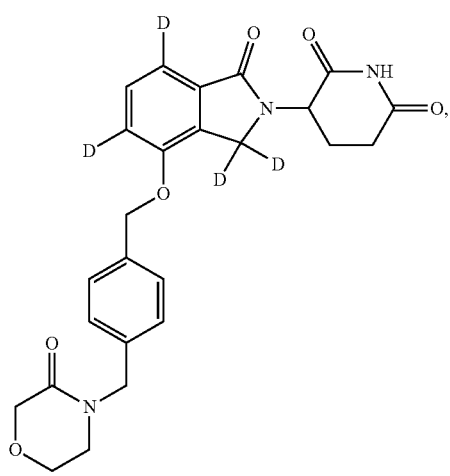
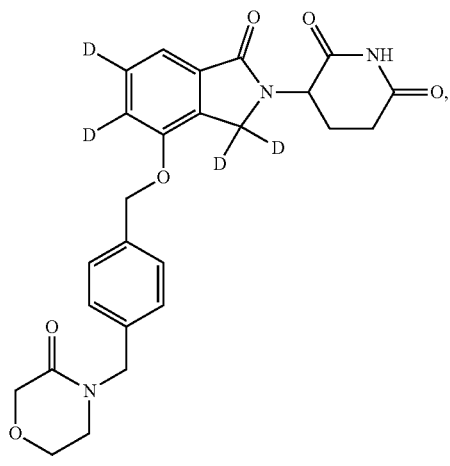
150
-continued
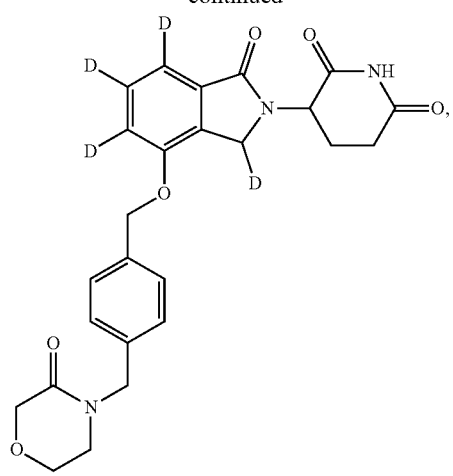
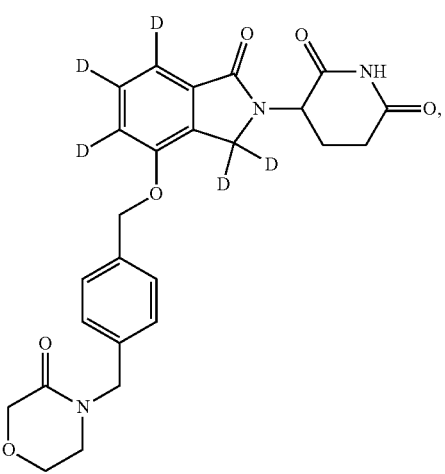
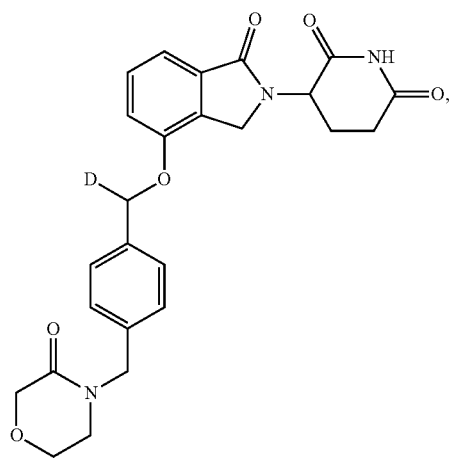

151
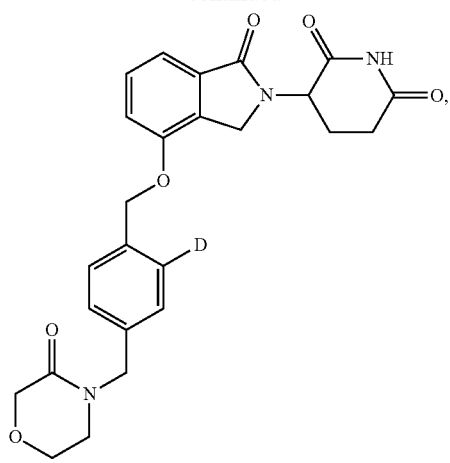
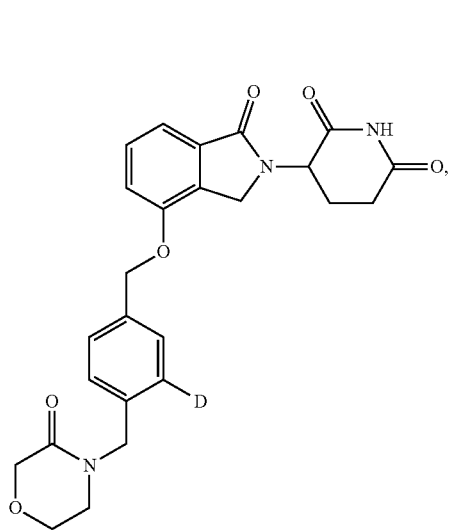
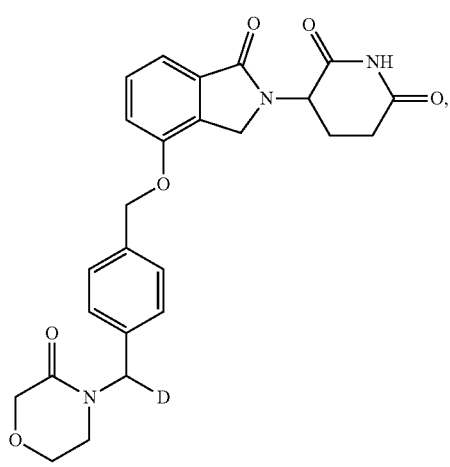
152
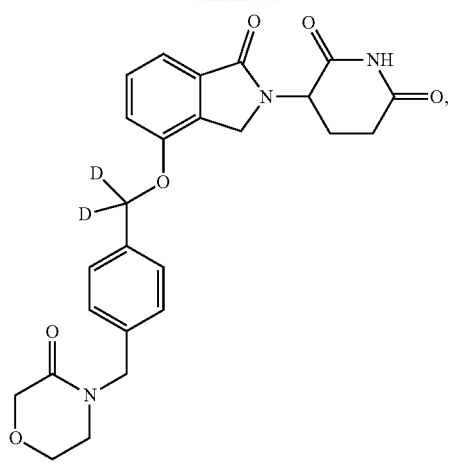
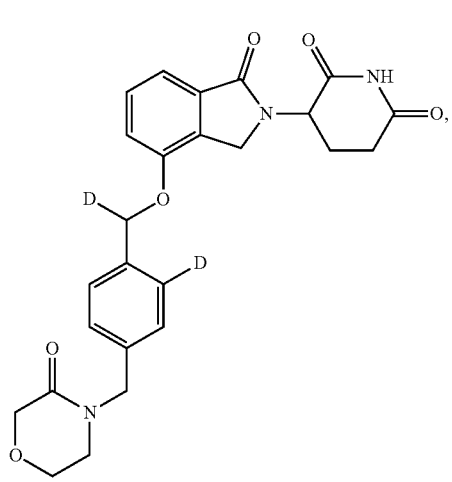
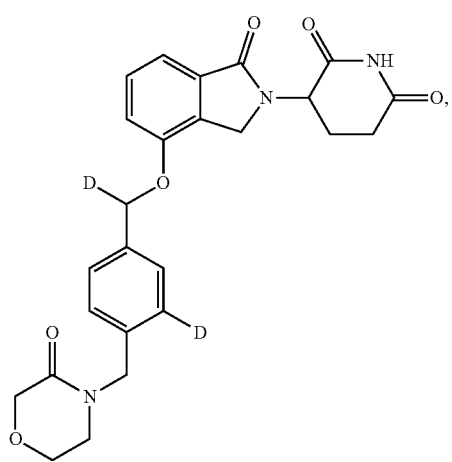

153
-continued
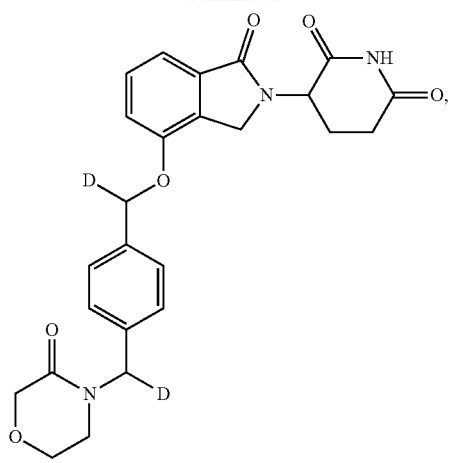
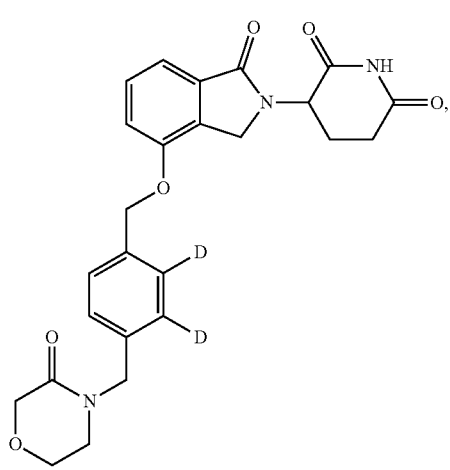
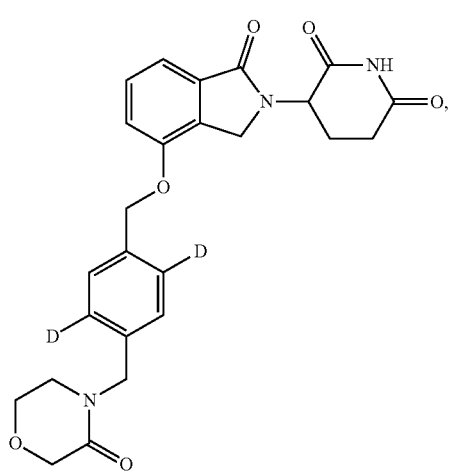
154
-continued
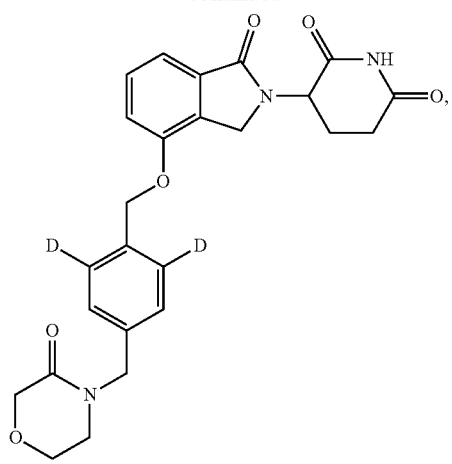
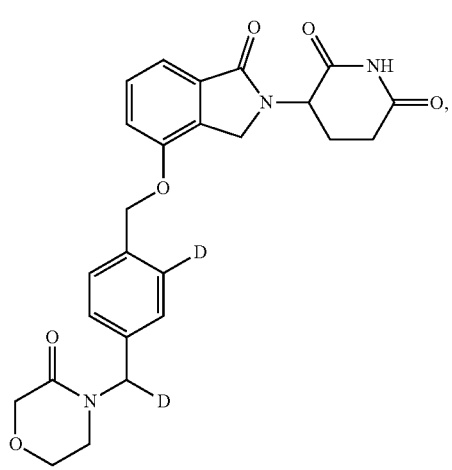
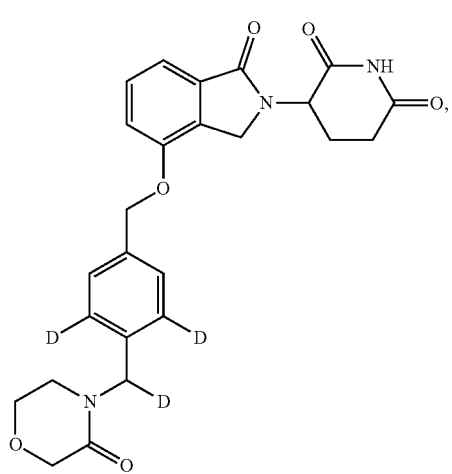

155
-continued
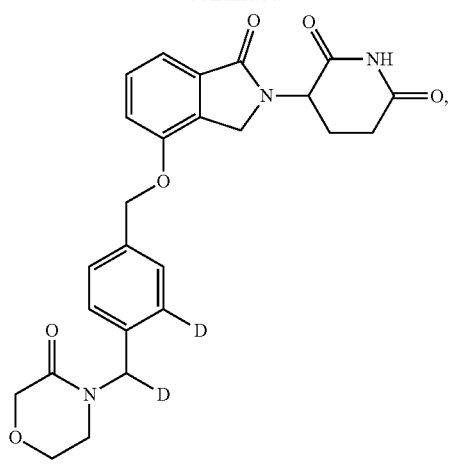
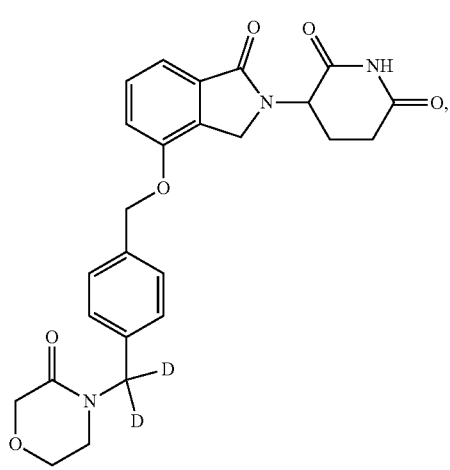
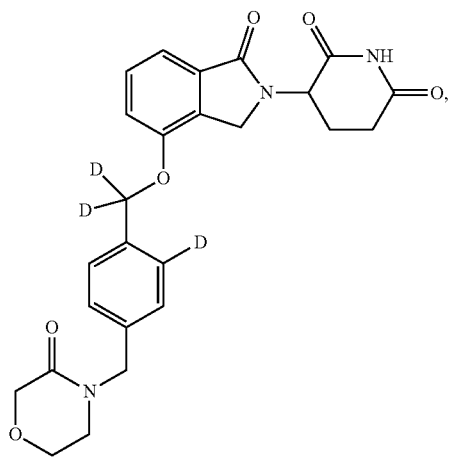
156
-continued
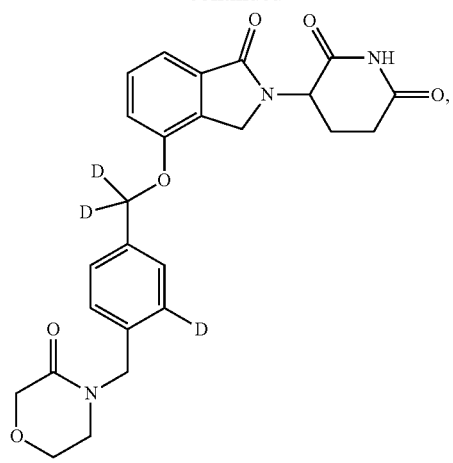
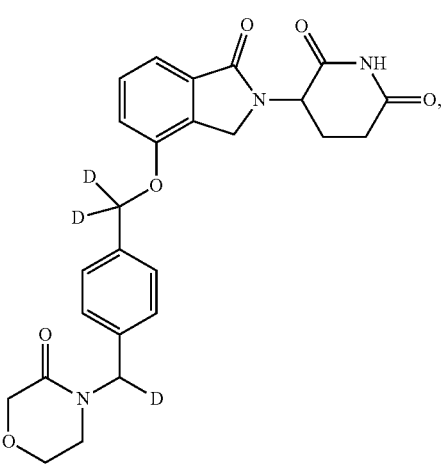
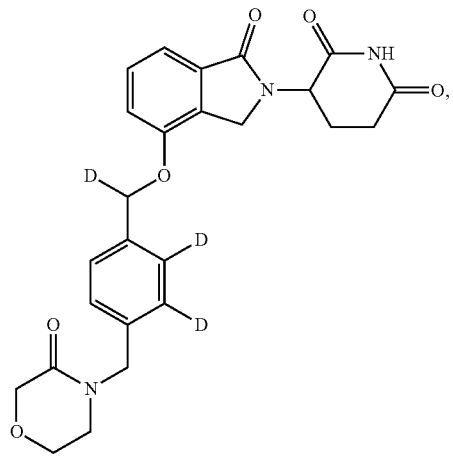

157 -continued
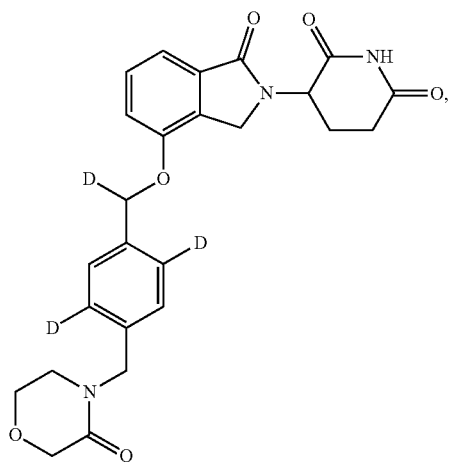
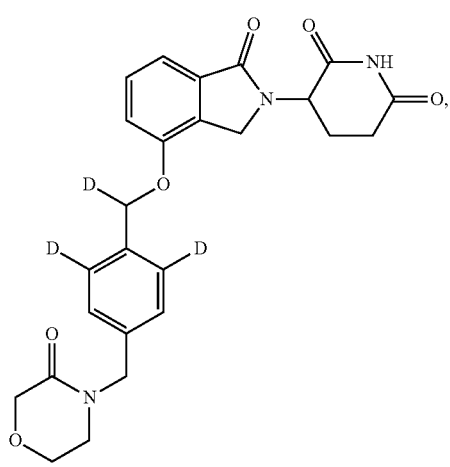
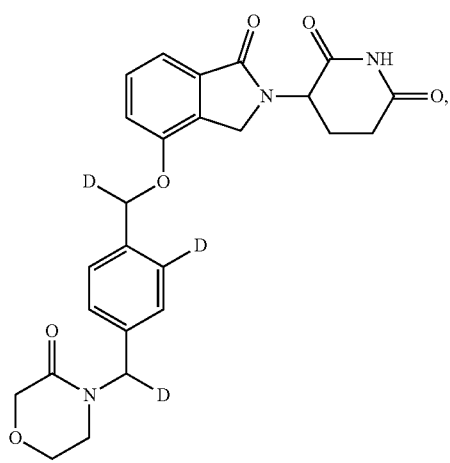
158 -continued
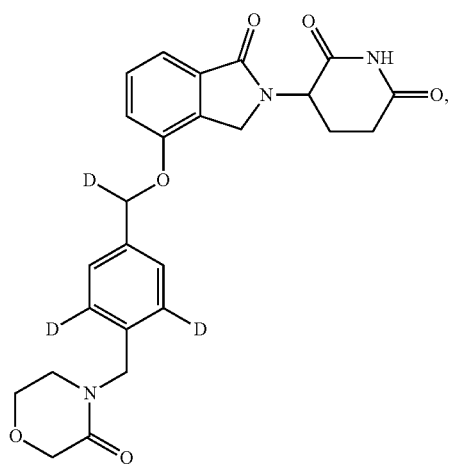
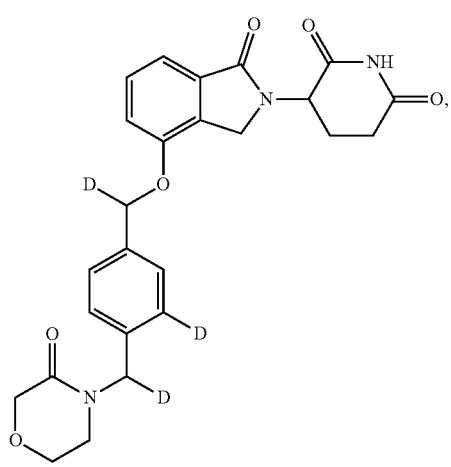
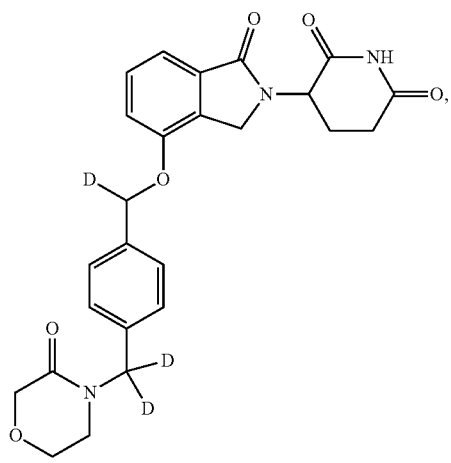

159
-continued
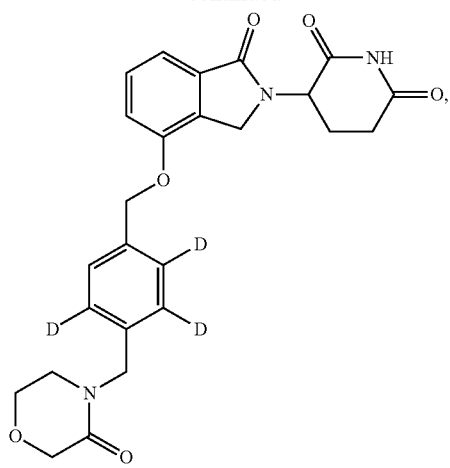
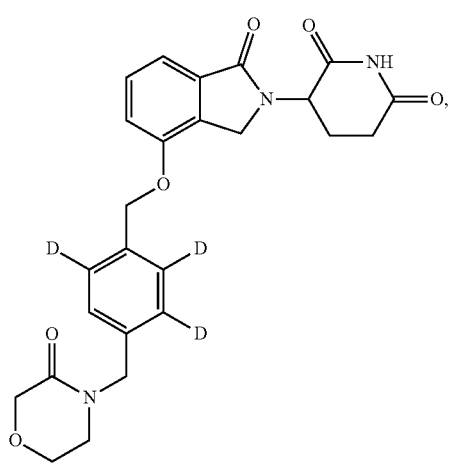
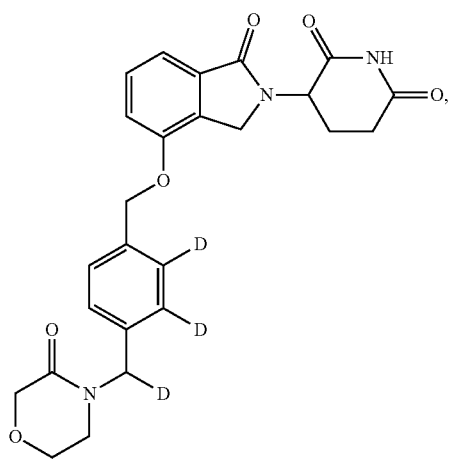
160
-continued
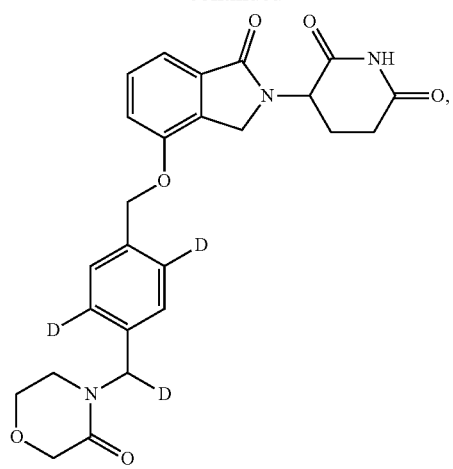
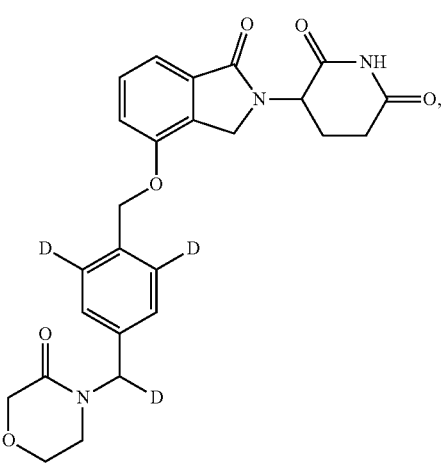
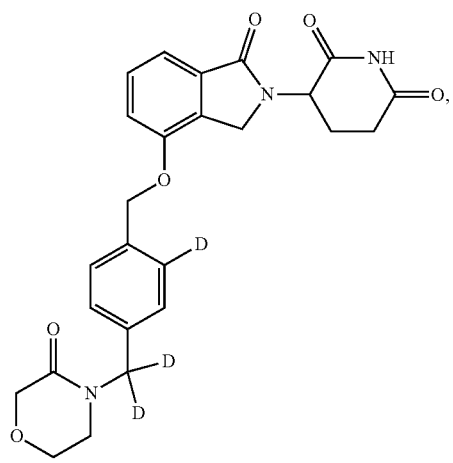

161
-continued
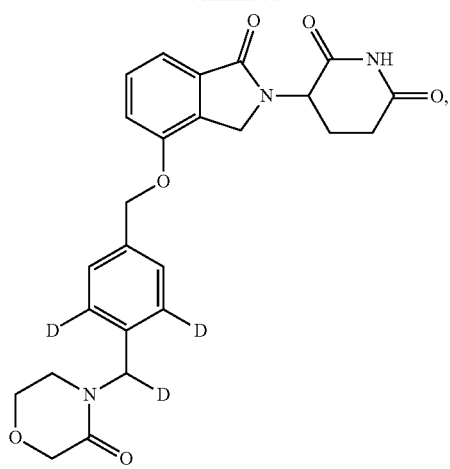
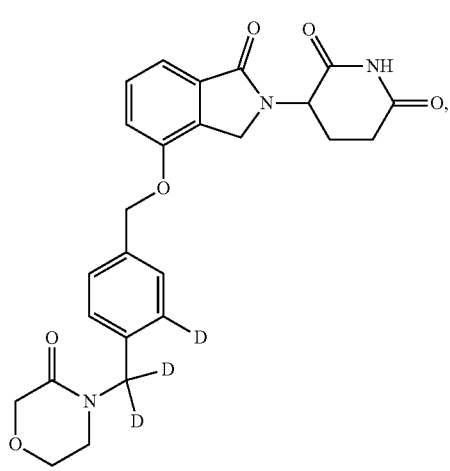
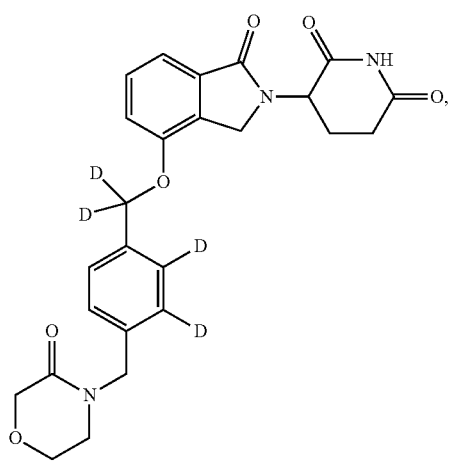
162
-continued
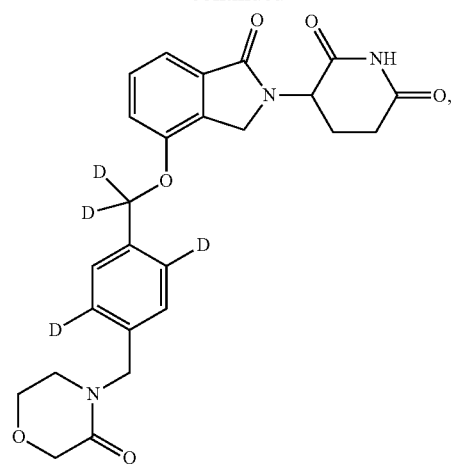
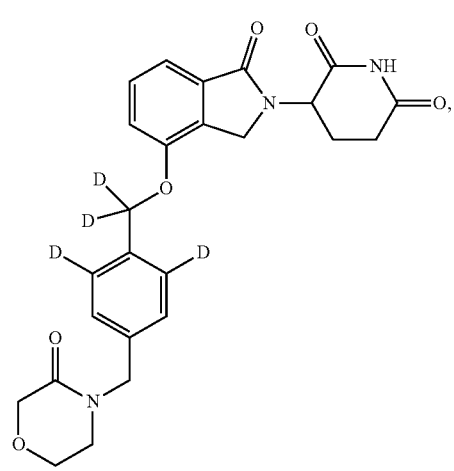

163
-continued
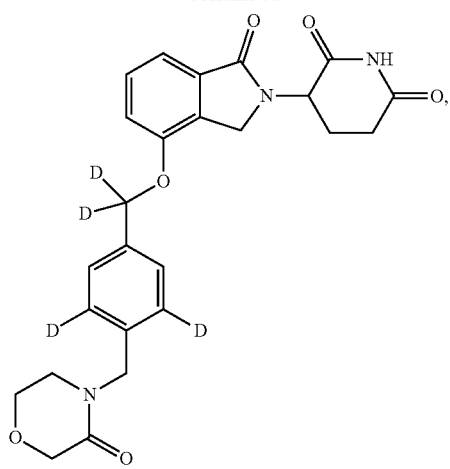
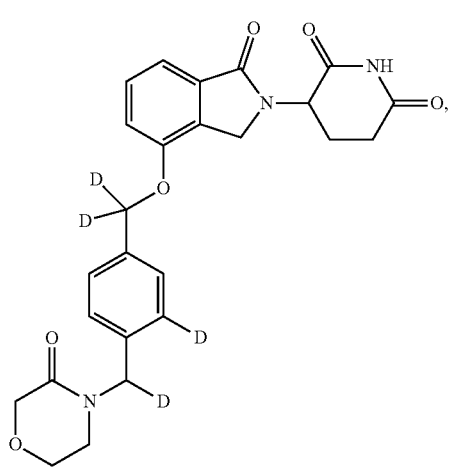
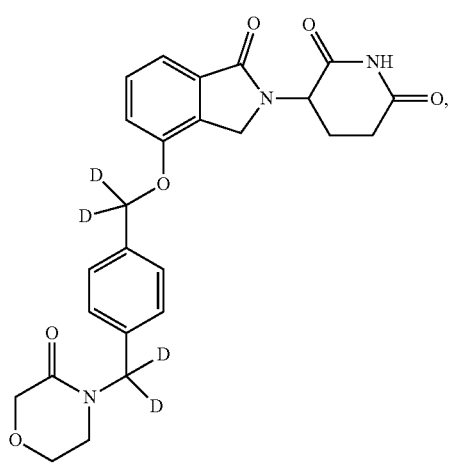
164
-continued
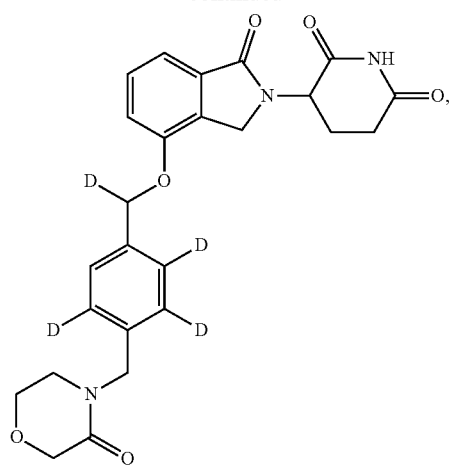
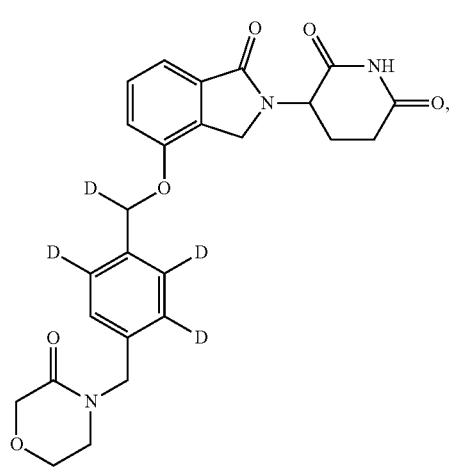
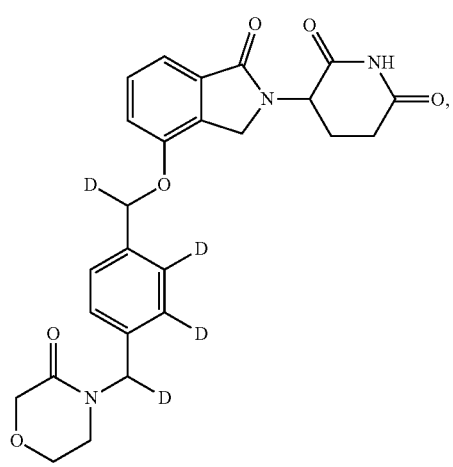

165
-continued
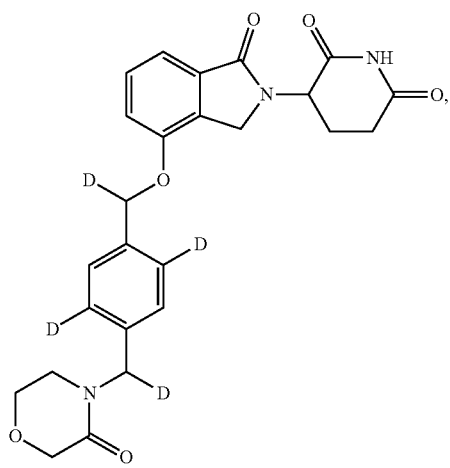
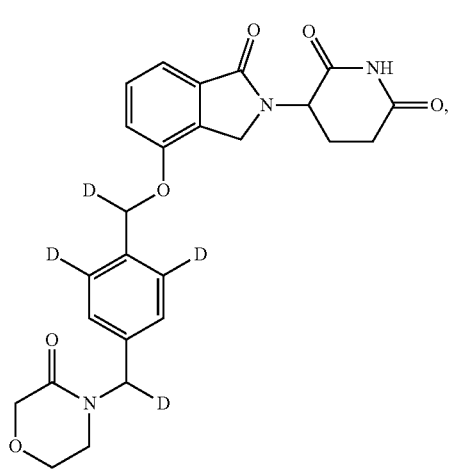
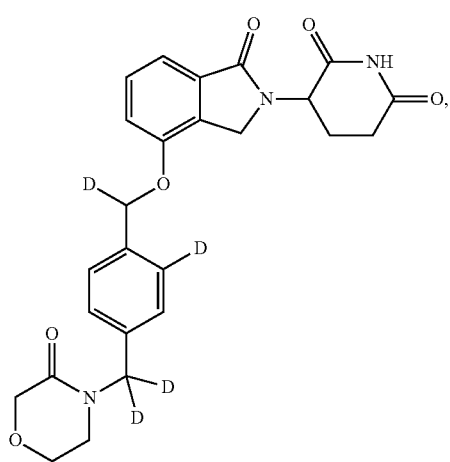
166
-continued
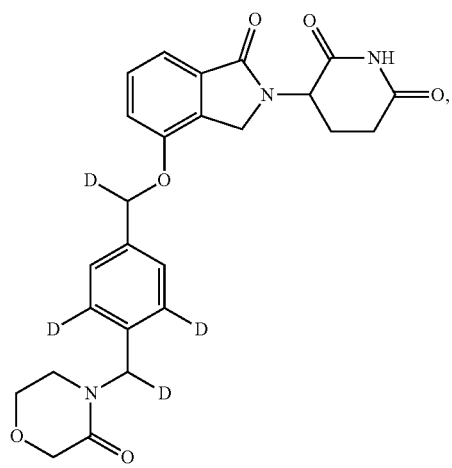
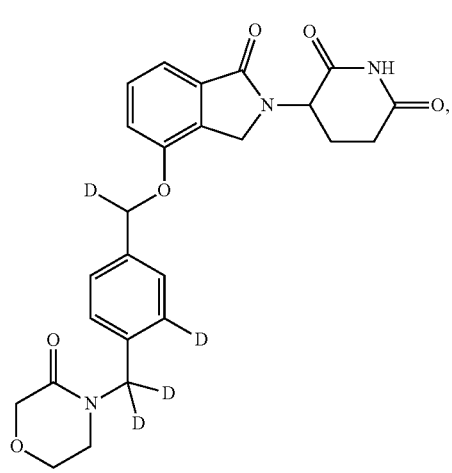
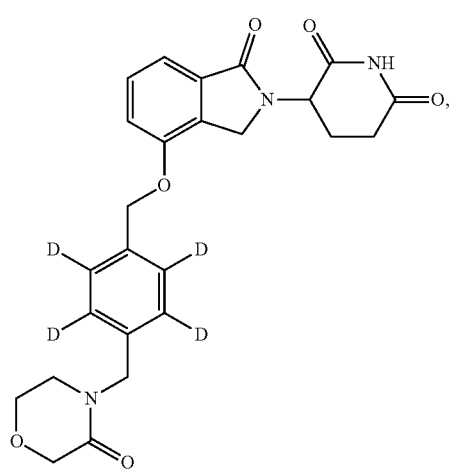

167
-continued
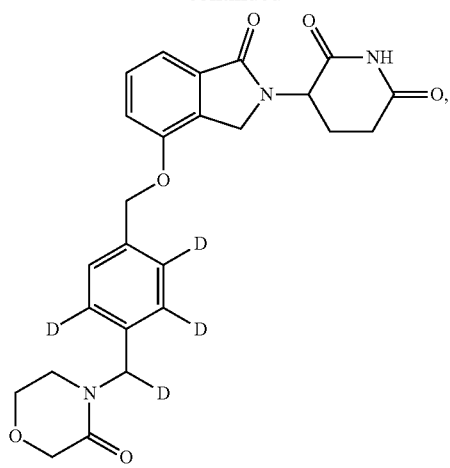
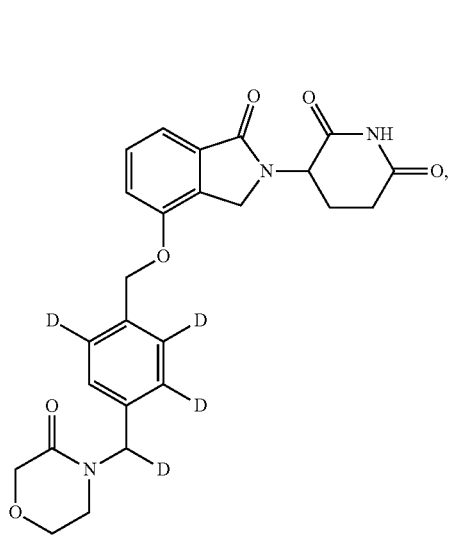
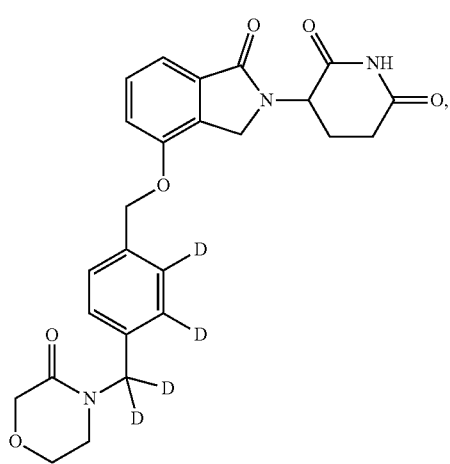
168
-continued
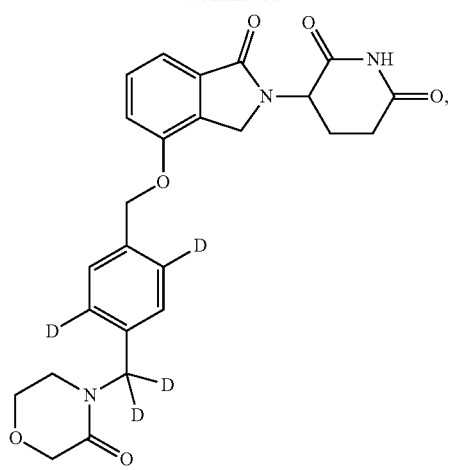
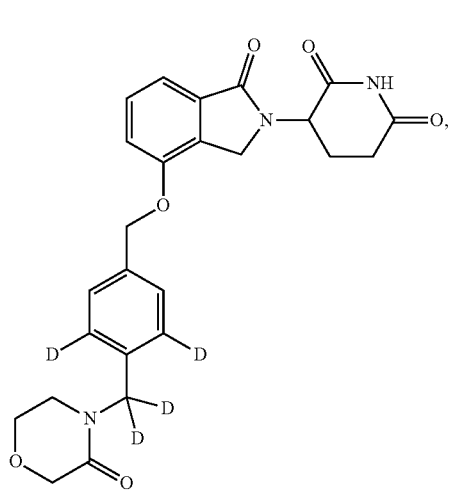
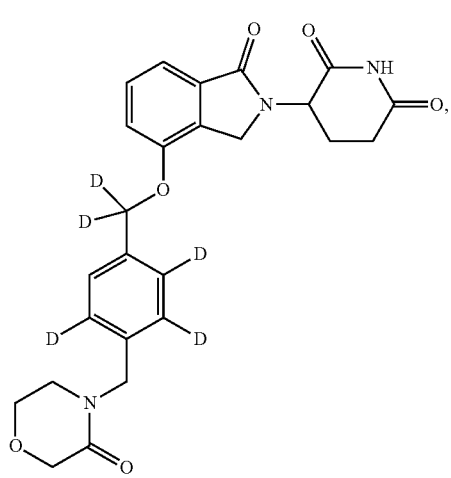

169
-continued
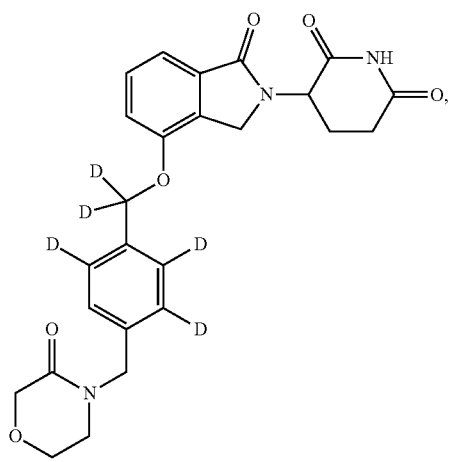
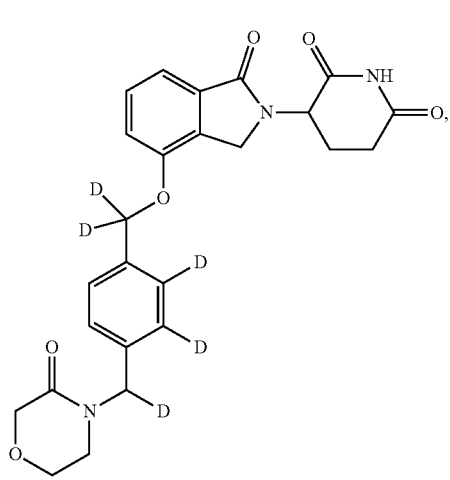
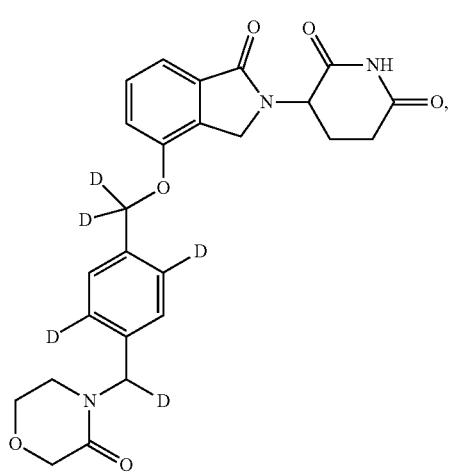
170
-continued
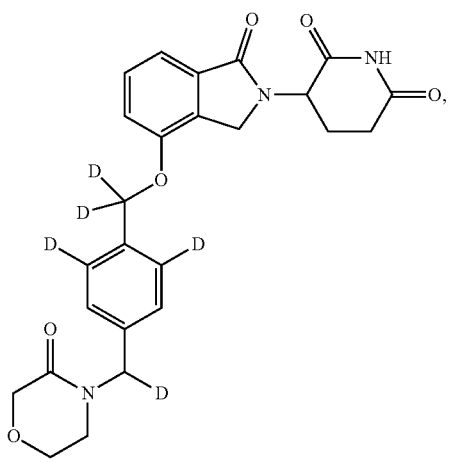
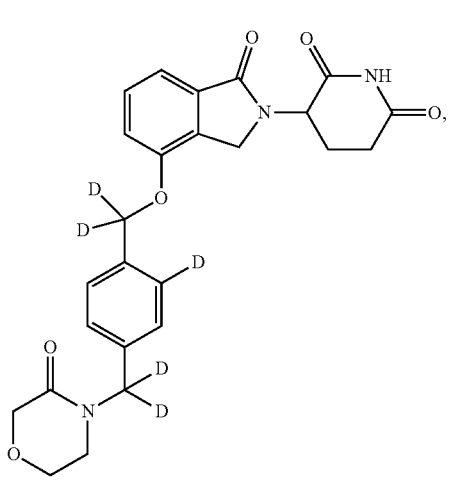
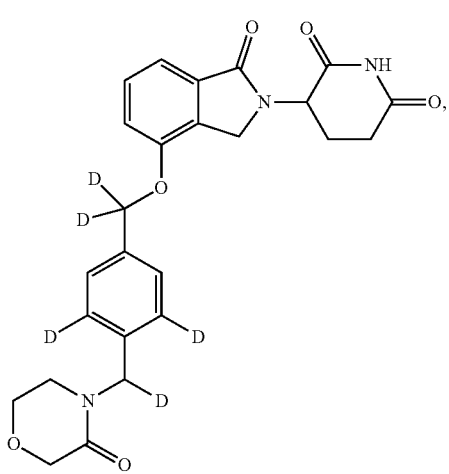

171
-continued
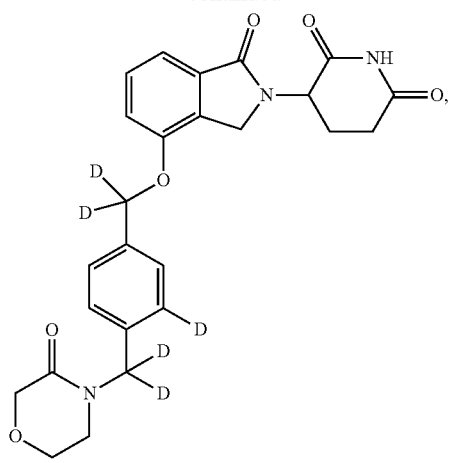
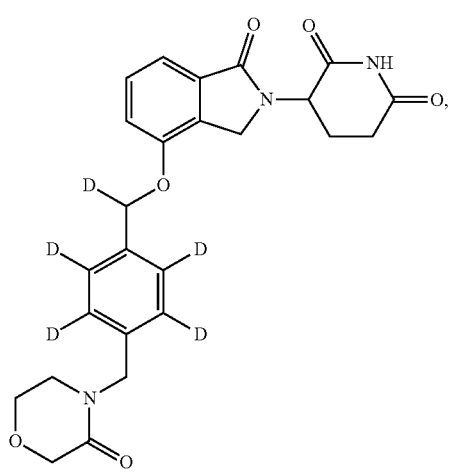
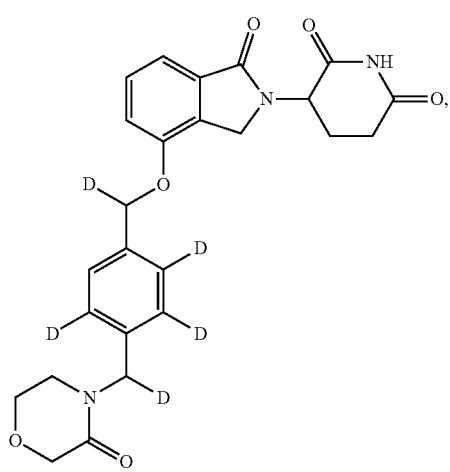
172
-continued
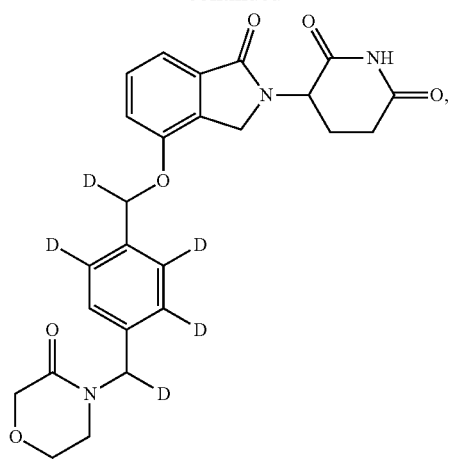
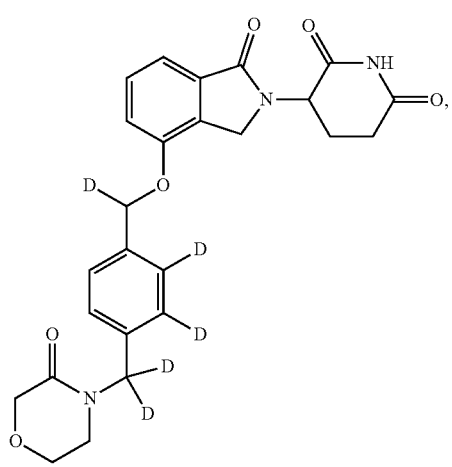

173
-continued
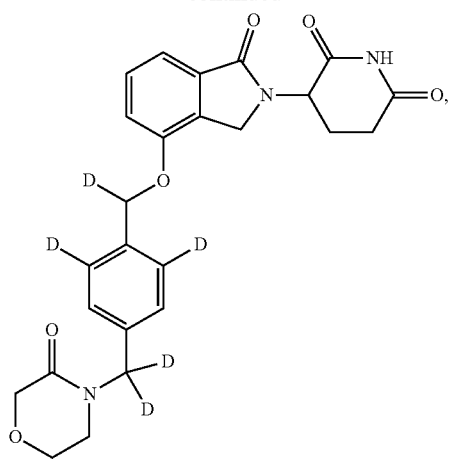
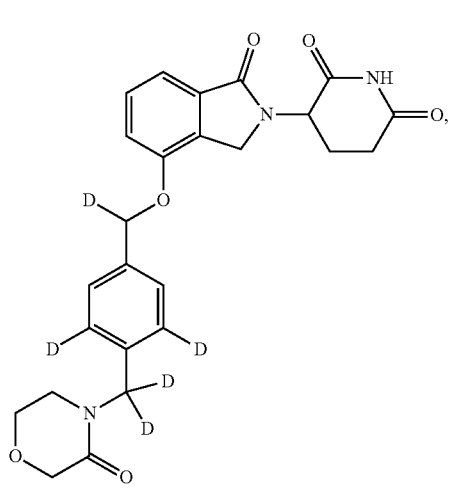
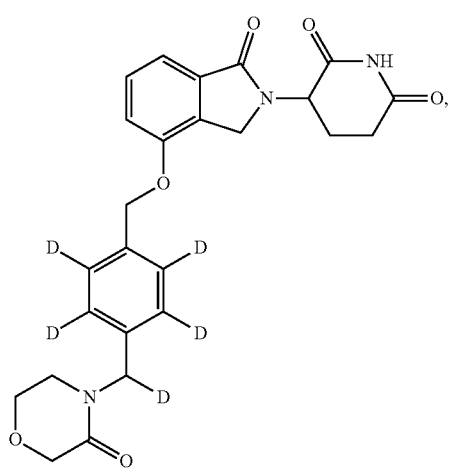
174
-continued
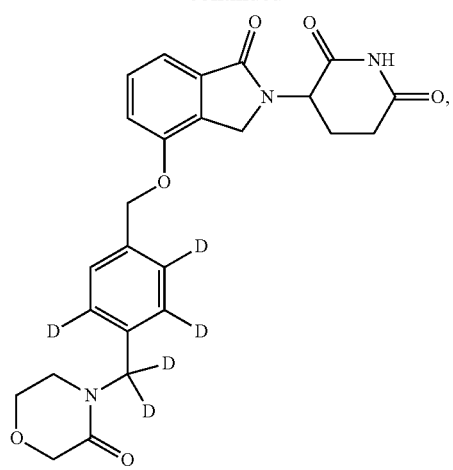
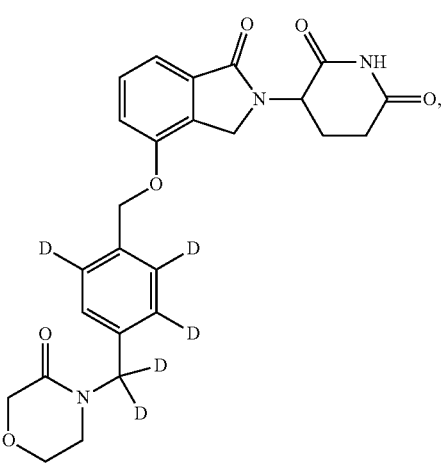
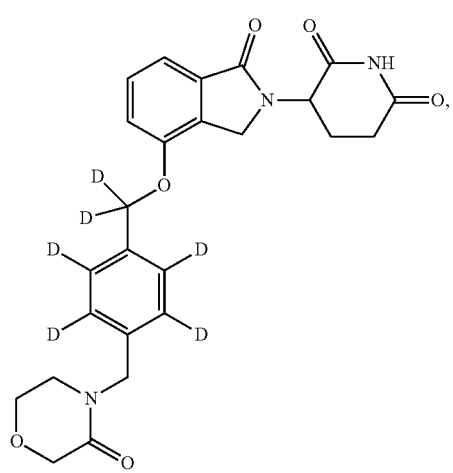

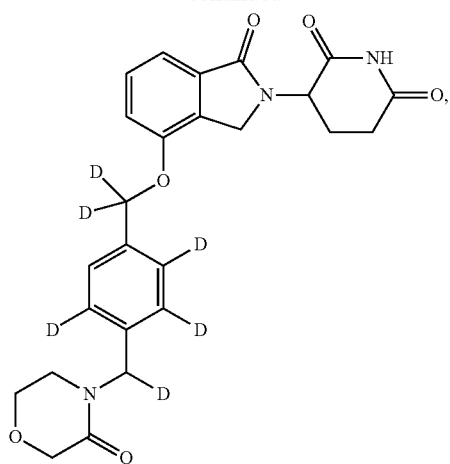
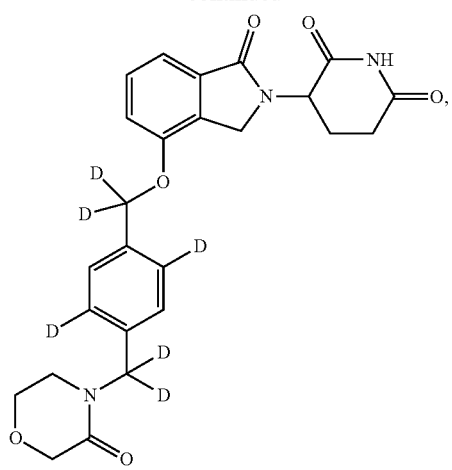
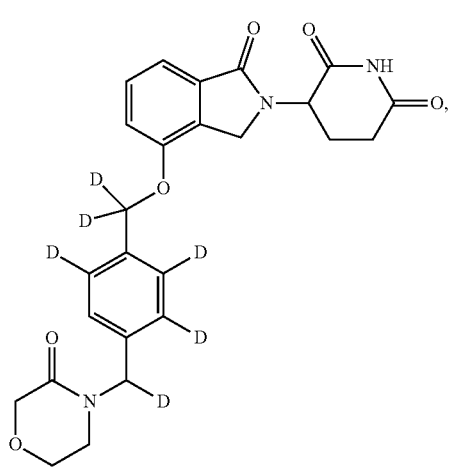
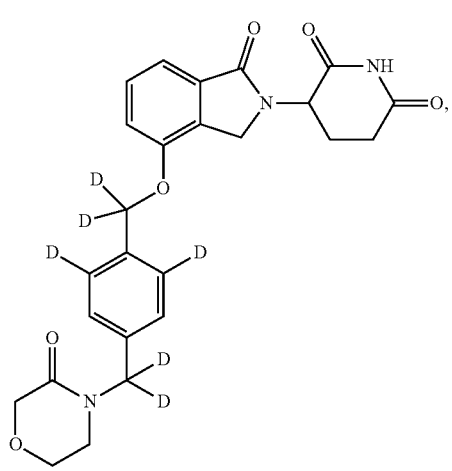
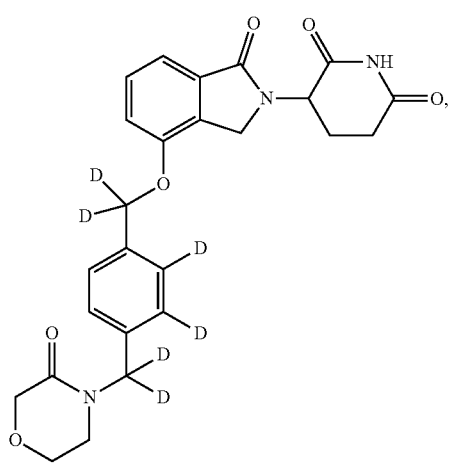
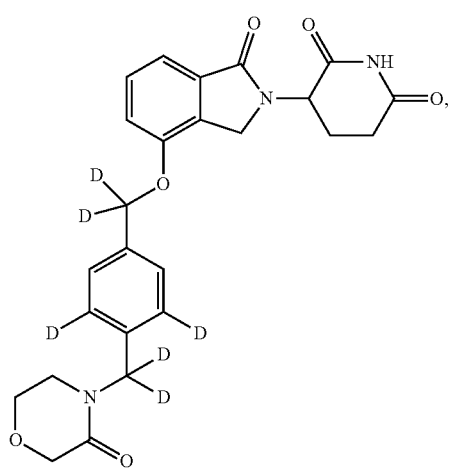

177
-continued
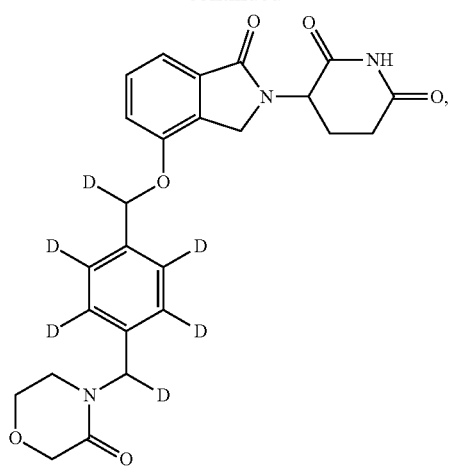
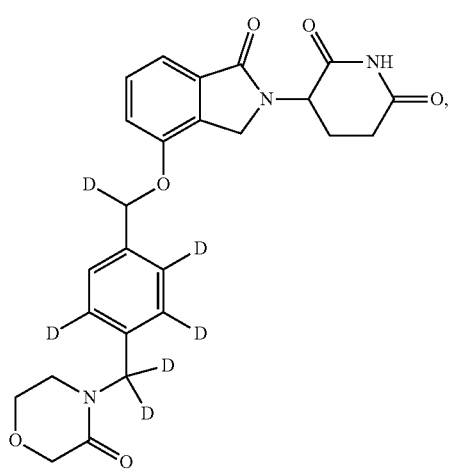
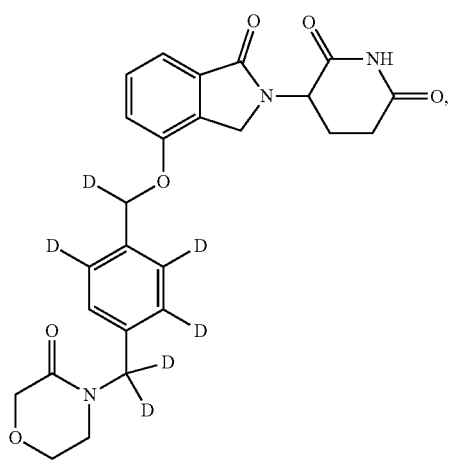
178
-continued
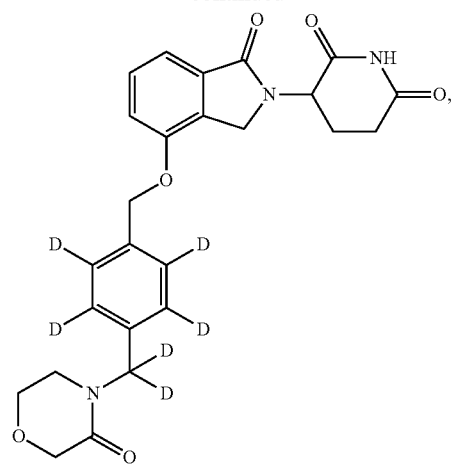
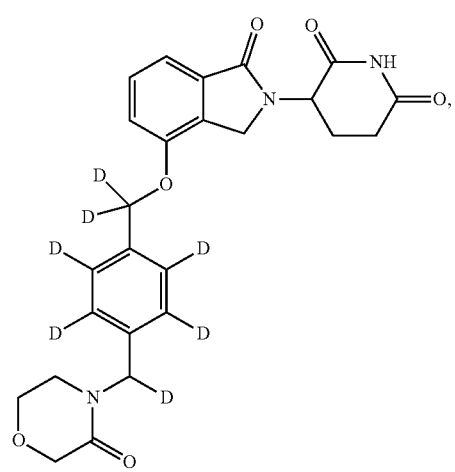
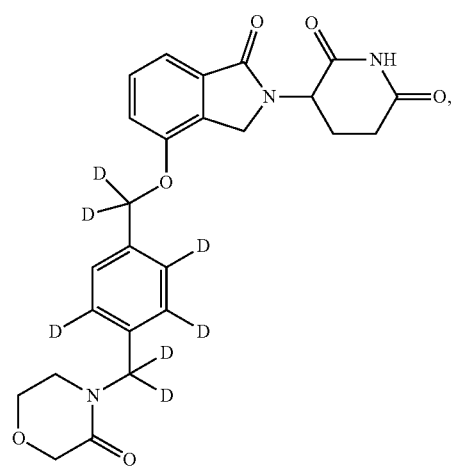

179
-continued
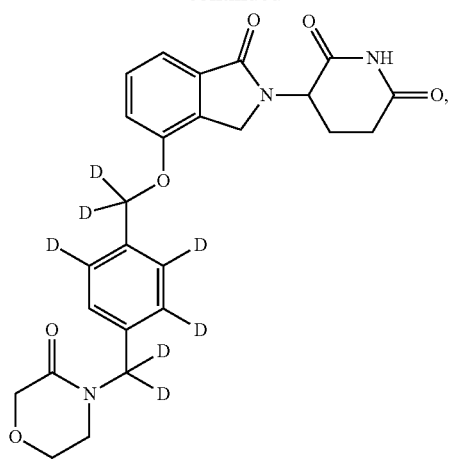
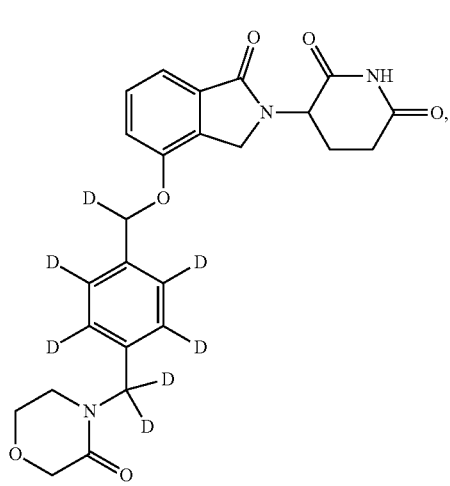
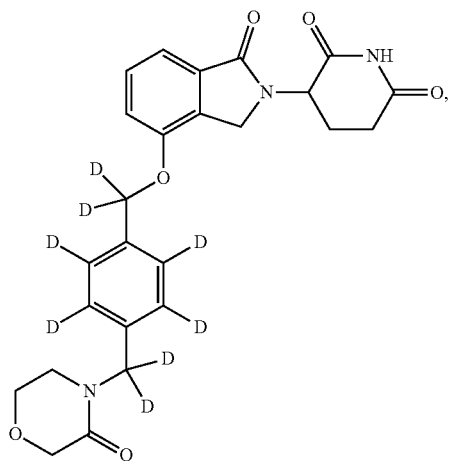
180
-continued
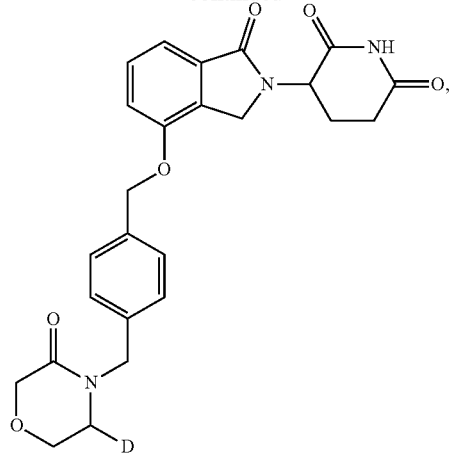
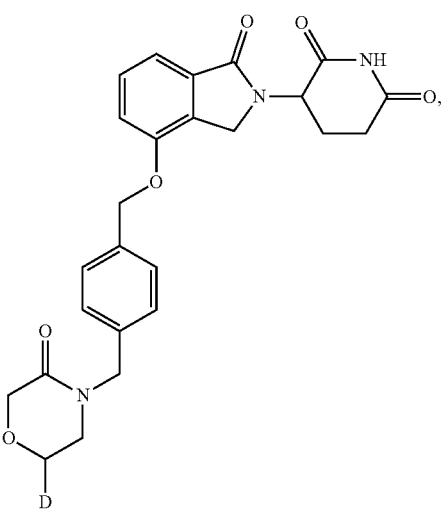
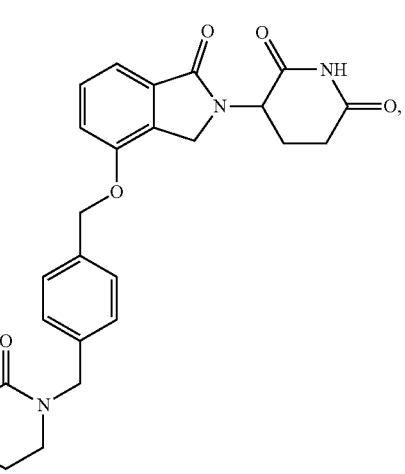

181
-continued
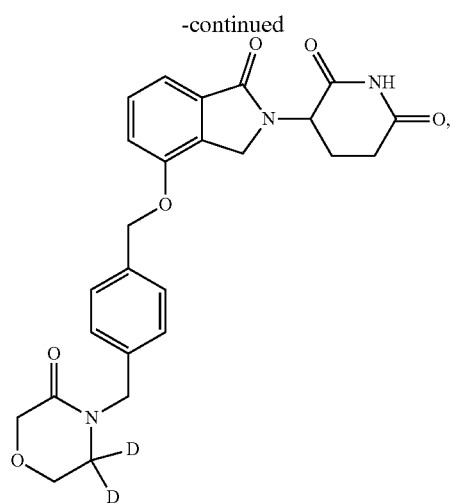
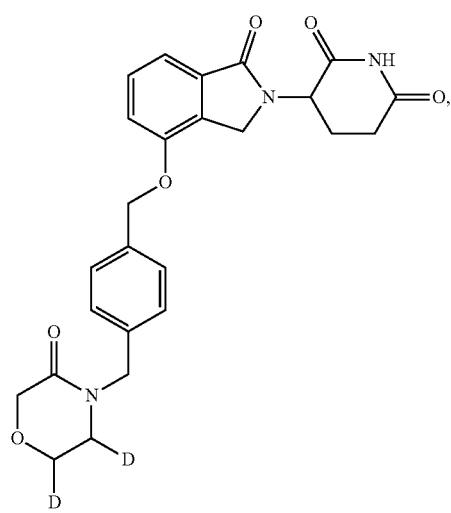
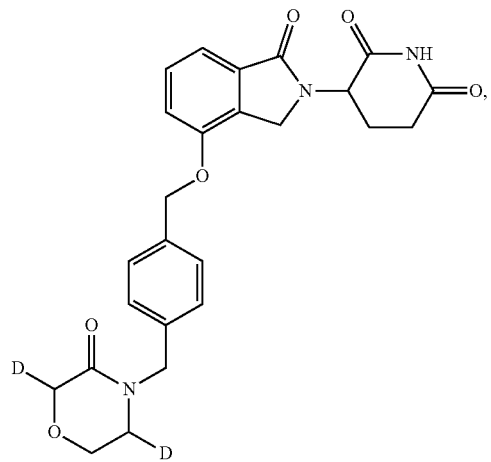
182
-continued
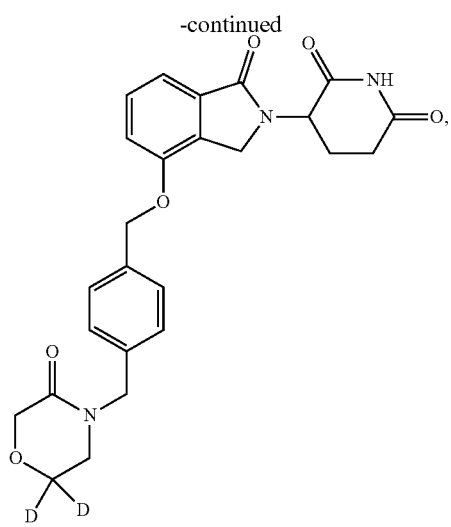
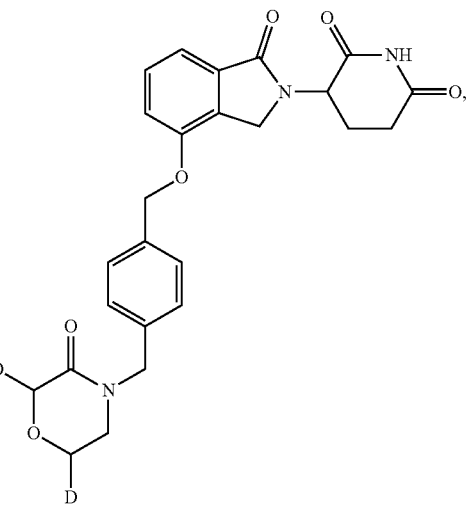
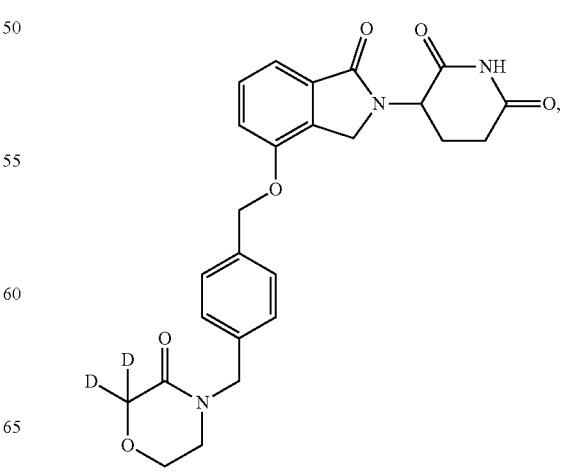

183
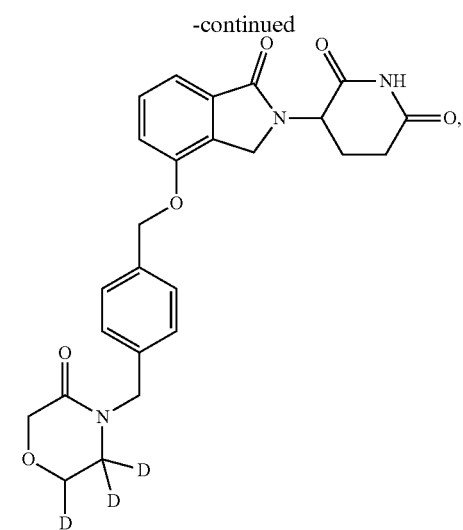
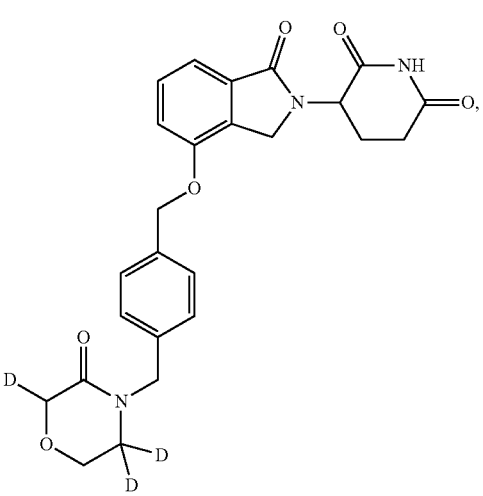
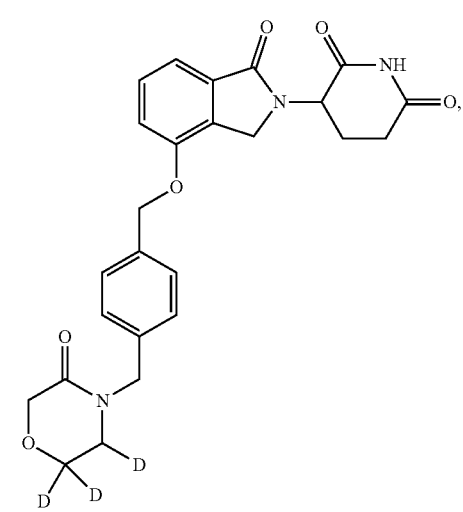
184
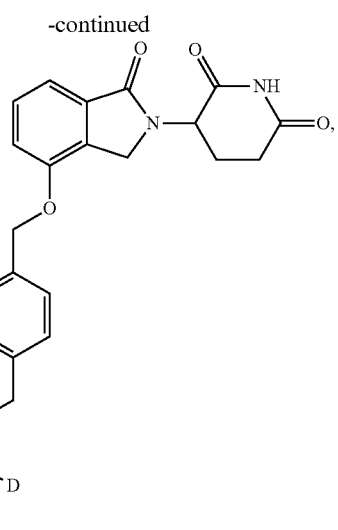
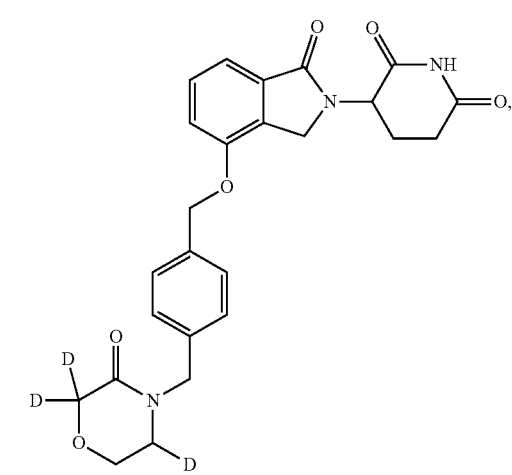
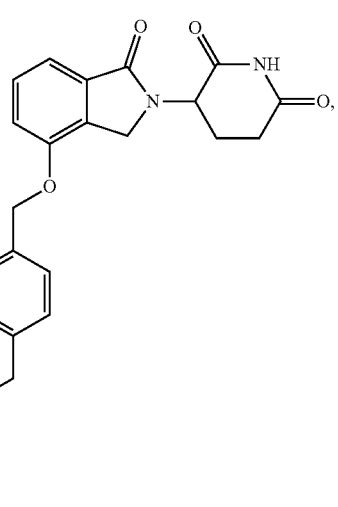

185
-continued
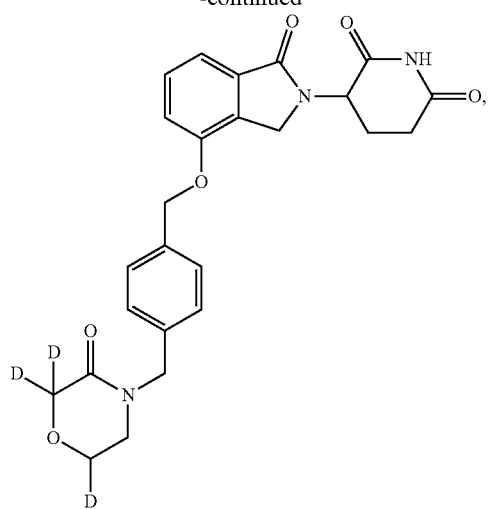
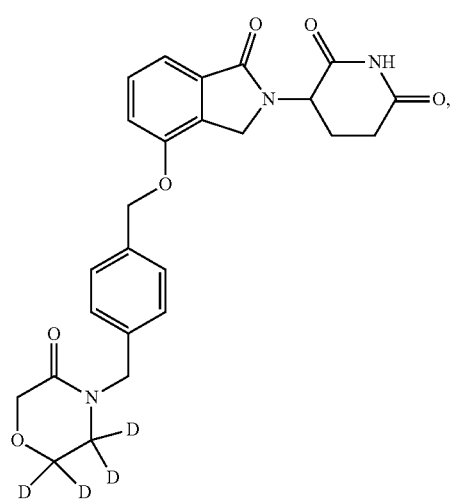
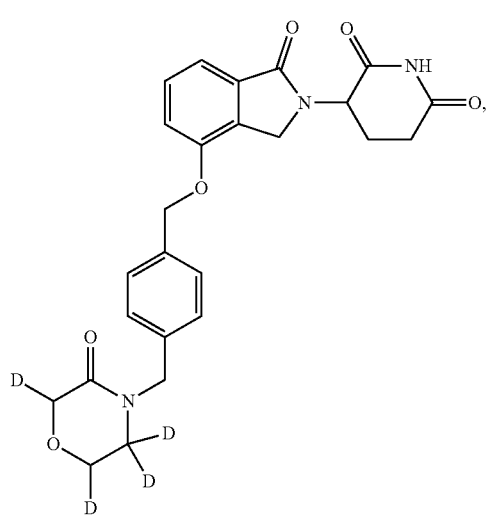
186
-continued
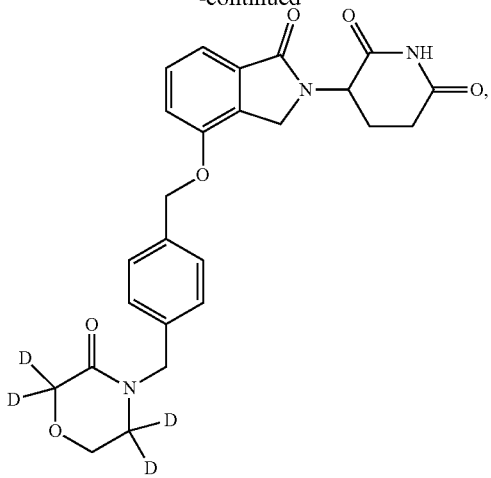
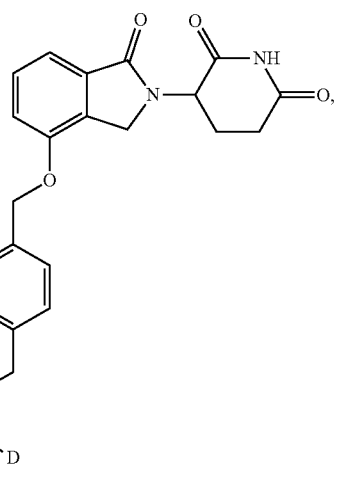
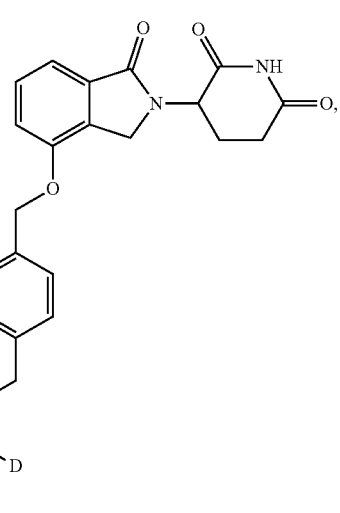

187
-continued
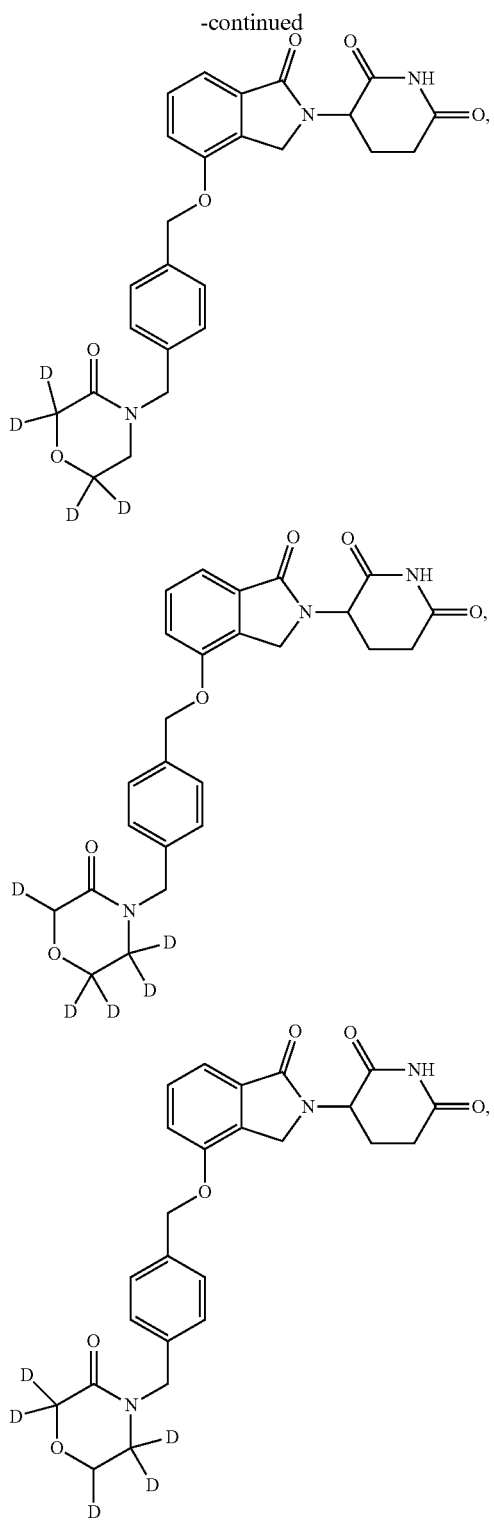
188
-continued
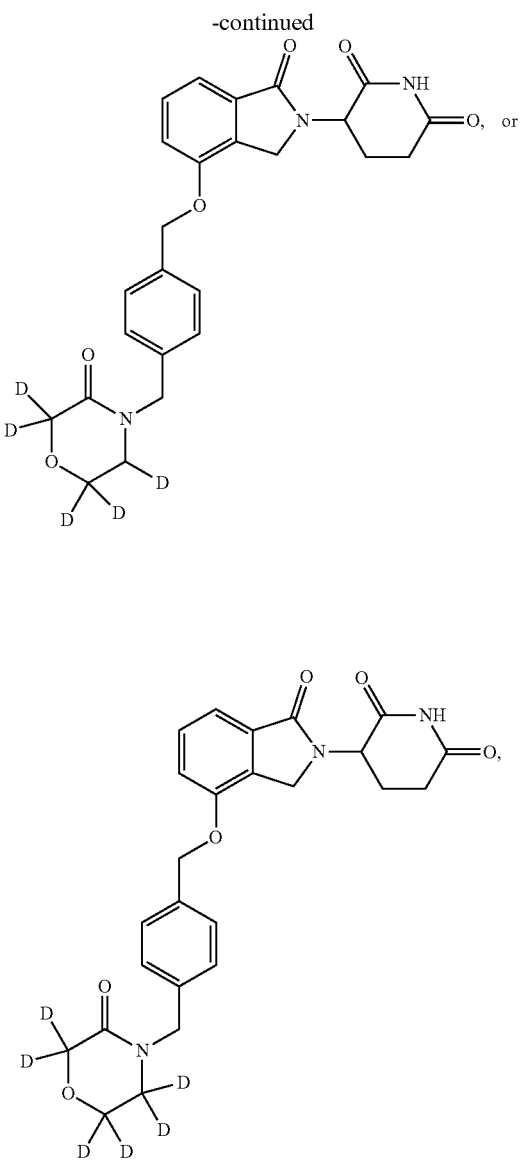
or an enantiomer or a mixture of enantiomers thereof, or a pharmaceutically acceptable salt, solvate, clathrate, polymorph, or co-crystal thereof.
19. A pharmaceutical composition comprising the compound of claim 1 and one or more pharmaceutically acceptable excipients.
* * * * *

UNITED STATES PATENT AND TRADEMARK OFFICE
CERTIFICATE OF CORRECTION

PATENT NO. : 10,434,095 B2
APPLICATION NO. : 15/881501
DATED : October 8, 2019
INVENTOR(S) : Man et al.

Page 1 of 1

It is certified that error appears in the above-identified patent and that said Letters Patent is hereby corrected as shown below:

In the Claims

In Column 127, Line 63 (part of Claim 7), insert a -- $Y^7$, -- between "$Y^6$," and "$Y^8$".

In Column 128, Line 3 (part of Claim 8), insert a -- $Y^7$, -- between "$Y^6$," and "$Y^8$".

Signed and Sealed this
Fourteenth Day of January, 2020

Andrei Iancu
*Director of the United States Patent and Trademark Office*